(12) United States Patent
Gingipalli et al.

(10) Patent No.: US 9,427,479 B2
(45) Date of Patent: Aug. 30, 2016

(54) TUBULYSIN DERIVATIVES

(71) Applicant: MedImmune LLC, Gaithersburg, MD (US)

(72) Inventors: Lakshmaiah Gingipalli, Waltham, MA (US); Dorin Toader, Gaithersburg, MD (US); Fengjiang Wang, Waltham, MA (US)

(73) Assignee: MedImmune LLC, Gaithersburg, MD (US)

( * ) Notice: Subject to any disclaimer, the term of this patent is extended or adjusted under 35 U.S.C. 154(b) by 0 days.

(21) Appl. No.: 14/683,196

(22) Filed: Apr. 10, 2015

(65) Prior Publication Data

US 2015/0291657 A1 Oct. 15, 2015

Related U.S. Application Data

(60) Provisional application No. 61/978,460, filed on Apr. 11, 2014.

(51) Int. Cl.

| | |
|---|---|
| A61K 38/07 | (2006.01) |
| A61K 47/48 | (2006.01) |
| C07K 5/033 | (2006.01) |
| A61K 38/05 | (2006.01) |
| C07K 5/02 | (2006.01) |
| C07K 5/062 | (2006.01) |
| C07D 417/12 | (2006.01) |
| C07D 417/14 | (2006.01) |

(52) U.S. Cl.
CPC ......... *A61K 47/48415* (2013.01); *A61K 38/05* (2013.01); *A61K 38/07* (2013.01); *A61K 47/48384* (2013.01); *A61K 47/48569* (2013.01); *C07D 417/12* (2013.01); *C07D 417/14* (2013.01); *C07K 5/02* (2013.01); *C07K 5/021* (2013.01); *C07K 5/06034* (2013.01)

(58) Field of Classification Search
None
See application file for complete search history.

(56) References Cited

U.S. PATENT DOCUMENTS

| | | | | |
|---|---|---|---|---|
| 8,580,820 | B2 * | 11/2013 | Zanda et al. | 514/317 |
| 2006/0148014 | A1 * | 7/2006 | Agoulnik et al. | 435/7.23 |
| 2008/0108820 | A1 * | 5/2008 | Campagna et al. | 546/245 |
| 2013/0129753 | A1 * | 5/2013 | Doroski et al. | 424/179.1 |
| 2013/0197259 | A1 * | 8/2013 | Cheng et al. | 560/22 |
| 2014/0227295 | A1 * | 8/2014 | Cong et al. | 424/179.1 |

FOREIGN PATENT DOCUMENTS

| | | | |
|---|---|---|---|
| WO | | 2015155345 A1 | 10/2015 |
| WO | | 2015157592 A1 | 10/2015 |
| WO | WO | 2015155345 A1 * | 10/2015 |
| WO | WO | 2015157592 A1 * | 10/2015 |

\* cited by examiner

*Primary Examiner* — Jeffrey E Russel
(74) *Attorney, Agent, or Firm* — Daniel Kopp

(57) ABSTRACT

Novel tubulysin derivatives which may be useful as cytotoxic agents to provide therapeutic benefits in the treatment of various types of cancers, alone, as drug conjugates or in combination with other chemotherapies are provided.

41 Claims, No Drawings

TUBULYSIN DERIVATIVES

CROSS-REFERENCE TO RELATED APPLICATIONS

This application claims the benefit under 35 U.S.C. §119 (e) to U.S. Application No. 61/978,460 filed on 11 Apr. 2014.

BACKGROUND

Tubulysins are a class of cytostatic tetrapeptides that were isolated from Myxobacteria (Sasse F et al J. Antibiotics, 2000, 879). The common features of the tubulysins are their tetrapeptidic structure, of which only Ile is naturally occurring amino acid and three others are complex unnatural amino acids: Mep (R—N-Mepipecolic acid), Tuv (tubuvaline) and Tut (tubulyrosine) or Tup (tubuphenylalanine) Later on additional members of the family were described (Steinmettz et al, Angew. Chem. Int. Ed. 2004, 4888). Most naturally occurring tubulysins showed pM cytotoxic activity against cancer cell lines that correlated with tubulin-polymerization inhibition. The mechanism of action of tubulysins was described by Sasse (Khalil M W et al Chem Bio Chem, 2006, 678) which showed that Tubulysin A is more efficacious in inhibiting tubulin polymerization than other vinca domain of beta-tubulin binders (phomopsin, dolastatin and hemiasterlin). Naturally occurring tubulysins showed consistent higher toxicity than dolastatin. Furthermore Tubulysin A was reported (Kaur G et al, Biochem. J, 2006, 235) to induce apoptosis in cancer cell lines and showed antiangiogenic activity in addition to potent antitumor activity in animal models. Following these findings considerable effort was invested into finding synthetic analogs with comparable potency to naturally occurring tubulysins. The presence of N,O-acetal-containing-Tuv has posed a challenge to synthesizing tubulysins and led to concerns regarding their stability. Several groups identified synthetic analogs that replaced the N,O-acetal with a plain methyl group without significant loss of cytotoxic activity (Patterson, A et al, Chem. Eur. J. 2007, 9534; Wipf P et al Org. Lett. 2007, 1605).

Several reports disclose conjugates of tubulysins with folate (Leamon C P et al, Cancer Res. 2008, 9839), cyclo-dextrin nano-conjugates (Schluep T S et al Clin. Cancer Res. 2009, 15:181) as well as dendrimer conjugates (Floyd W C, Chem Med Chem 2011, 49). One report discloses conjugation of tubulysins to monoclonal antibodies (US2011/0027274).

Novel tubulysin derivatives may be useful as cytotoxic agents to provide therapeutic benefits in the treatment of various types of cancers, alone, as drug conjugates or in combination with other chemotherapies.

SUMMARY OF THE INVENTION

The present disclosure provides compounds having the structure of Formula I:

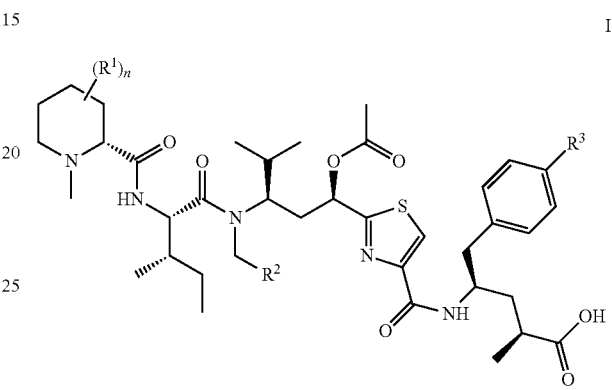

wherein:
$R^1$ is $CH_3$, or $CH_2 CH_3$;
$R^2$ is H or $CH_3$;
$R^3$ is H or $NH_2$; and
n is 1 or 2;
or a pharmaceutically acceptable salt thereof.

In some aspects n is 1 and $R^1$ is methyl.
In some aspects $R^2$ is methyl.
In some aspects $R^3$ is $NH_2$.
In some aspects n is 1, $R^1$ is methyl, $R^2$ is methyl and $R^3$ is $NH_2$.

Compounds of Formula I are cytotoxic and may be useful for treating cancer.

The present disclosure also provides compounds having the structure of Formula II:

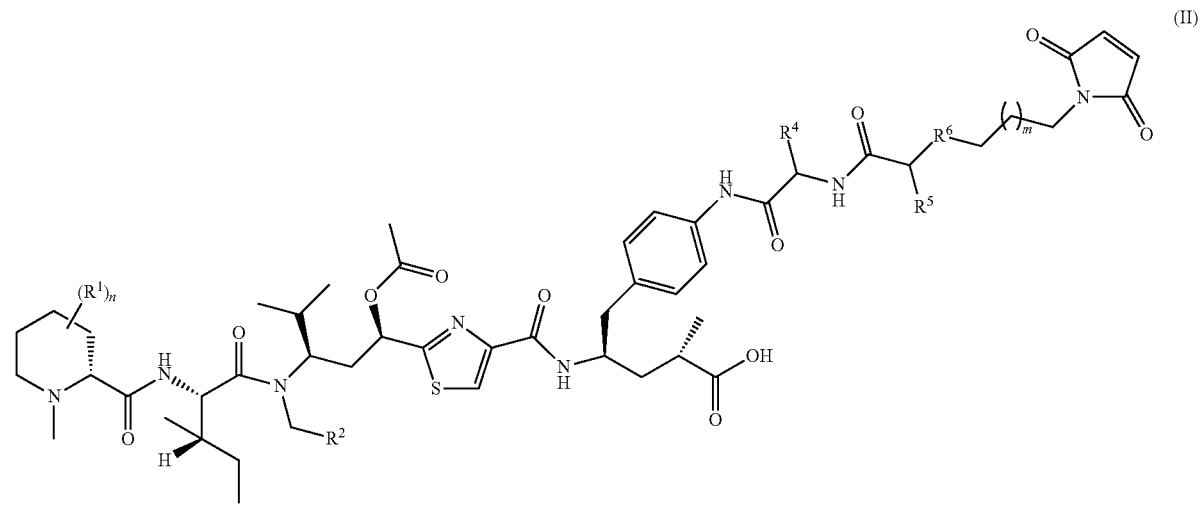

wherein:

$R^1$ is $CH_3$, or $CH_2 CH_3$;

$R^2$ is H or $CH_3$;

$R^4$ is $CH_3$, $(CH_2)_4NH_2$, or $(CH_2)_3NHC(=O)NH_2$;

$R^5$ is H; $C(CH_3)(CH_3)$;

$R^6$ is $NHC(=O)$, or $CH_2$;

n is 1 or 2; and m is 0, 1, 2 or 3.

In some aspects n is 1 and $R^1$ is methyl.

In some aspects $R^2$ is methyl.

In some aspects $R^3$ is $NH_2$.

In some aspects n is 1, $R^1$ is methyl, $R^2$ is methyl and $R^3$ is $NH_2$.

In some aspects $R^4$ is $(CH_2)_4NH_2$.

In some aspects $R^3$ is

In some aspects $R^6$ is $CH_2$

In some aspects m is 1.

In some aspects n is 1, m is 1, $R^1$ is methyl, $R^2$ is methyl and $R^3$ is $NH_2$, $R^4$ is $(CH_2)_4NH_2$, $R^5$ is H and $R^6$ is $CH_2$.

Compounds of Formula I and compounds of Formula II may be conjugated to an antibody through conventional means to provide an antibody drug conjugate (ADC). In some aspects of the disclosure compounds of Formula I and II are conjugated to an antibody through the antibody lysines or cysteines to provide an antibody drug conjugate (ADC). Some antibody drug conjugates of this disclosure are provided where the antibody is a monoclonal antibody. Other antibody drug conjugates of this disclosure are provided where the antibody is specific to a cancer antigen. Other antibody drug conjugates of the disclosure are provided wherein the antibody is alemtuzumab, bevacizumab, brentuximab, cetuximab, gemtuzumab, ipilimumab, ofatumumab, panitumumab, rituximab, tositumomab, or trastuzumab.

The instant disclosure also provides a pharmaceutical composition comprising a compound of Formula I, or a pharmaceutically acceptable salt thereof and a pharmaceutically acceptable carrier. Pharmaceutical compositions comprising ADC of the present disclosure and a pharmaceutically acceptable carrier are provided.

Methods of treating cancer are also provided by this disclosure comprising administering to a subject suffering from cancer, an effective amount of a compound of Formula I or a compound of Formula II. Methods of treating cancer are also provided by this disclosure comprising administering to a subject suffering from cancer, an effective amount of an antibody-drug conjugate of a compound of Formula I or compound of Formula II conjugated to an antibody. In some aspects of the disclosure the subject is suffering from squamous cell cancer, small-cell lung cancer, non-small cell lung cancer, gastrointestinal cancer, Hodgkin's lymphoma, non-Hodgkin's lymphoma, pancreatic cancer, glioblastoma, glioma, cervical cancer, ovarian cancer, liver cancer, bladder cancer, breast cancer, colon cancer, colorectal cancer, endometrial carcinoma, myeloma, salivary gland carcinoma, kidney cancer, basal cell carcinoma, melanoma, prostate cancer, vulval cancer, thyroid cancer, testicular cancer, esophageal cancer, head and neck cancers, mucinous ovarian cancer, cholangiocarcinoma or renal papillary carcinoma.

Also provided are methods of treating cancer comprising administering a pharmaceutical composition comprising a compound of Formula I to a subject in need thereof. Also provided by this disclosure is a method of treating cancer comprising administering a pharmaceutical composition comprising an ADC of the present disclosure, to a subject in need thereof.

In some aspects, the method further comprises administering at least one additional therapeutic agent. In some aspects, the at least one additional therapeutic agent is a radionuclide or a chemotherapeutic agent.

DETAILED DESCRIPTION

The present disclosure provides compounds having the structure of Formula I:

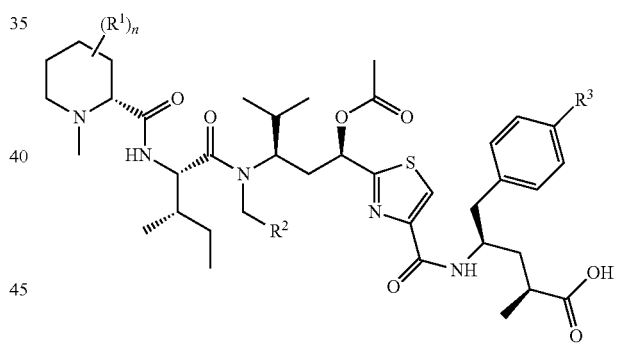

I wherein:

$R^1$ is $CH_3$, or $CH_2 CH_3$;

$R^2$ is H or $CH_3$;

$R^3$ is H or $NH_2$; and n is 1 or 2; or a pharmaceutically acceptable salt thereof.

In some aspects n is 1 and $R^1$ is methyl.

In some aspects $R^2$ is methyl.

In some aspects $R^3$ is $NH_2$.

In some aspects n is 1, $R^1$ is methyl, $R^2$ is methyl and $R^3$ is $NH_2$.

Specific examples of compounds of the disclosure according to Formula I include compounds (Ii) through (Ivi).

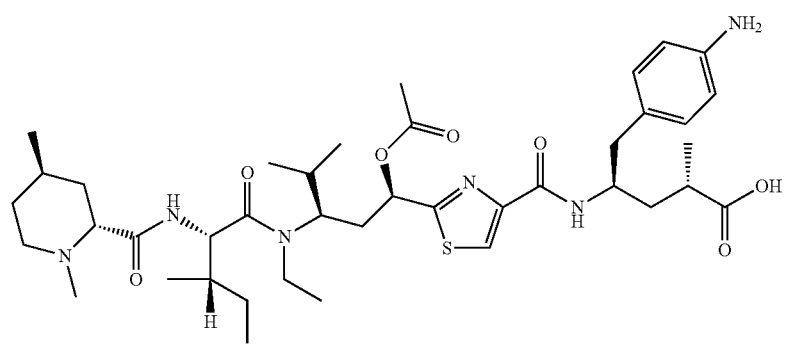
(Ii)
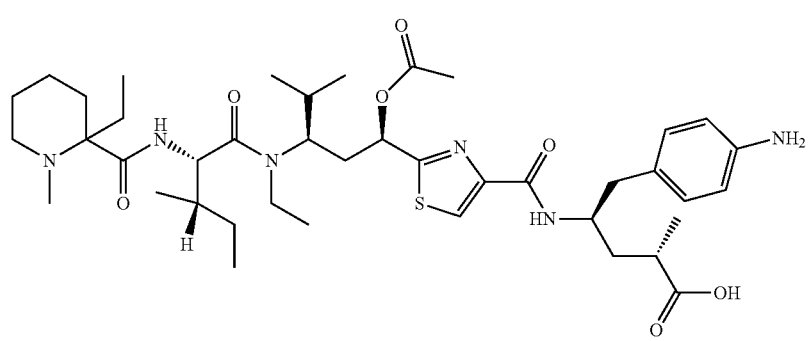
(Iii)
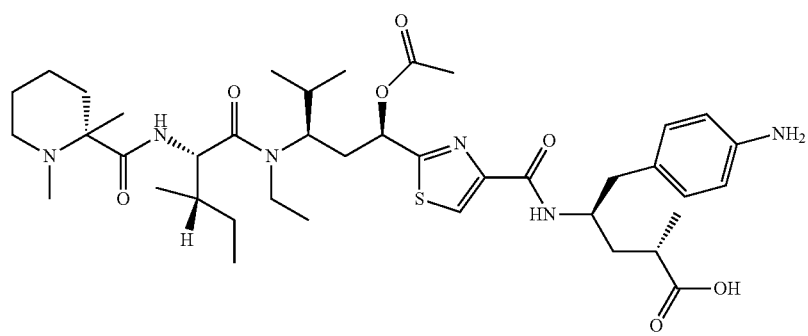
(Iiii)
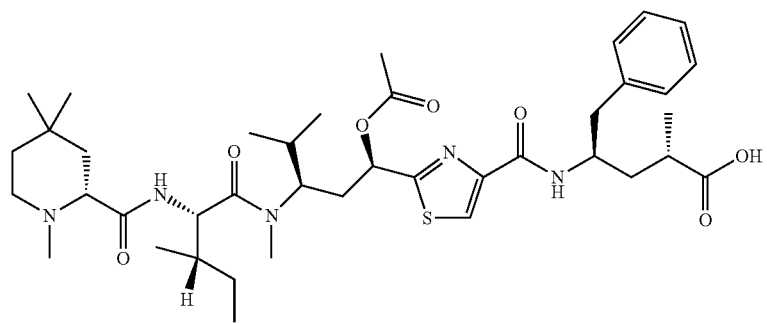
(Iiv)
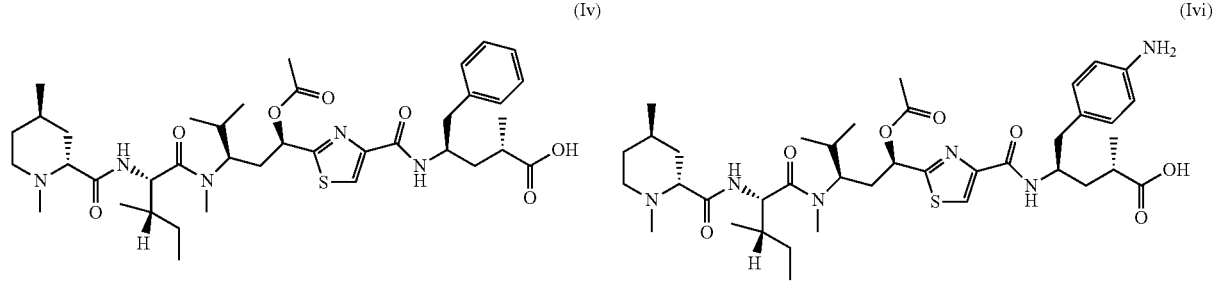
(Iv) (Ivi)

The present disclosure provides compounds having the structure of Formula II:

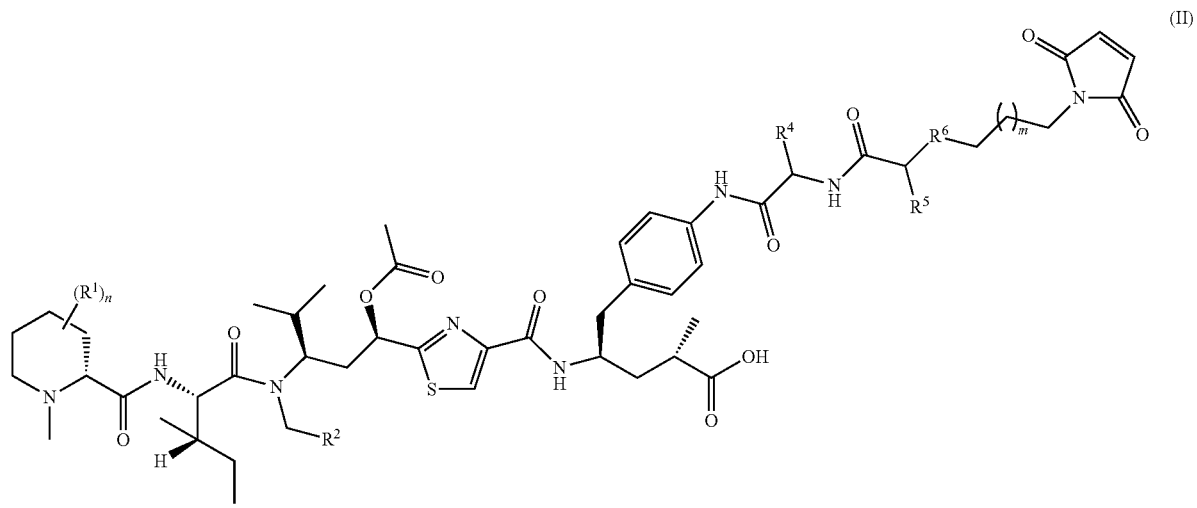

wherein:
R$^1$ is CH$_3$, or CH$_2$ CH$_3$;
R$^2$ is H or CH$_3$;
R$^4$ is CH$_3$, (CH$_2$)$_4$NH$_2$, or (CH$_2$)$_3$NHC(=O)NH$_2$;
R$^5$ is H; C(CH$_3$)(CH$_3$);
R$^6$ is NHC(=O), or CH$_2$;
n is 1 or 2; and
m is 0, 1, 2 or 3.
In some aspects n is 1 and R$^1$ is methyl.
In some aspects R$^2$ is methyl.

In some aspects R$^3$ is NH$_2$.
In some aspects n is 1, R$^1$ is methyl, R$^2$ is methyl and R$^3$ is NH$_2$.
In some aspects R$^4$ is (CH$_2$)$_4$NH$_2$.
In some aspects R$^5$ is H.
In some aspects R$^6$ is CH$_2$.
In some aspects m is 1.

Specific examples of compounds of the disclosure according to Formula II include compounds (IIi) through (IIiv).

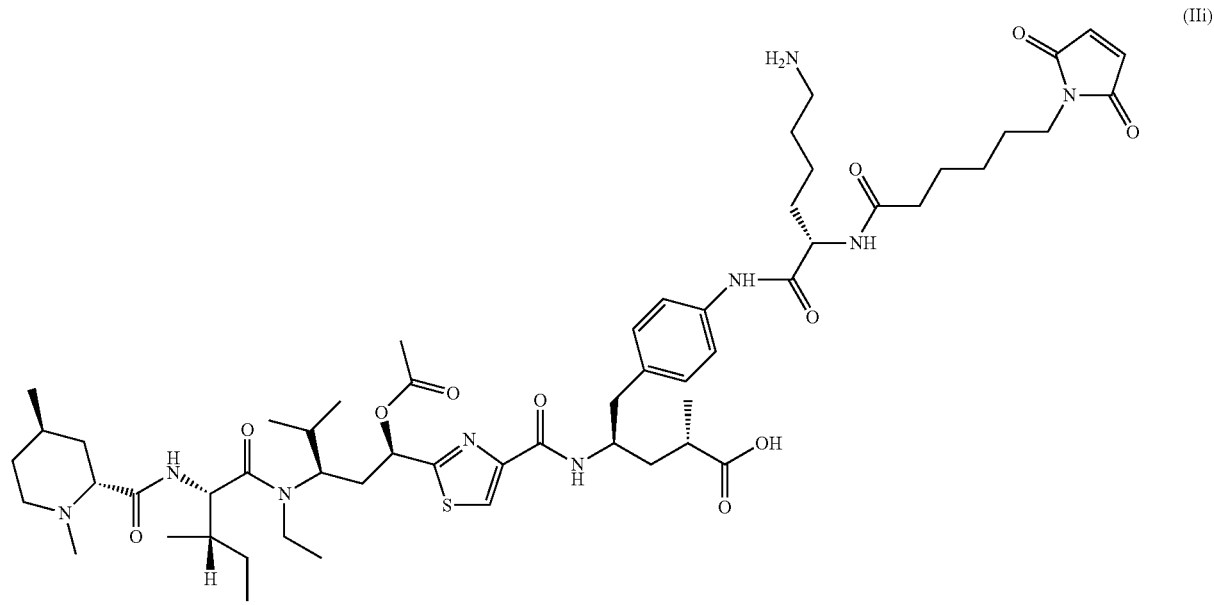

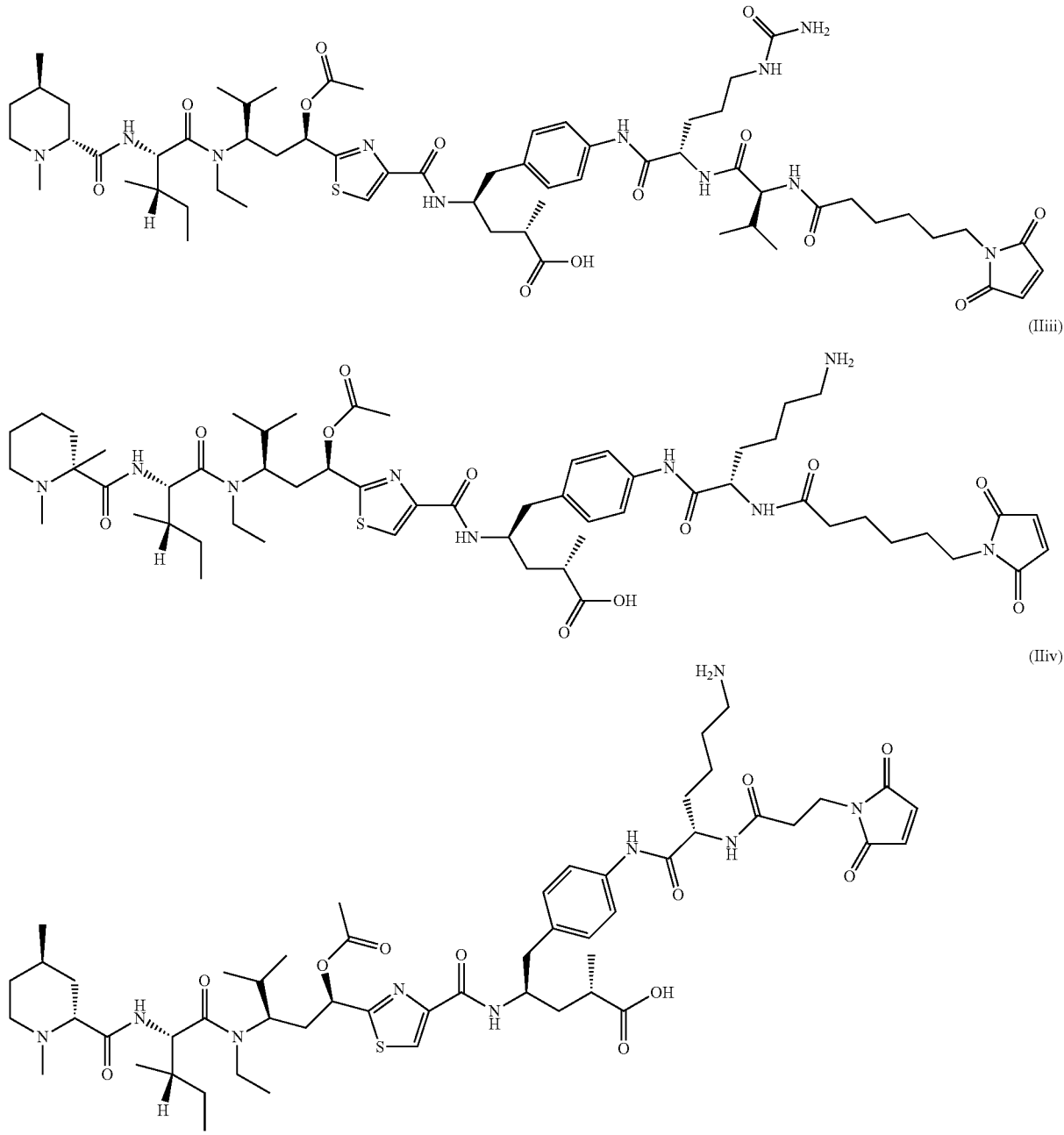

In some aspects of the disclosure n is 1. In other aspects of the disclosure n is 2. Where n is 2, $R^1$ substitutions on the piperidine ring may occur on a single carbon atom in the ring or may be on different carbon atoms in the ring. In some aspects of the disclosure when n is 1, $R^1$ substitution of the ring is para to the nitrogen. In other aspects of the disclosure when n is 1, $R^1$ substitution is meta to the nitrogen in the piperidine ring.

Compounds of Formula I and II may be conjugated to antibodies to form antibody drug conjugates. (ADC). In the ADC complex, compounds of Formula II, serve as therapeutic moieties which are delivered to a therapeutic target of interest by the antibody to which they are conjugated. Pharmaceutical compositions comprising ADCs formed by the conjugation of compounds of Formulas I and Formula II and an antibody are also provided. Also provided are methods of making ADCs using compounds of Formulas I and compounds of Formula II. Methods of treating cancer in a subject in need thereof by administering ADCs of the present disclosure are also provided. Methods of the treating cancer further provide administering ADC of the present invention in combination with a chemotherapeutic agent.

In order that the present invention can be more readily understood, certain terms are first defined. Additional definitions are set forth throughout the detailed description.

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiments may be practiced in many ways and the claims include any equivalents thereof.

Before describing the present invention in detail, it is to be understood that this invention is not limited to specific compositions or process steps, as such can vary. As used in this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects, which can be had by reference to the specification as a whole. Accordingly, the terms defined immediately below are more fully defined by reference to the specification in its entirety.

It is understood that wherever aspects are described herein with the language "comprising," otherwise analogous aspects described in terms of "consisting of" and/or "consisting essentially of" are also provided.

Amino acids are referred to herein by either their commonly known three letter symbols or by the one-letter symbols recommended by the IUPAC-IUB Biochemical Nomenclature Commission.

The terms "inhibit," "block," and "suppress" are used interchangeably herein and refer to any statistically significant decrease in biological activity, including full blocking of the activity. For example, "inhibition" can refer to a decrease of about 10%, 20%, 30%, 40%, 50%, 60%, 70%, 80%, 90% or 100% in biological activity.

Cellular proliferation can be assayed using art recognized techniques which measure rate of cell division, and/or the fraction of cells within a cell population undergoing cell division, and/or rate of cell loss from a cell population due to terminal differentiation or cell death (e.g., thymidine incorporation).

The terms "antibody" or "immunoglobulin," as used interchangeably herein, include whole antibodies and any antigen binding fragment or single chains thereof and combinations thereof (e.g., bispecific antibodies).

A typical antibody comprises at least two heavy (H) chains and two light (L) chains interconnected by disulfide bonds. Each heavy chain is comprised of a heavy chain variable region (abbreviated herein as VH) and a heavy chain constant region (abbreviated herein as CH). The heavy chain constant region is comprised of three domains, CH1, CH2, and CH3. Each light chain is comprised of a light chain variable region (abbreviated herein as VL) and a light chain constant region. The light chain constant region is comprised of one domain, CL. The VH and VL regions can be further subdivided into regions of hypervariability, termed Complementarity Determining Regions (CDR), interspersed with regions that are more conserved, termed framework regions (FW). Each VH and VL is composed of three CDRs and four FWs, arranged from amino-terminus to carboxy-terminus in the following order: FW1, CDR1, FW2, CDR2, FW3, CDR3, FW4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. Exemplary antibodies of the present disclosure include typical antibodies, scFvs, and combinations thereof where, for example, an scFv is covalently linked (for example, via peptidic bonds or via a chemical linker) to the N-terminus of either the heavy chain and/or the light chain of a typical antibody, or intercalated in the heavy chain and/or the light chain of a typical antibody.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain variable fragment (scFv), disulfide stabilized scFvs, multispecific antibodies such as bispecific antibodies generated from at least two intact antibodies and/or antigen binding fragments thereof, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity.

An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc. to form ADCs.

The terms "antigen binding fragment" refers to a portion of an intact antibody and refers to the antigenic determining variable regions of an intact antibody. It is known in the art that the antigen binding function of an antibody can be performed by fragments of a full-length antibody. Examples of antibody fragments include, but are not limited to Fab, Fab', F(ab')2, and Fv fragments, linear antibodies, single chain antibodies, and multispecific antibodies formed from antibody fragments.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants.

The term "monoclonal antibody" encompasses both intact and full-length monoclonal antibodies as well as antibody fragments (such as Fab, Fab', F(ab')2, Fv), single chain variable fragments (scFv), fusion proteins comprising an antibody portion, and any other modified immunoglobulin molecule comprising an antigen recognition site. Furthermore, "monoclonal antibody" refers to such antibodies made in any number of ways including, but not limited to, by hybridoma, phage selection, recombinant expression, and transgenic animals (e.g., expression of a human antibody in a transgenic mouse).

The term "humanized antibody" refers to an antibody derived from a non-human (e.g., murine) immunoglobulin, which has been engineered to contain minimal non-human (e.g., murine) sequences. Typically, humanized antibodies are human immunoglobulins in which residues from the CDRs are replaced by residues from the CDRs of a non-human species (e.g., mouse, rat, rabbit, or hamster) that have the desired specificity, affinity, and capability (Jones et al., 1986, *Nature*, 321:522-525; Riechmann et al., 1988, *Nature*, 332:323-327; Verhoeyen et al., 1988, *Science*, 239:1534-1536). In some instances, the FW residues of a human immunoglobulin are replaced with the corresponding residues in an antibody from a non-human species that has the desired specificity, and/or affinity, and/or capability.

The term "antibody-drug conjugate" (ADC) refers to a conjugate comprising at least one antibody binding to an epitope of interest conjugated to least one compound of Formula I or compound of Formula II. Compounds of Formula I and compounds of Formula II may be conjugated to antibodies to form antibody drug conjugates. (ADC) whereby compounds of Formula I and compounds of Formula II, may serve as therapeutic moieties which are delivered to a therapeutic target of interest by the antibody to which they are conjugated.

In some aspects, the ADC comprises two, three, four, five, six, seven, eight, nine or ten therapeutic moieties. In some specific aspects, the ADC comprises two, three, or four therapeutic moieties. In some aspects, all therapeutic moieties are the same. In some aspects, at least one therapeutic moiety is different from the rest.

A therapeutic moiety refers to a single molecule of a compound of Formula I or a single molecule of a compound of Formula II.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

The term "pharmaceutical composition" refers to a preparation which is in such form as to permit the biological activity of the active ingredient, and which contains no additional components which are unacceptably toxic to a subject to which the composition would be administered. Such composition can be sterile.

Terms such as "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented. In certain aspects, a subject is successfully "treated" for cancer according to the methods of the present disclosure if the patient shows, e.g., total, partial, or transient remission of a certain type of cancer.

The terms "cancer", "tumor", "cancerous", and "malignant" refer to or describe the physiological condition in mammals that is typically characterized by unregulated cell growth. Examples of cancers include but are not limited to, carcinoma including adenocarcinomas, lymphomas, blastomas, melanomas, sarcomas, and leukemias. More particular examples of such cancers include squamous cell cancer, small-cell lung cancer, non-small cell lung cancer, gastrointestinal cancer, Hodgkin's and non-Hodgkin's lymphoma, pancreatic cancer, glioblastoma, glioma, cervical cancer, ovarian cancer, liver cancer such as hepatic carcinoma and hepatoma, bladder cancer, breast cancer (including hormonally mediated breast cancer, see, e.g., Innes et al. (2006) Br. J. Cancer 94:1057-1065), colon cancer, colorectal cancer, endometrial carcinoma, myeloma (such as multiple myeloma), salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, various types of head and neck cancer and cancers of mucinous origins, such as, mucinous ovarian cancer, cholangiocarcinoma (liver) and renal papillary carcinoma.

The term "cytotoxic agent" as used herein is defined broadly and refers to a substance that inhibits or prevents the function of cells and/or causes destruction of cells (cell death), and/or exerts anti-neoplastic/anti-proliferative effects. For example, cytotoxic agent prevents directly or indirectly the development, maturation, or spread of neoplastic tumor cells. The term includes also such agents that cause a cytostatic effect only and not a mere cytotoxic effect. The term includes chemotherapeutic agents as specified below, as well as other HER2 antagonists, antiangiogenic agents, tyrosine kinase inhibitors, protein kinase A inhibitors, members of the cytokine family, radioactive isotopes, and toxins such as enzymatically active toxins of bacterial, fungal, plant or animal origin.

The term "chemotherapeutic agent" is a subset of the term "cytotoxic agent" comprising natural or synthetic chemical compounds. Examples of chemotherapeutic or agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, Vinca alkaloids and derivatives of podophyllotoxin; cytotoxic antibiotics and camptothecin derivatives. Other chemotherapeutic agents are amifostine (ETHYOL®), cisplatin, dacarbazine (DTIC), dactinomycin, mechlorethamine (nitrogen mustard), streptozocin, cyclophosphamide, carmustine (BCNU), lomustine (CCNU), doxorubicin (ADRIAMYCIN®), doxorubicin lipo (DOXIL®), gemcitabine (GEMZAR®), daunorubicin, daunorubicin lipo (DAUNOXOME®), procarbazine, mitomycin, cytarabine, etoposide, methotrexate, 5-fluorouracil (5-FU), vinblastine, vincristine, bleomycin, paclitaxel (TAXOL®), docetaxel (TAXOTERE®), aldesleukin, asparaginase, busulfan, carboplatin, cladribine, camptothecin, CPT-11, 10-hydroxy-7-ethyl-camptothecin (SN38), gefitinib (IRESSA®), dacarbazine, floxuridine, fludarabine, hydroxyurea, ifosfamide, idarubicin, mesna, interferon alpha, interferon beta, irinotecan, mitoxantrone, topotecan, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil aromatase inhibitors, and combinations thereof.

In accordance with the methods of the present disclosure, compounds and ADCs of the present disclosure may be administered to a patient to promote a positive therapeutic response with respect to cancer. The term "positive therapeutic response" with respect to cancer treatment refers to an improvement in the symptoms associated with the disease.

For example, an improvement in the disease can be characterized as a complete response. The term "complete response" refers to an absence of clinically detectable disease with normalization of any previously test results. Alternatively, an improvement in the disease can be categorized as being a partial response. A "positive therapeutic response" encompasses a reduction or inhibition of the progression and/or duration of cancer, the reduction or amelioration of the severity of cancer, and/or the amelioration of one or more symptoms thereof resulting from the administration of compounds of the present disclosure.

In specific aspects, such terms refer to one, two or three or more results following the administration of compounds of the instant disclosure:
(1) a stabilization, reduction or elimination of the cancer cell population;
(2) a stabilization or reduction in cancer growth;
(3) an impairment in the formation of cancer;
(4) eradication, removal, or control of primary, regional and/or metastatic cancer;
(5) a reduction in mortality;
(6) an increase in disease-free, relapse-free, progression-free, and/or overall survival, duration, or rate;
(7) an increase in the response rate, the durability of response, or number of patients who respond or are in remission;
(8) a decrease in hospitalization rate,
(9) a decrease in hospitalization lengths,
(10) the size of the cancer is maintained and does not increase or increases by less than 10%, preferably less than 5%, preferably less than 4%, preferably less than 2%, and
(11) an increase in the number of patients in remission.
(12) a decrease in the number of adjuvant therapies (e.g., chemotherapy or hormonal therapy) that would otherwise be required to treat the cancer.

Clinical response can be assessed using screening techniques such as PET, magnetic resonance imaging (MRI) scan, x-radiographic imaging, computed tomographic (CT) scan, flow cytometry or fluorescence-activated cell sorter (FACS) analysis, histology, gross pathology, and blood chemistry, including but not limited to changes detectable by ELISA, RIA, chromatography, and the like. In addition to these positive therapeutic responses, the subject undergoing therapy can experience the beneficial effect of an improvement in the symptoms associated with the disease.

The compounds of the instant disclosure can be used in combination with any known therapies for cancer, including any agent or combination of agents that are known to be useful, or which have been used or are currently in use, for treatment of cancer, e.g., colon cancer, lung cancer, gastric cancer, head and neck squamous cells cancer, and breast cancer. Anticancer agents include drugs used to treat malignancies, such as cancerous growths. Drug therapy can be used alone, or in combination with other treatments such as surgery or radiation therapy. Several classes of drugs can be used in cancer treatment, depending on the nature of the organ involved. For example, breast cancers are commonly stimulated by estrogens, and can be treated with drugs which inactive the sex hormones. Similarly, prostate cancer can be treated with drugs that inactivate androgens, the male sex hormone.

Anti-cancer agents for use in certain methods of the present disclosure include, among others, antibodies, anti-metabolites, alkylating agents, topoisomerase inhibitors, microtubule targeting agents, kinase inhibitors, protein synthesis inhibitors, immunotherapeutic agents, hormonal therapies, glucocorticoids, aromatase inhibitors, mTOR inhibitors, chemotherapeutic agents, protein kinase B inhibitors, phosphatidylinositol 3-kinase (PI3K) inhibitors, cyclin dependent kinase (CDK) inhibitors, RLr9, CD289, enzyme inhibitors, anti-TRAIL, MEK inhibitors, and the like.

Where the combined therapies comprise administration compounds of the present disclosure in combination with administration of another therapeutic agent, the methods of the instant disclosure encompass co-administration, using separate formulations or a single pharmaceutical formulation, and consecutive administration in either order. In some aspects, the compounds of Formula I, compounds of Formula II, and/or ADCs described herein are administered in combination with other drugs, wherein the antibody or antigen-binding fragment, variant, or derivative thereof and the therapeutic agent(s) can be administered sequentially, in either order, or simultaneously (i.e., concurrently or within the same time frame).

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

Compounds and ADCs of the present disclosure (therapeutic agents) may be administered to a patient oral, parenteral, by inhalation or topical routes. The term parenteral as used herein includes, e.g., intravenous, intraarterial, intraperitoneal, intramuscular, subcutaneous, rectal, or vaginal administration. However, in other methods compatible with the teachings herein, ADC can be used to selectively target compounds of the present invention to deliver the therapeutic agents directly to the site of the adverse cellular population thereby increasing the exposure of the diseased tissue to the therapeutic agent.

As discussed herein, therapeutic agents of the present disclosure can be administered in a pharmaceutically acceptable composition for the in vivo treatment of cancers. Typically, compounds of the present disclosure will be formulated as solutions for intravenous administration or as lyophilized concentrates for reconstitution to prepare intravenous solutions (such as with saline, 5% dextrose, or similar isotonic solutions). The pharmaceutical compositions can comprise pharmaceutically acceptable carriers, including, e.g., water, ion exchangers, proteins, buffer substances, and salts. Preservatives and other additives can also be present. The carrier can be a solvent or dispersion medium. Suitable formulations for use in the therapeutic methods disclosed herein are described in Remington's Pharmaceutical Sciences (Mack Publishing Co.) 16th ed. (1980).

In any case, sterile injectable solutions can be prepared by incorporating therapeutic agents of the present disclosure in the required amount in an appropriate solvent followed by filtered sterilization. Further, the preparations can be packaged and sold in the form of a kit. Such articles of manufacture can have labels or package inserts indicating that the associated compositions are useful for treating a subject suffering from, or predisposed to a disease or disorder.

Parenteral formulations can be a single bolus dose, an infusion or a loading bolus dose followed with a maintenance dose. These compositions can be administered at specific fixed or variable intervals, e.g., once a day, or on an "as needed" basis.

The composition can be administered as a single dose, multiple doses or over an established period of time in an infusion. Dosage regimens also can be adjusted to provide the optimum desired response (e.g., a therapeutic or prophylactic response).

Therapeutically effective doses of the compositions of the present disclosure, for treatment of cancers including e.g., colon cancer, lung cancer, gastric cancer, head and neck squamous cells cancer, melanoma, pancreatic cancer, prostate cancer, and breast cancer, vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages can be titrated using routine methods known to those of skill in the art to optimize safety and efficacy.

The amount of therapeutic agent of the present disclosure to be administered can be readily determined by one of ordinary skill in the art without undue experimentation. Factors influencing the mode of administration and the respective amount of agent, include, but are not limited to, the severity of the disease, the history of the disease, and the age, height, weight, health, and physical condition of the individual undergoing therapy. Similarly, the amount of anti-HER2 binding molecule, e.g., antibody, or fragment, variant, or derivative thereof, to be administered will be dependent upon the mode of administration and whether the subject will undergo a single dose or multiple doses of this agent.

The present disclosure also provides for the use of a therapeutic agent of the disclosure, in the manufacture of a medicament for treating a type of cancer, including, e.g., breast cancer, colon cancer, lung cancer, gastric cancer, head and neck squamous cells cancer, melanoma, pancreatic cancer, and prostate cancer.

The disclosure also provides for the use of a therapeutic agent of the disclosure, in the manufacture of a medicament for treating a subject for treating a type of cancer. In certain aspects, the medicament is used in a subject that has been pretreated with at least one other therapy.

By "pretreated" or "pretreatment" is intended the subject has received one or more other therapies (e.g., been treated with at least one other anti-cancer therapy) prior to receiving the medicament comprising compounds of the instant disclosure. It is not necessary that the subject was a responder to pretreatment with the prior therapy or therapies. Thus, the subject that receives the medicament could have responded, or could have failed to respond to pretreatment with the prior therapy, or to one or more of the prior therapies where pretreatment comprised multiple therapies.

The instant disclosure also provides for the co-administration of the therapeutic agent and at least one other therapy, together in a single composition or co-administered together at the same time or overlapping times in separate compositions.

The instant disclosure also provides for the use of the therapeutic agent in the manufacture of a medicament for treating a subject for treating cancer, wherein the agent is administered before a subject has been treated with at least one other therapy.

EXAMPLES

Aspects of the present disclosure can be further defined by reference to the following non-limiting examples, which describe in detail preparation of certain compounds and intermediates of the present disclosure and methods for using compounds of the present disclosure. It will be apparent to those skilled in the art that many modifications, both to materials and methods, can be practiced without departing from the scope of the present disclosure.

Unless stated otherwise:
 (i) temperatures are given in degrees Celsius (° C.); when operations were carried out at room temperature or ambient temperature, that is, in a range of 18-25° C., unless otherwise stated;
 (ii) solutions were dried over anhydrous sodium sulphate or magnesium sulphate; evaporation organic of organic solvent was carried out using a rotary evaporator under reduced pressure (4.5-30 mmHg) with a bath temperature of up to 30° C.;
 (iii) chromatography means flash chromatography on silica gel; thin layer chromatography (TLC) was carried out on silica gel plates;
 (iv) in general, the course of reactions was followed by TLC or liquid chromatography/mass spectroscopy (LC/MS) and reaction times are given for illustration only;
 (v) final products have satisfactory proton nuclear magnetic resonance (NMR) spectra and/or mass spectra data;
 (vi) yields are given for illustration only and are not necessarily those which can be obtained by diligent process development; preparations were repeated if more material was required;
 (vii) when given, nuclear magnetic resonance (NMR) data is in the form of delta (□) values for major diagnostic protons, given in part per million (ppm) relative to tetramethylsilane (TMS) as an internal standard, determined at 300 or 400 MHz in $d_6$-DMSO unless otherwise stated;
 (viii) chemical symbols have their usual meanings;
 (ix) solvent ratio is given in volume:volume (v/v) terms;
 (x) purification of the compounds was carried out using one or more of the following methods:
  a) flash chromatography on regular silica gel;
  b) flash chromatography on silica gel using Isco Combiflash® separation system: RediSep normal phase flash column, flow rate, 30-40 ml/min (ISCO MPLC c) Gilson semiprep HPLC separation system: YMC pack ODS-AQ column, 100×20 mm, S 5 μm 12 nm, water (0.1% trifluoroacetic acid) and acetonitrile (0.1% trifluoroacetic acid) as solvents, 20 min; and
(xi) the following abbreviations have been used:
Boc t-Butoxycarbonyl;
DCM dichloromethane;
DIAD Diisopropyl azodicarboxylate;
DIC N,N'-diisopropylcarbodiimide;
DCC N,N'-dicyclohexylcarbodiimide;
DIEA diethylisopropylamine;
DMA N,N-dimethylacetamide;
DMF N,N-dimethylformamide;
EDCI 1-Ethyl-3-(3-dimethylaminopropyl)carbodiimide
EtOAc Ethyl acetate;
Et$_2$O Diethylether;
Fmoc-OSu 9-Fluorenylmethyl N-succinimidyl carbonate MeOH methanol;
Na$_2$CO$_3$ sodium carbonate;
NaHCO$_3$ sodium hydrogen carbonate;
RT room temperature;
TEA triethylamine
TFA trifluoroacetic acid;
THF tetrahydrofuran.
HATU 1-[Bis(dimethylamino)methylene]-1H-1,2,3-triazolo[4,5-b]pyridinium 3-oxid hexafluorophosphate
DAST Diethylaminosulfur trifluoride
ACN acetonitrile
Boc$_2$O di-tert-butyl dicarbonate
Meldrum's acid 2,2-dimethyl-1,3-dioxane-4,6-dione General Scheme for Synthesis of Compounds 1-5

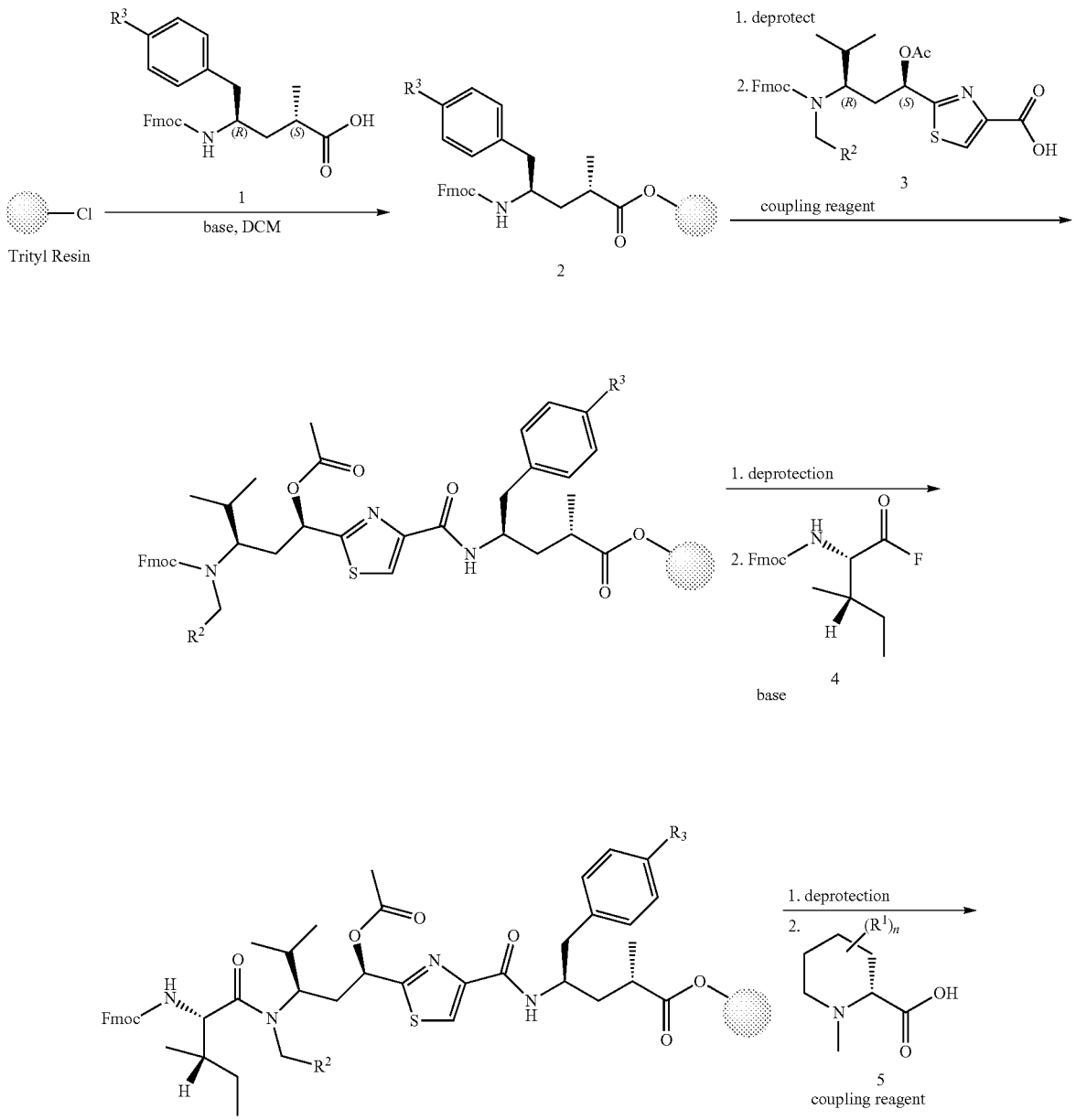

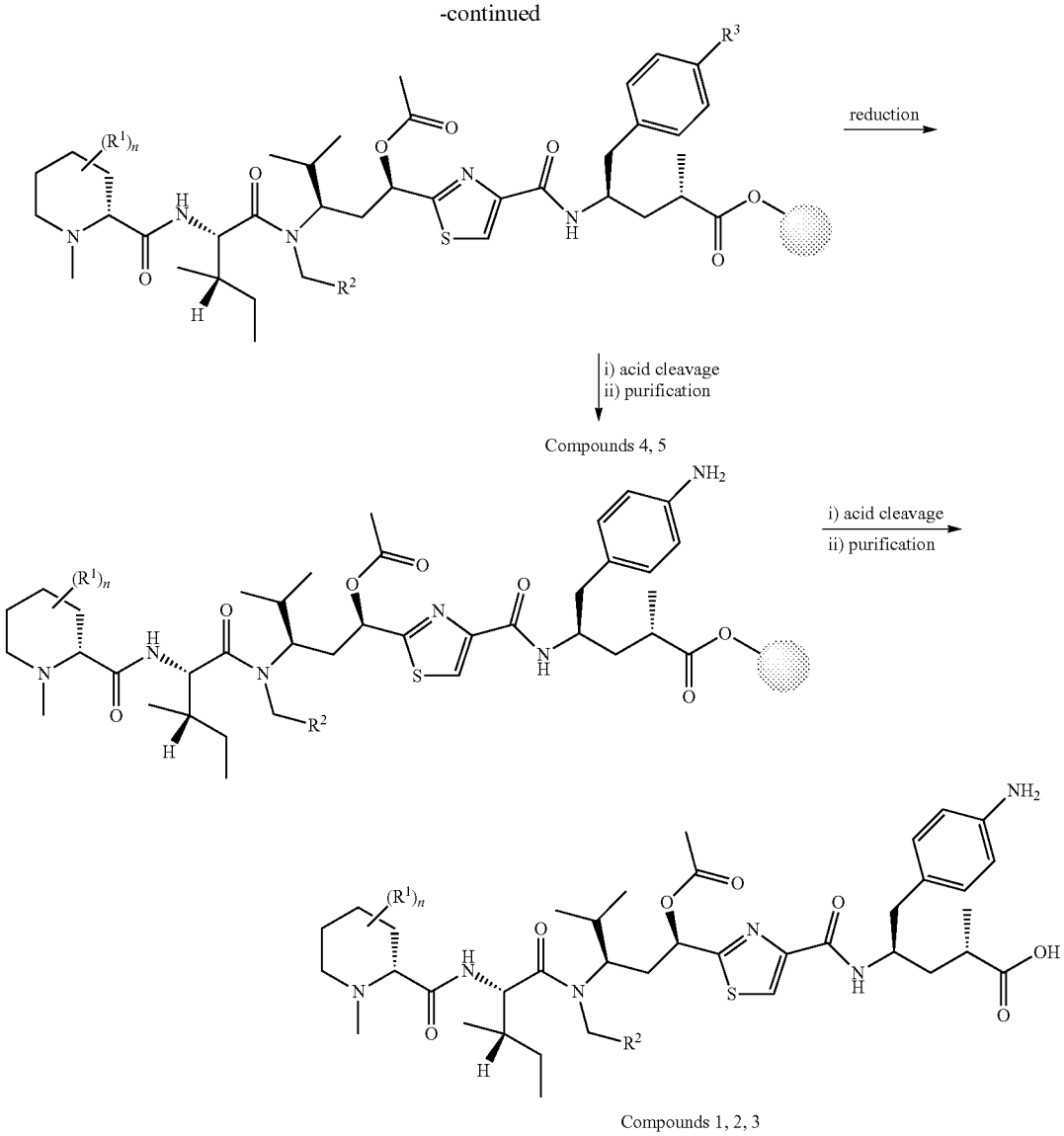

Compounds 1, 2, 3

Intermediate 1

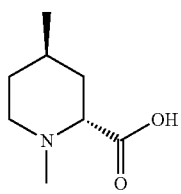

To a solution of (2R,4R)-4-methylpiperidine-2-carboxylic acid (2 g, 13.97 mmol) in MeOH (40 mL) and water (40.0 mL) was added paraformaldehyde (2.52 g, 27.94 mmol) and Pd/C (10%) (0.8 g, 7.52 mmol). The reaction mixture was stirred under a hydrogen atmosphere at room temperature overnight. From TLC, the reaction was not completed. Another one equivalent of paraformaldehyde (2.52 g, 27.94 mmol) was added and the reaction mixture was stirred another 24 hours. TLC indicated the reaction was completed and reaction mixture was filtered, washed the catalyst with MeOH (2×30 mL). The filtrate was concentrated in vacuo to give crude product as a white solid, which was washed with ether (3×30 mL), dried in high vacuum overnight to yield (2R,4R)-1,4-dimethylpiperidine-2-carboxylic acid (1) (1.870 g, 85%) as a white solid. LC-MS: 158 (M+1); $^1$H NMR (400 MHz, D$_2$O) δ ppm 0.97 (d, J=5.52 Hz, 3H), 1.54 (br. s, 1H), 1.71-1.87 (m, 3H), 1.91-2.07 (m, 1H), 2.84 (s, 3H), 3.13 (td, J=8.41, 3.76 Hz, 1H), 3.35 (m, 1H), 3.65 (m, 1H).

Intermediate 2

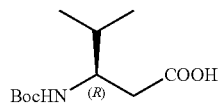

Boc₂O (243.0 g, 1.1 mol) was added dropwise to a suspension of (R)-3-amino-4-methyl pentanoic acid (commercially available) (133.0 g, 1.0 mol) and Na₂CO₃ (212 g, 2.0 mol) in acetone (1 L) and water (1 L) with stirring at room temperature. The reaction mixture was stirred overnight and the organic solvent was removed under reduced pressure. The residue was diluted with water (1 L) and washed with EtOAc (500 mL×3). The aqueous phase was acidified with 2N HCl solution to pH=3 and the resulting mixture was extracted with EtOAc (800 mL×3). The combined extracts were washed with brine (800 mL×1), dried (Na₂SO₄) and concentrated to give compound (2) (224.0 g, 97% yield) as an oil, which was used in the next step without further purification.

Intermediate 3

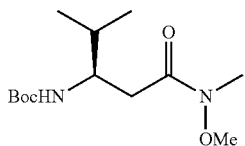 [SMILES: CON(C)C(=O)C[C@@H](NC(=O)OC(C)(C)C)C(C)C]

Triethylamine (67 g, 0.61 mol) was added to a suspension of Intermediate 2 (140.0 g, 0.61 mol) and N,O-dimethylhydroxylamine hydrochloride (74.1 g, 0.76 mol) in CH₂Cl₂ (1.4 L) with stirring at 0° C. The suspension was stirred for 0.5 hour and EDCI (74 g, 0.61 mol) was added in portions at 0° C. The reaction mixture was stirred for 2 hours at 0° C. and water (800 mL) was added. The organic phase was separated, washed with 5% KHSO₄ solution (800 mL×3), saturated NaHCO₃ solution (800 mL×3) and brine (800 mL×1), dried (Na₂SO₄) and concentrated to dryness. The residue was purified by flash column chromatography on silica gel (EtOAc/Hexane=1:5) to afford compound (3) (141.0 g, 84% yield) as an oil. ¹H NMR (300 MHz, CDCl3): δ 5.26 (m, 1H), 3.75 (m, 1H), 3.70 (s, 3H), 3.15 (s, 3H), 2.60~2.80 (m, 2H), 1.85 (m, 1H), 1.41 (s, 9H), 0.90 (d, J=6.6 Hz, 3H), 0.88 (d, J=6.6 Hz, 3H).

Intermediate 4

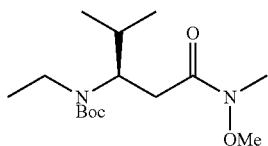 [SMILES: CCN(C(=O)OC(C)(C)C)[C@H](CC(=O)N(C)OC)C(C)C]

Iodoethane (250.0 g, 1.6 mol) was added to a solution of Intermediate 3 (55.0 g, 0.2 mol) in DMF (1.1 L) with stirring at 0° C. Then NaH (60% suspension, 24.0 g, 0.60 mol) was added in portions at 0° C. and the reaction mixture was allowed to warm to room temperature and stirred for 12 hours. The reaction was quenched with water (2 L) carefully and EtOAc (2 L) was added. The organic phase was separated, washed with 5% KHSO₄ solution (800 mL×3), saturated NaHCO₃ solution (800 mL×3) and brine (800 mL×1), dried (Na2SO4) and concentrated to dryness. The residue was purified by flash column chromatography on silica gel (EtOAc/Hexane=1:10) to afford tert-butyl (R)-ethyl(1-(methoxy(methyl)amino)-4-methyl-1-oxopentan-3-yl)carbamate (35.1 g, 58% yield) as an oil. ¹H NMR (300 MHz, CDCl3): δ 3.70 (s, 3H), 3.65 (m, 1H), 3.10~3.30 (m, 5H), 2.50~2.95 (m, 2H), 1.90~2.20 (m, 1H), 1.40~1.55 (m, 9H), 1.10 (t, J=7.2 Hz, 3H), 0.90 (d, J=6.6 Hz, 3H), 0.88 (d, J=6.6 Hz, 3H).

Intermediate 5

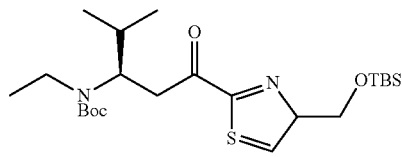

A solution of n-BuLi (106 ml, 2.5N in hexane, 0.17 mol) was added dropwise to a solution of Intermediate 50 (74 g, 0.24 mol) in dry THF (500 mL) at −78° C. under N₂ with stirring over 1 hour. The suspension was stirred for further 30 min and then a solution of Intermediate 4 (51.0 g, 0.17 mol) in dry THF (300 mL) was added dropwise over 30 min at −78° C. The reaction mixture was stirred for 1 hour at −78° C. and then allowed to warm to room temperature and stirred for 12 hours. The reaction was quenched with 20% aqueous ammonium chloride solution (1 L) and the organic solvent was removed under reduced pressure. The resulting mixture was extracted with EtOAc (800 mL×3). The combined organic phases were washed with 5% KHSO₄ solution (800 mL×3), saturated NaHCO₃ solution (800 mL×3) and brine (800 mL×1), dried (Na₂SO₄) and concentrated to dryness. The crude material was purified by flash column chromatography on silica gel (EtOAc/Hexane=1:10) to afford tert-butyl (R)-(1-(4-((((tert-butyldimethylsilyl)oxy)methyl)thiazol-2-yl)-4-methyl-1-oxopentan-3-yl)(ethyl)carbamate (58.1 g, 73% yield) as an oil. ¹H NMR (300 MHz, CDCl3): δ 7.53 (m, 1H), 4.90 (s, 2H), 4.04 (m, 1H), 3.35 (m, 2H), 3.15 (m, 2H), 2.00 (m, 1H), 1.40 (s, 9H), 0.80~1.20 (m, 18H), 0.14 (s, 6H).

Intermediate 6

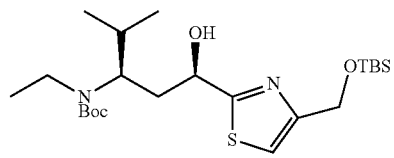 [SMILES: CCN(C(=O)OC(C)(C)C)[C@H](C[C@@H](O)c1nc(CO[Si](C)(C)C(C)(C)C)cs1)C(C)C]

LiBH₄ (4.8 g, 0.22 mol) was added in portions to a solution of Intermediate 5 (47.1 g, 0.1 mol) in methanol (500 mL) at room temperature over a period of 0.5 hour with stirring. The suspension was stirred for 2 hours and the solvent was removed under reduced pressure. The residue was dissolved in EtOAc (800 mL) and the resulting solution was washed with saturated NaHCO₃ solution (500 mL×3) and brine (500 mL×1), dried (Na₂SO₄) and concentrated to dryness. The crude material was purified by flash column chromatography (EtOAc/Hexane=1:6) to afford tert-butyl ((1R,3R)-1-(4-(((tert-butyldimethylsilyl)oxy)methyl)thiazol-2-yl)-1-hydroxy-4-methylpentan-3-yl)(ethyl)carbamate (13.5 g, 28% yield) and its isomer (6') (21.0 g, 45% yield). ¹H NMR (300 MHz, CDCl₃) δ ppm −0.06-0.05 (m, 6H) 0.76-0.89 (m, 15H) 1.12 (t, J=6.97 Hz, 3H) 1.39 (s, 9H)

1.55-2.05 (m, 3H) 2.86-3.21 (m, 2H) 3.76-3.96 (m, 1H) 4.73 (d, J=1.13 Hz, 4H) 7.01 (s, 1H).

Intermediate 7

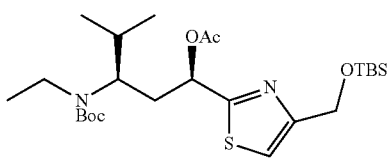 [SMILES: CCN(C(=O)OC(C)(C)C)[C@H](C[C@@H](OC(C)=O)c1nc(CO[Si](C)(C)C(C)(C)C)cs1)C(C)C]

Acetyl chloride (45.2 g, 0.58 mol) was added dropwise to a solution of Intermediate 6 (34.0 g, 72 mmol) in pyridine (500 mL) at 0° C. with stirring over 10 min. The reaction mixture was allowed to warm to room temperature and stirred for 12 hours. The reaction was quenched with water (200 mL) and the solvent was removed under reduced pressure. The residue was treated with $CH_2Cl_2$ (800 mL) and the resulting mixture was washed with 5% $KHSO_4$ solution (800 mL×3), saturated $NaHCO_3$ solution (800 mL×3) and brine (800 mL×1), dried ($Na_2SO_4$) and concentrated to dryness. The crude material was purified by flash column chromatography on silica gel (EtOAc/Hexane=1:10) to afford (1R,3R)-3-((tert-butoxycarbonyl)(ethyl)amino)-1-(4-(((tert-butyldimethylsilyl)oxy)methyl)thiazol-2-yl)-4-methylpentyl acetate (25.7 g, 69% yield) as an oil. $^1$H NMR (300 MHz, CDCl3): δ 7.15 (m, 1H), 5.95 (m, 1H), 4.84 (s, 2H), 4.04 (m, 1H), 3.10 (m, 2H), 2.35 (m, 1H), 2.15 (s, 3H), 2.00 (m, 1H), 1.70 (m, 1H), 1.45 (s, 9H), 1.25 (t, J=7.2 Hz, 3H), 0.80~1.10 (m, 15H), 0.08 (s, 6H).

Intermediate 8

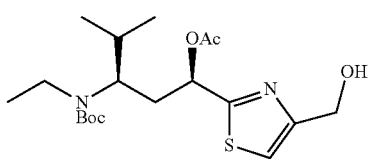 [SMILES: CCN(C(=O)OC(C)(C)C)[C@H](C[C@@H](OC(C)=O)c1nc(CO)cs1)C(C)C]

A solution of tetrabutylammonium fluoride (65.3 g, 0.25 mol) in THF (200 mL) was added dropwise to a solution of Intermediate 7 (25.7 g, 50 mmol) in THF (300 mL) at 0° C. with stirring. The reaction mixture was allowed to warm to room temperature and stirred for 4 hours. Water (800 mL) was added and the organic solvent was removed under reduced pressure. The residue was treated with $CH_2Cl_2$ (800 mL) and the resulting mixture was washed with 5% $KHSO_4$ solution (800 mL×3), saturated $NaHCO_3$ solution (800 mL×3) and brine (800 mL×1), dried (Na2SO4) and concentrated to dryness. The crude material was purified by flash column chromatography on silica gel (EtOAc/Hexane=1:4) to afford (1R,3R)-3-((tert-butoxycarbonyl)(ethyl)amino)-1-(4-(hydroxymethyl)thiazol-2-yl)-4-methylpentyl acetate (19.5 g, 98% yield) as an oil. 1H NMR (300 MHz, CDCl3): δ 8.26 (m, 1H), 5.95 (m, 1H), 4.83 (m, 2H), 4.10 (m, 1H), 3.17 (m, 2H), 2.40 (m, 1H), 2.20 (s, 3H), 2.18 (m, 1H), 1.75 (m, 1H), 1.56 (s, 9H), 1.10~1.30 (m, 3H), 0.80~1.05 (m, 6H).

Intermediate 9

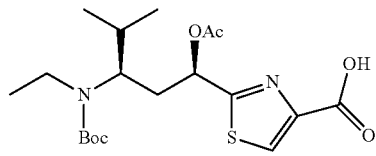 [SMILES: CCN(C(=O)OC(C)(C)C)[C@H](C[C@@H](OC(C)=O)c1nc(C(=O)O)cs1)C(C)C]

Dess-Martin reagent (32.7 g, 75 mmol) was added to a solution of Intermediate 8 (20.0 g, 50 mmol) in dichloromethane (300 mL) and the reaction mixture was stirred at room temperature for 12 hours. The mixture was washed with sodium hydroxide solution (1N, 300 mL×3), sodium thiosulfate solution (1N, 300 mL×3), saturated $NaHCO_3$ (300 mL×3) solution and brine (300 mL×1), respectively. The organic layer was dried ($Na_2SO_4$) and concentrated to dryness to give the corresponding aldehyde. This crude aldehyde was dissolved in tert-butyl alcohol (500 mL) and a solution of sodium chlorite (80%, 36.4 g, 320 mmol) and sodium dihydrogenphosphate monohydrate (105 g, 0.77 mol) in water (300 mL) was added dropwise over 1 hour at room temperature. The reaction mixture was stirred for 3 hours and diluted with hydrochloric acid solution (0.1N, 500 mL). The resulting mixture was extracted with EtOAc (500 mL×1) and the combined organic layers were washed with 5% $KHSO_4$ solution (500 mL×3) and brine (500 mL×1), dried over $Na_2SO_4$ and concentrated to dryness. The residue was purified by flash column chromatography on silica gel ($CH_2Cl_2$/MeOH=100:5) to afford 2-((1R,3R)-1-acetoxy-3-((tert-butoxycarbonyl)(ethyl)amino)-4-methylpentyl)thiazole-4-carboxylic acid (15.4 g, 58% yield). $^1$H NMR (300 MHz, CDCl$_3$): δ 9.90 (br s, 1H), 8.27 (s, 1H), 5.96 (m, 1H), 4.07 (m, 1H), 3.15 (m, 1H), 2.35 (m, 1H), 2.20 (s, 3H), 2.18 (m, 1H), 1.75 (m, 1H), 1.45 (s, 9H), 1.20 (t, J=7.2 Hz, 3H), 0.98 (d, J=6.6 Hz, 3H), 0.88 (d, J=6.6 Hz, 3H).

Intermediate 10

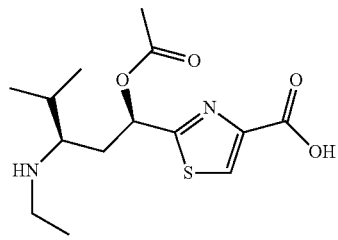 [SMILES: CCN[C@H](C[C@@H](OC(C)=O)c1nc(C(=O)O)cs1)C(C)C]

To the solution of Intermediate 9 (6.5 g, 15.68 mmol) in DCM (60 mL) was added TFA (30 mL) in dropwise at 0° C. The mixture was stirred at 0° C. for 1 hour. The solvent was evaporated in vacuo to give crude 2-((1R,3R)-1-acetoxy-3-(ethylamino)-4-methylpentyl)thiazole-4-carboxylic acid. The crude product was used to next step reaction without further purification (7.2 grams). LC-MS: 315 (M+1),

Intermediate 11

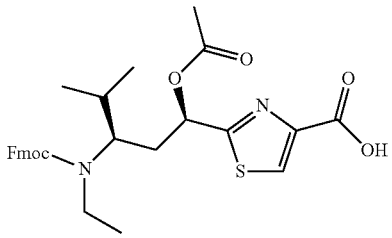

To the solution of Intermediate 10 (5 g, 11.67 mmol) and sodium bicarbonate (9.80 g, 116.71 mmol) in a mixture of acetone (300 mL) and water (150 mL) was added (9H-fluoren-9-yl)methyl (2,5-dioxopyrrolidin-1-yl) carbonate (3.94 g, 11.67 mmol). The mixture was stirred at room temperature for overnight. LCMS indicated the reaction was completed. The mixture was acidified to (pH 2) with hydrochloric acid and acetone was evaporated in vacuo. The product was extracted with DCM (3×300 mL). The combined organic extracts were washed with 0.1% HCl solution (200 mL), brine (200 mL), dried over $Na_2SO_4$, and evaporated in vacuo. The residue was purified by flash chromatography (silica gel, MeOH/DCM, MeOH from 0% to 5%) to give 2-((1R,3R)-3-((((9H-fluoren-9-yl)methoxy)carbonyl)(ethyl)amino)-1-acetoxy-4-methylpentyl)thiazole-4-carboxylic acid (3.53 g, 54.6%) as a white solid. LC-MS: 537.2 (M+1); $^1H$ NMR (400 MHz, CHLOROFORM-d) δ ppm 0.84 (d, J=6.78 Hz, 3H), 0.92-1.05 (m, 5H), 1.14 (d, J=3.01 Hz, 1H), 1.73 (dt, J=10.23, 6.43 Hz, 1H), 1.92-2.05 (m, 1H), 2.12-2.27 (m, 4H), 2.28-2.44 (m, 1H), 2.90-3.33 (m, 2H), 3.98 (t, J=9.29 Hz, 1H), 4.12-4.32 (m, 1H), 4.47-4.82 (m, 2H), 5.95 (dd, J=10.92, 2.89 Hz, 1H), 7.29-7.45 (m, 4H), 7.55-7.69 (m, 2H), 7.72-7.81 (m, 2H), 8.22-8.29 (m, 1H).

Intermediate 12

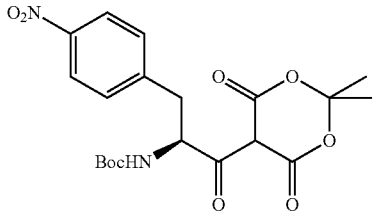 [SMILES: CC(C)(C)OC(=O)N[C@@H](Cc1ccc([N+](=O)[O-])cc1)C(=O)C1C(=O)OC(C)(C)OC1=O]

DMAP (106 g, 0.86 mol) was added to a solution of Boc-L-4-nitro-Phenylalanine (1800 g, 0.58 mol) and Meldrum's acid (92 g, 0.64 mol) in dichloromethane (1.5 L). The resulting solution was cooled at −5° C. under N2 atmosphere, followed by addition of DCC (240 g, 1.16 mol) in dichloromethane (1 L) over 1 h. The mixture was stirred overnight at 0~5° C. Then the precipitated N, N'-dicyclohexylurea was removed by filtration and the filtrate was washed with 5% aqueous HCl (1 L×3), and brine (1 L×1), and was dried over $MgSO_4$. After removal of $MgSO_4$ by filtration, the organic phase was concentrated to dryness. The residue was triturated with EtOAc/hexane (1:1, 500 mL), and was dried to afford tert-butyl (S)-(1-(2,2-dimethyl-4,6-dioxo-1,3-dioxan-5-yl)-3-(4-nitrophenyl)-1-oxopropan-2-yl)carbamate (130.0 g, 51% yield) as a yellow solid.

Intermediate 13

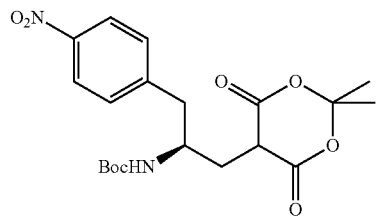 [SMILES: CC(C)(C)OC(=O)N[C@@H](Cc1ccc([N+](=O)[O-])cc1)CC1C(=O)OC(C)(C)OC1=O]

AcOH (400 mL) was added to a solution of Intermediate 12 (130.0 g, 0.298 mol) in dichloromethane (1.5 L) at −5° C. under $N_2$. Solid $NaBH_4$ (22.7 g, 0.597 mol) was added in small portions over 2 hours (gas evolution and exothermic). After stirring for additional 3 h at −5° C., TLC indicated the reaction was complete. The mixture was quenched with brine (1 L). The organic layer was separated, and was washed sequentially with water (1 L×2), aqueous saturated $NaHCO_3$ (1 L×3) and brine (1 L×3), and was dried over $MgSO_4$. The filtrate was concentrated to dryness and afford tert-butyl (R)-(1-(2,2-dimethyl-4,6-dioxo-1,3-dioxan-5-yl)-3-(4-nitrophenyl)propan-2-yl)carbamate (70.3 g, 55% yield) as a yellow solid. $^1H$ NMR (300 MHz, CDCl3): δ 8.18 (d, J=8.7 Hz, 2H), 7.41 (d, J=8.7 Hz, 2H), 4.58 (m, 1H), 4.29 (m, 1H), 3.85 (m, 1H), 2.97 (d, J=6.6 Hz, 2H), 2.27 (m, 2H), 1.80 (s, 3H), 1.76 (s, 3H), 1.35 (s, 9H).

Intermediate 14

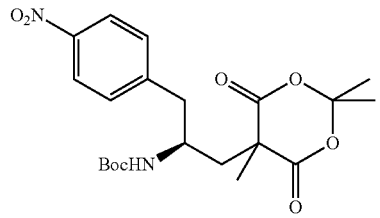 [SMILES: CC(C)(C)OC(=O)N[C@@H](Cc1ccc([N+](=O)[O-])cc1)CC1(C)C(=O)OC(C)(C)OC1=O]

$K_2CO_3$ (35 g, 0.25 mol) and MeI (36 g, 0.25 mol) were added to a solution of Intermediate 13 (70.3 g, 0.167 mol) in acetone (400 mL) and DMF (400 mL). The mixture was stirred overnight at room temperature. TLC showed the starting material was consumed. Water (2 L) was added and the mixture was stirred for an additional hour. The precipitated solid was collected by filtration, was washed with water, was dried to afford tert-butyl (S)-(1-(4-nitrophenyl)-3-(2,2,5-trimethyl-4,6-dioxo-1,3-dioxan-5-yl)propan-2-yl)carbamate (34.5 g, 47% yield) as a pale yellow solid. $^1H$ NMR (300 MHz, CDCl3): δ 8.17 (d, J=8.7 Hz, 2H), 7.34 (d, J=8.7 Hz, 2H), 4.22 (m, 1H), 3.85 (m, 1H), 2.85 (m, 2H), 2.22 (m, 2H), 1.73 (s, 3H), 1.73 (s, 3H), 1.52 (s, 3H), 1.31 (s, 9H).

Intermediate 15

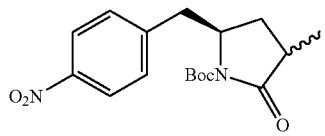 [SMILES: CC1C[C@H](Cc2ccc([N+](=O)[O-])cc2)N(C(=O)OC(C)(C)C)C1=O]

Intermediate 14 (34.5 g, 79.1 mmol) was dissolved in toluene (500 mL). The solution was heated under reflux for 40 hours. TLC indicated the reaction complete. The solvent was removed to afford tert-butyl (5R)-3-methyl-5-(4-nitrobenzyl)-2-oxopyrrolidine-1-carboxylate (30 g), which was used for next step without further purification.

Intermediate 16

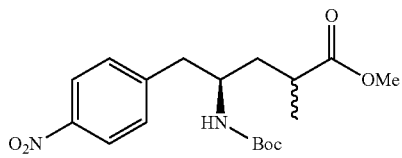 [SMILES: COC(=O)C(C)C[C@H](Cc1ccc([N+](=O)[O-])cc1)NC(=O)OC(C)(C)C]

$K_2CO_3$ (22 g, 0.16 mol) was added to a solution of Intermediate 15 (30 g, 79 mmol) in MeOH (300 mL). The mixture was stirred for 3 hours at room temperature. TLC showed complete conversion. The solvent was removed, the residue was dissolved in dichloromethane (500 mL), washed with brine (500 mL×3), and was dried over $MgSO_4$. After removal of $MgSO_4$ by filtration, the organic phase was concentrated to dryness. The residue was further purified by silica gel chromatography (EtOAc/Hexane=1:10) and afforded methyl (4R)-4-((tert-butoxycarbonyl)amino)-2-methyl-5-(4-nitrophenyl)pentanoate (23.5 g, 81% yield for two steps) as 1:1 diastereomeric mixture. $^1$H NMR (300 MHz, CDCl3): δ 8.13 (d, J=8.7 Hz, 2H), 7.34 (d, J=8.7 Hz, 2H), 4.43 (m, 1H), 3.85 (m, 1H), 3.65 (s, 3H), 2.85 (m, 2H), 2.65 (m, 1H), 1.85 (m, 1H), 1.50 (m, 1H), 1.30 (s, 9H), 1.15 (t, J=6.6 Hz, 3H).

Intermediate 17

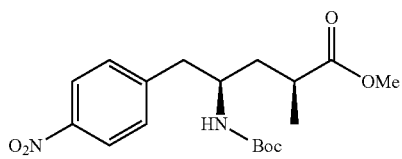 [SMILES: COC(=O)[C@@H](C)C[C@H](Cc1ccc([N+](=O)[O-])cc1)NC(=O)OC(C)(C)C]

50 g of compound (16) was subjected to chiral chromatography using SFC (supercritical fluid chromatography) on a Chiralpak ID 21×250 mm, 5 n column using mobile phase A 90% carbon dioxide and phase B isopropanol 10% at a 60 ml/min flow rate. The separation was performed at 40° C. and detection at 270 nM. Baseline separation was achieved and two fractions were isolated. Peak B was desired methyl (2S,4R)-4-((tert-butoxycarbonyl)amino)-2-methyl-5-(4-nitrophenyl)pentanoate and was obtained as a solid 27.4 g (55%). >99:1 diastereomeric excess on a Chiralpak IA column 4.6×250 mm, 5μ, 10% 1:1 Methanol:Isopropanol in hexane with 0.1% diethylamine modifier. LC/MS (2 minute, Acid_CV10.olp method 367 (M+1), 1.16 minutes. $^1$H NMR (400 MHz, METHANOL-$d_4$) δ ppm 8.16 (d, J=8.53 Hz, 2H) 7.46 (d, J=8.53 Hz, 2H) 3.79-3.93 (m, 1H) 3.68 (s, 3H) 2.90-2.99 (m, 1H) 2.71-2.81 (m, 1H) 2.47-2.59 (m, 1H) 1.81-1.95 (m, 1H) 1.55-1.66 (m, 1H) 1.32 (s, 9H) 1.21-1.25 (m, 2H) 1.16 (d, J=7.03 Hz, 3H)

Intermediate 18

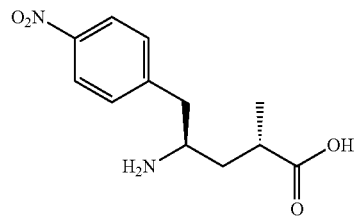 [SMILES: C[C@@H](C[C@@H](N)Cc1ccc([N+](=O)[O-])cc1)C(=O)O]

A solution of Intermediate 17 in 6N HCl aqueous solution (8.0 mL, 263.30 mmol) was heated at 130° C. in microwave for 30 min. The reaction mixture was lyophilized to afford (2S,4R)-4-amino-2-methyl-5-(4-nitrophenyl)pentanoic acid as a solid. The product was used to next step reaction without further purification (3.2 g). LC-MS: 253 (M+1); $^1$H NMR (400 MHz, $D_2O$) δ ppm 1.12 (d, J=7.28 Hz, 3H), 1.62-1.76 (m, 1H), 1.90-2.02 (m, 1H), 2.56-2.68 (m, 1H), 3.02-3.11 (m, 2H), 3.58-3.69 (m, 1H), 7.47 (d, J=8.53 Hz, 2H), 8.18 (d, J=8.78 Hz, 2H).

Intermediate 19

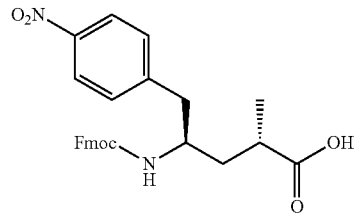

To the solution of Intermediate 18 (0.43 g, 1.49 mmol) and $NaHCO_3$ (1.251 g, 14.89 mmol) in a mixture of acetone (30 mL) and water (15 mL) was added (9H-fluoren-9-yl)methyl 2,5-dioxopyrrolidin-1-yl carbonate (0.502 g, 1.49 mmol). The mixture was stirred at room temperature for overnight. LC/MS indicated the reaction was completed. The mixture was acidified to pH 2 with hydrochloric acid and acetone was evaporated in vacuo. The product was extracted with DCM (3×60 mL). The combined organic extractes were washed with 1N HCl solution (40 mL), brine (40 mL), dried over $Na_2SO_4$, and evaporated in vacuo. The residue was purified by silica gel fish chromatography (EtOAc from 0% to 100% in DCM) to afford (2S,4R)-4-(((9H-fluoren-9-yl)methoxy)carbonylamino)-2-methyl-5-(4-nitrophenyl)pentanoic acid (0.630 g, 89%) as a white solid. LC-MS: 475.5 (M+H); $^1$H NMR (400 MHz, CHLOROFORM-d) δ ppm 0.81-1.06 (m, 1H), 1.08-1.28 (m, 2H), 1.33-1.75 (m, 1H), 1.77-2.11 (m, 1H), 2.36-2.69 (m, 2H), 2.76-3.18 (m, 1H), 3.43-4.08 (m, 1H), 4.09-4.19 (m, 1H), 4.21-4.53 (m, 2H), 4.54-4.80 (m, 1H), 7.18-7.58 (m, 8H), 7.66-7.82 (m, 2H), 7.95-8.17 (m, 2H), 8.67 (br. s., 1H).

Intermediate 20

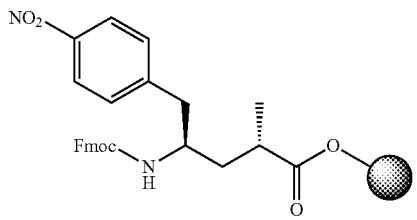

DIEA (0.419 mL, 2.40 mmol) was added to a solution of Intermediate 19 (0.380 g, 0.80 mmol) in DCM (4.5 mL), and the mixture was stirred at room temperature for 5 min, then 2-Chlorotrityl chloride resin (0.4 mmol/g loading, 0.5 g, 0.80 mmol) was added to the mixture. The mixture was shaken at room temperature for overnight, the resulting resin was washed with DMF (3×6 mL), MeOH (3×6 mL), and DCM (3×6 mL), then was treated with DIEA (0.419 mL, 2.40 mmol) and MeOH/DCM (1:1, 5 mL) at room temperature for 30 min. Resulting resin was filtered, washed with DMF (3×6 mL), MeOH (3×6 mL), and DCM (3×6 mL), was dried in high vacuum overnight. Small amount of compound was cleaved from resin, and analyzed by LC/MS. The resulting resin was used for next step reaction. LC/MS: 475 (M+1).

Intermediate 21

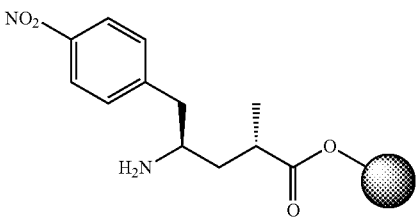 [SMILES: COC(=O)[C@@H](C)C[C@@H](N)Cc1ccc([N+](=O)[O-])cc1]

To the resin Intermediate 20 (0.5 g, 0.80 mmol) was added 20% piperidine in DMF (5 mL). The mixture was shaken at room temperature for 6 min, the resulting resin was filtered, washed with DMF (3×6 mL), MeOH (3×6 mL), DCM (3×6 mL), and was dried in vacuo. Small amount of the compound was cleaved from resin, analyzed by LC/MS, which indicated the reaction was completed. The resulting resin was used for the next step reaction. LC/MS: 253 (M+H).

Intermediate 22

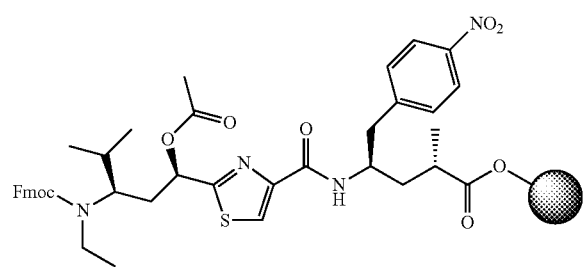

To the intermediate 21 resin (0.5 g, 1.88 mmol) was added a solution of Intermediate 11 (1.108 g, 2.07 mmol), HATU (1.428 g, 3.76 mmol), 2,4,6-trimethylpyridine (0.500 mL, 3.76 mmol), and DIEA (0.656 mL, 3.76 mmol) in DMF (5 mL) at room temperature. The mixture was shaken at room temperature for two hours, and the resulting resin was filtered, washed with DMF (3×6 mL), MeOH (3×6 mL), and DCM (3×6 mL), and was dried in vacuo. Small amount of the compound was cleaved from resin, analyzed by LC/MS, which indicated the reaction was complete. The resulting resin was used for the next step. LC/MS: 771 (M+H).

Intermediate 23

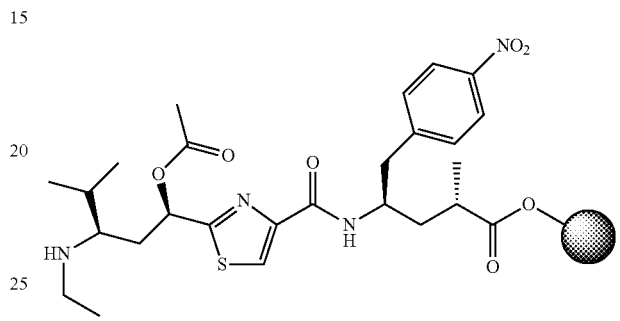

To the intermediate 22 resin (0.5 g, 0.80 mmol) was added 20% piperidine in DMF (5 mL). The mixture was shaken at room temperature for 6 min, the resulting resin was filtered, washed with DMF (3×6 mL), MeOH (3×6 mL), DCM (3×6 mL), and was dried in vacuo. Small amount of the compound was cleaved from resin, analyzed by LC/MS that indicated the reaction was complete. The resulting resin was used to next step reaction. LC-MS: 549 (M+1).

Intermediate 24

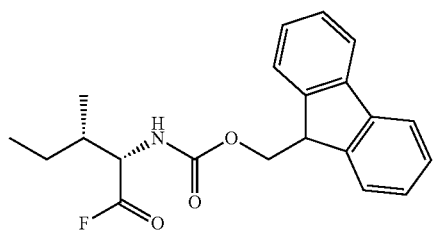 [SMILES: CC[C@H](C)[C@H](NC(=O)OCC1c2ccccc2-c2ccccc21)C(=O)F]

To a solution of (2S,3S)-2-(((9H-fluoren-9-yl)methoxy)carbonylamino)-3-methylpentanoic acid (Fmoc-Isoleucine) (7 g, 19.81 mmol) and pyridine (1.602 mL, 19.81 mmol) in DCM (120 mL) was added via cannula a solution of DAST (3.11 mL, 23.77 mmol) in DCM (20 mL) over 10 min. The reaction mixture was stirred at room temperature for 1 hour, diluted with DCM (80 mL), washed with ice-cold water (2×200 mL), the organic layer was dried over MgSO4, filtered, and evaporated in vacuo to give (9H-fluoren-9-yl)methyl (2S,3S)-1-fluoro-3-methyl-1-oxopentan-2-ylcarbamate (6.65 g, 94%) as a white solid. An esterification test was performed to assure quantitative acid fluoride formation by dissolving Fmoc-Ile-F (5 mg) in anhydrous MeOH (0.3 mL) and DIEA (0.030 mL) and allowing to react at room temperature for 15 min. The mixture was then evaporated in vacuo and analyzed by LCMS, showed less than 1% of Fmoc-Ile-OH present.

¹H NMR (400 MHz, CDCl₃) δ ppm 0.83-1.12 (m, 6H) 1.18-1.37 (m, 1H) 1.42-1.59 (m, 1H) 2.01 (br. s., 1H) 4.26 (t, J=6.78 Hz, 1H) 4.44-4.63 (m, 3H) 5.20 (d, J=8.53 Hz, 1H) 7.31-7.39 (m, 2H) 7.40-7.47 (m, 2H) 7.61 (d, J=7.28 Hz, 2H) 7.80 (d, J=7.53 Hz, 2H)

Intermediate 25

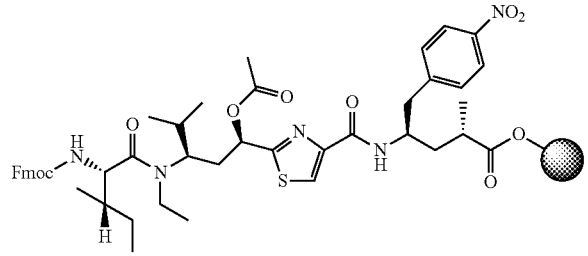

To the intermediate 23 resin (0.5 g, 0.80 mmol) was added a solution of intermediate 24 (0.569 g, 1.60 mmol), DMAP (4.89 mg, 0.04 mmol), and DIEA (0.419 mL, 2.40 mmol) in DCM (5 mL) at room temperature. The mixture was shaken at room temperature for overnight, the resulting resin was filtered, washed with DMF (3×6 mL), MeOH (3×6 mL), DCM (3×6 mL), dried in high vacuum. Small amount of compound was cleaved from resin, and analyzed by LC/MS. LC/MS indicated the reaction was completed. The resulting resin was used to next step reaction. LC-MS: 884 (M+H).

Intermediate 26

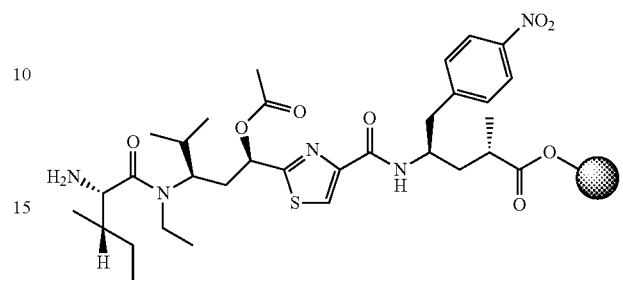

To the intermediate 25 resin (0.5 g, 0.80 mmol) was added 20% piperidine in DMF (5 mL). The mixture was shaken at room temperature for 6 min, the resulting resin was filtered, washed with DMF (3×6 mL), MeOH (3×6 mL), DCM (3×6 mL), and was dried in vacuo. Small amount of the compound was cleaved from resin, was analyzed by LC/MS, which indicated the reaction was complete. The resulting resin was used to next step reaction. LC/MS: 662 (M+1).

Intermediate 27

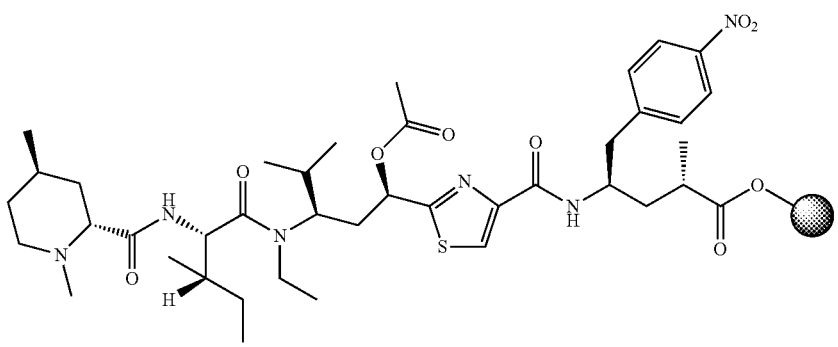 [SMILES: CC[C@H](C)[C@H](NC(=O)[C@H]1C[C@H](C)CCN1C)C(=O)N(CC)[C@H](C[C@@H](OC(C)=O)c1nc(C(=O)N[C@@H](Cc2ccc([N+](=O)[O-])cc2)C[C@H](C)C(=O)OC)cs1)C(C)C]

To the resin intermediate 26 (0.5 g, 0.80 mmol) was added a solution of Intermediate 1 (0.252 g, 1.60 mmol), HATU (0.608 g, 1.60 mmol), 2,4,6-trimethylpyridine (0.320 mL, 2.40 mmol), and DIEA (0.419 mL, 2.40 mmol) in DMF (5 mL). The mixture was shaken at room temperature for 2 hours, the resulting resin was filtered, washed with DMF (3×6 mL), MeOH (3×6 mL), and DCM (3×6 mL), and was dried in vacuo. Small amount of the compound was cleaved from resin, analyzed by LC/MS, which indicated the reaction was complete. The resulting resin was used to next step reaction. LC-MS: 801 (M+1).

Intermediate 28

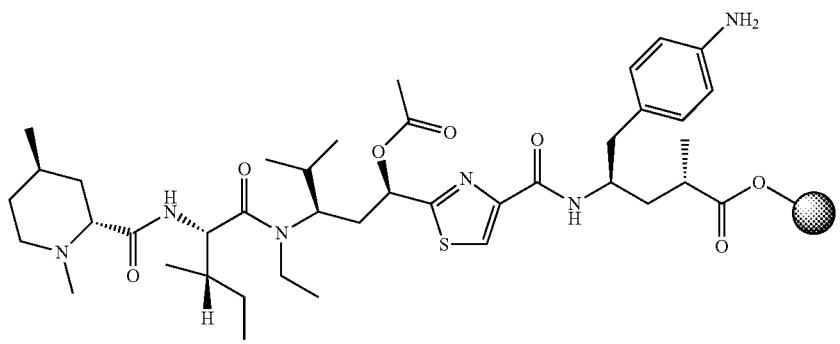 [SMILES: CC[C@H](C)[C@H](NC(=O)[C@H]1C[C@H](C)CCN1C)C(=O)N(CC)[C@H](C[C@@H](OC(C)=O)c1nc(C(=O)N[C@@H](Cc2ccc(N)cc2)C[C@H](C)C(=O)OC)cs1)C(C)C]

To the resin intermediate 27 was added a solution of tin(II) chloride dehydrate (1.805 g, 8.00 mmol), and sodium acetate (0.197 g, 2.40 mmol) in DMF (5 mL). The mixture was shaken at room temperature for 4 hours. The resulting resin was filtered, washed with DMF (3×6 mL), MeOH (3×6 mL), and DCM (3×6 mL), and was dried in vacuo. Small amount of the compound was cleaved from resin, and was analyzed by LCMS, which indicated the reaction was complete. The resulting resin was used for the next step. LC-MS: 771 (M+H).

Compound 1

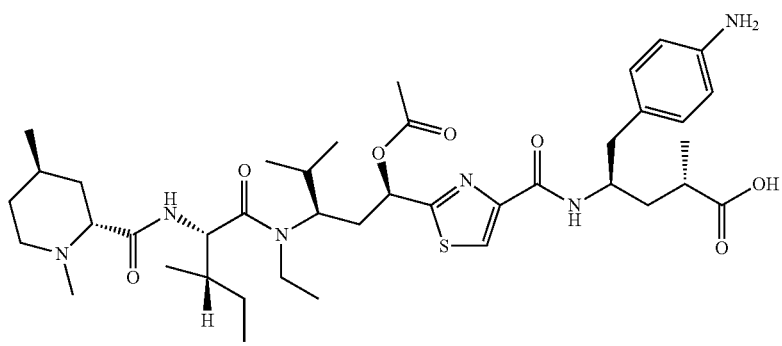 [SMILES: CC[C@H](C)[C@H](NC(=O)[C@H]1C[C@H](C)CCN1C)C(=O)N(CC)[C@H](C[C@@H](OC(C)=O)c1nc(C(=O)N[C@@H](Cc2ccc(N)cc2)C[C@H](C)C(=O)O)cs1)C(C)C]

To the resin intermediate 28 (0.1 g, 0.16 mmol) was added DCM (1 mL), water (0.200 mL) and TFA (1 mL) at room temperature. The mixture was shaken at room temperature for 20 min, then was filtered, and the resin was washed with water/TFA (1:1, 3×2 mL), and the filtrate was evaporated in vacuo. The residue was purified by reverse phase HPLC (ACN/H$_2$O 0.1% TFA, ACN from 5% to 50% in 14 min). The pure fractions were lyophilized to give (2S,4R)-4-(2-(((1R,3R)-1-acetoxy-3-((2S,3S)-2-((2R,4R)-1,4-dimethylpiperidine-2-carboxamido)-N-ethyl-3-methylpentanamido)-4-methylpentyl)thiazole-4-carboxamido)-5-(4-aminophenyl)-2-methylpentanoic acid (0.050 g, 35.3%) as a solid. LC/MS: 771.8 [M+1]; $^1$H NMR (400 MHz, METHANOL-d4) d ppm 7.8 (s, 1H), 7.30 (d, J=8.53 Hz, 2H), 7.08-7.18 (m, 2H), 5.66 (d, J=13.05 Hz, 1H), 4.57 (d, J=8.53 Hz, 1H), 4.29 (ddd, J=9.98, 6.71, 2.89 Hz, 1H), 3.90 (br. s., 1H), 3.73 (d, J=6.27 Hz, 1H), 3.24-3.33 (m, 1H), 2.84 (d, J=7.28 Hz, 2H), 2.68 (br. s., 3H), 2.40-2.53 (m, 2H), 2.20-2.36 (m, 1H), 2.03-2.12 (m, 4H), 1.75-2.00 (m, 7H), 1.64 (ddd, J=14.12, 10.23, 4.02 Hz, 2H), 1.42-1.57 (m, 2H), 1.30 (t, J=7.15 Hz, 3H), 1.01-1.17 (m, 7H), 0.88-0.98 (m, 7H), 0.84 (t, J=7.40 Hz, 3H), 0.77 d, J=6.53 Hz, 3H).

Intermediate 29

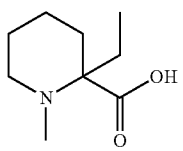

To a solution of 2-ethylpiperidine-2-carboxylic acid (320 mg, 1.65 mmol) in MeOH (4.0 mL) and water (4.0 mL) was added paraformaldehyde (372 mg, 4.13 mmol) and Pd/C (10%) (88 mg, 0.83 mmol). One equivalent of sodium carbonate (175 mg, 1.65 mmol) was added and the reaction mixture was stirred under a hydrogen atmosphere at room temperature for overnight. LC/MS indicated complete conversion of starting material. The reaction mixture was filtered through diatomaceous earth. The filter cake was washed with MeOH (2×30 mL). The filtrate was concentrated in vacuo to give the crude product. The crude solid was suspended in methanol (50 mL) and the resulting suspension was filtered and the filtrate was concentrated to give 2-ethyl-1-methylpiperidine-2-carboxylic acid (202 mg, 71.4%) as a solid. LC/MS: 172 (M+1); $^1$H NMR (400 MHz, CD$_3$OD) δ ppm 3.58 (td, J=12.80, 3.51 Hz, 1 H), 3.09-3.20 (m, 1H), 2.81 (s, 3H), 2.17-2.29 (m, 1H), 1.54-1.84 (m, 7H), 0.98 (t, J=7.40 Hz, 3H).

Intermediate 30

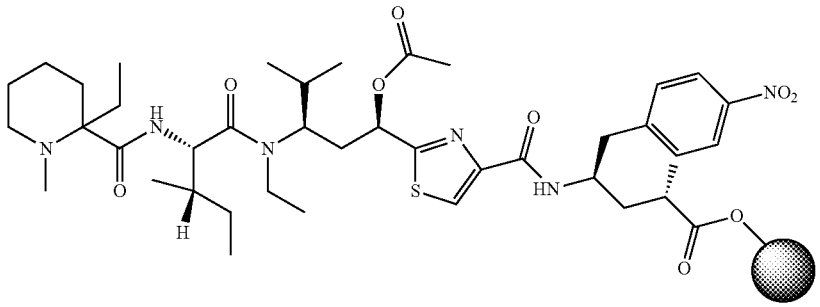 [SMILES: CC[C@H](C)[C@H](NC(=O)C1(CC)CCCCN1C)C(=O)N(CC)[C@H](C[C@@H](OC(C)=O)c1nc(C(=O)N[C@@H](Cc2ccc([N+](=O)[O-])cc2)C[C@H](C)C(=O)OC)cs1)C(C)C]

To the resin intermediate 26 (0.2 g, 0.32 mmol) was added a solution of Intermediate 29 (0.082 g, 0.48 mmol), HATU (0.243 g, 0.64 mmol), 2,4,6-trimethylpyridine (0.127 mL, 0.96 mmol) and DIPEA (0.168 mL, 0.96 mmol) in DMF (5 mL). The mixture was shaken at room temperature for 2 hours, the resulting resin was filtered, washed with DMF (3×4 mL), MeOH (3×4 mL), and DCM (3×4 mL), and was dried in vacuo. Small amount of the compound was cleaved from resin, was analyzed by LCMS, which indicated the reaction was completed. The resulting resin was used to next step reaction. LC/MS: 815 (M+H).

Intermediate 31

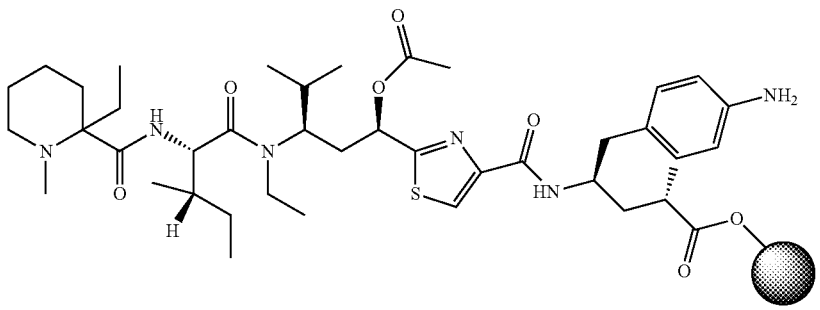 [SMILES: CC[C@H](C)[C@H](NC(=O)C1(CC)CCCCN1C)C(=O)N(CC)[C@H](C[C@@H](OC(C)=O)c1nc(C(=O)N[C@@H](Cc2ccc(N)cc2)C[C@H](C)C(=O)OC)cs1)C(C)C]

To the resin intermediate 30 was added a solution of tin(II) chloride dihydrate (0.544 g, 2.41 mmol) and sodium acetate (0.059 g, 0.72 mmol) in DMF (5 mL). The mixture was shaken at room temperature for 4 hours, the resulting resin was filtered, was washed with DMF (3×6 mL), MeOH (3×6 mL), and DCM (3×6 mL), and dried in vacuo. Small amount of the compound was cleaved from resin, analyzed by LCMS, which indicated the reaction was complete. The resulting resin was used for the next step reaction. LC-MS: 785 (M+H).

Compound 2

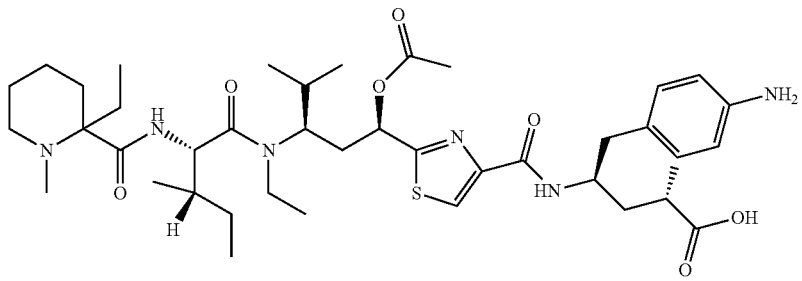 [SMILES: CC[C@H](C)[C@H](NC(=O)C1(CC)CCCCN1C)C(=O)N(CC)[C@H](C[C@@H](OC(C)=O)c1nc(C(=O)N[C@@H](Cc2ccc(N)cc2)C[C@H](C)C(=O)O)cs1)C(C)C]

To the resin intermediate 31 was added DCM (2 mL) and TFA (0.493 mL, 6.40 mmol) at room temperature. The mixture was shaken at room temperature for 20 min. The resin was washed with DCM/TFA (1:1, 3×2 mL), and the filtrates were evaporated in vacuo. The residue was purified by reverse phase HPLC (ACN/H$_2$O 0.1% formic acid, ACN from 10% to 50% in 14 min). The pure fractions were lyophilized to give (2S,4R)-4-(2-((1R,3R)-1-acetoxy-3-((2S,3S)—N-ethyl-2-(2-ethyl-1-methylpiperidine-2-carboxamido)-3-methylpentanamido)-4-methylpentyl)thiazole-4-carboxamido)-5-(4-aminophenyl)-2-methylpentanoic acid (0.057 g, 20.31%) as a white solid. LC-MS: 785 (M+H).; $^1$H NMR (400 MHz, CD$_3$OD) δ ppm 7.98 (s, 1H), 6.87 (m, J=8.28 Hz, 2H), 6.54 (m, J=8.03 Hz, 2H), 5.63-5.73 (m, 1H), 4.60-4.71 (m, 3H), 4.17 (br. s., 2H), 3.76 (dd, J=14.93, 7.15 Hz, 1H), 2.69 (d, J=6.53 Hz, 2H), 2.42 (br. s., 1H), 2.36 (s, 3H), 2.29 (br. s., 2H), 2.03-2.12 (m, 3H), 1.88 (d, J=9.79 Hz, 3H), 1.79 (br. s., 2H), 1.49-1.64 (m, 5H), 1.43 (br. s., 2H), 1.23-1.35 (m, 4H), 1.11 (d, J=7.78 Hz, 1H), 1.06 (d, J=7.03 Hz, 4H), 0.93 (d, J=15.81 Hz, 3H), 0.94 (d, J=15.56 Hz, 3H), 0.70-0.87 (m, 9H).

Intermediate 32

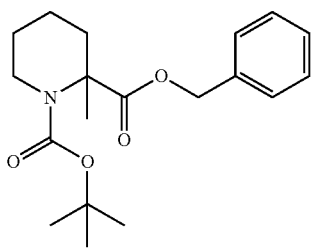 [SMILES: CC(C)(C)OC(=O)N1CCCCC1(C)C(=O)OCc1ccccc1]

To a suspension of 1-(tert-butoxycarbonyl)-2-methylpiperidine-2-carboxylic acid (1 g, 4.11 mmol) and potassium carbonate (0.852 g, 6.17 mmol) in ACN (20 mL) was added drop wise benzyl bromide (0.733 mL, 6.17 mmol). The resulting reaction mixture was stirred at RT overnight. LC/MS indicated formation of desired product. Reaction mixture was diluted with water (2 mL) and extracted with ethyl acetate (2×30 mL). The combined extracts were dried over sodium sulfate, filtered and concentrated. The crude material was purified by flash chromatography (silica gel, Hexane/ethyl acetate, 80/20 eluent) to yield 2-benzyl 1-(tert-butyl) 2-methylpiperidine-1,2-dicarboxylate (1.27 g, 92%) as an oil. LC-MS: 356 (M+Na); $^1$H NMR (400 MHz, CD$_2$Cl$_2$) δ ppm 7.33-7.45 (m, 5H), 5.13-5.27 (m, 2H), 3.91-4.09 (m, 1H), 2.83-3.09 (m, 1H), 2.10-2.32 (m, 1H), 1.56-1.72 (m, 1H), 1.30-1.51 (m, 12H), 1.09 (qd, J=12.42, 4.64 Hz, 1H), 0.90-0.98 (m, 3H).

Intermediate 33

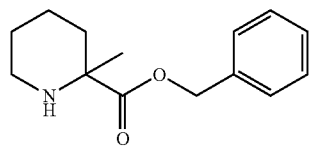 [SMILES: CC1(C(=O)OCc2ccccc2)CCCCN1]

To a solution of Intermediate 32 (1.2 g, 3.60 mmol) in DCM (10 mL) was added TFA (4.16 mL, 53.99 mmol) drop wise. The resulting reaction mixture was stirred at room temperature for 2 hours. LC/MS indicated complete deprotection of Boc. Solvent was removed under reduced pressure. The crude material was basified with aqueous saturated sodium bicarbonate and the aqueous layer was extracted with ethyl acetate (2×50 mL). The combined extracts were dried over sodium sulfate, filtered and concentrated to give benzyl 2-methylpiperidine-2-carboxylate (810 mg) as an oil. The crude product was used for the next step without purification. LC/MS: 234 (M+1).

Intermediate 34

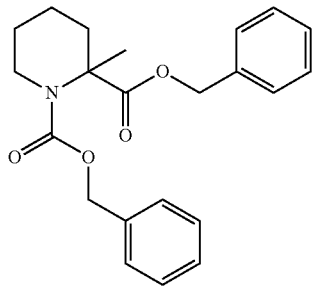 [SMILES: CC1(C(=O)OCc2ccccc2)CCCCN1C(=O)OCc1ccccc1]

To a solution of Intermediate 33 (1.45 g, 6.22 mmol) and DIEA (2.388 mL, 13.67 mmol) in DCM (25 mL) was added. benzyl chloroformate (0.875 mL, 6.22 mmol) drop wise at 0° C. The resulting solution was stirred at room temperature for 2 hours. The reaction mixture was diluted with 30 mL of DCM and 4 mL of aqueous saturated sodium bicarbonate solution, was stirred for 5 minutes. The organic layer was separated and aqueous layer extracted (2×30 mL) with DCM. The combined organic extracts were dried over sodium sulfate, filtered and concentrated. The crude material was purified by flash chromatography (silica gel, hexane/ethyl acetate, 90/10) to give dibenzyl 2-methylpiperidine-1,2-dicarboxylate (1.32 g, 58%) as an oil. LC-MS: 268 (M+1); ¹H NMR (400 MHz, METHANOL-d₄) δ ppm 7.21-7.42 (m, 10H), 5.04-5.18 (m, 2H), 5.00 (br. s., 2H), 4.91 (br. s., 1H), 3.88 (d, J=12.80 Hz, 1H), 3.17 (t, J=9.54 Hz, 1H), 1.83-1.97 (m, 1H), 1.55-1.78 (m, 4H), 1.51 (s, 3H).

Intermediate 35

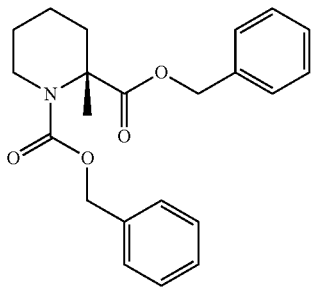 [SMILES: C[C@]1(C(=O)OCc2ccccc2)CCCCN1C(=O)OCc1ccccc1]

Intermediate 34 was subjected to SFC chiral column resolution (Chiralpak AD, carbon dioxide/Methanol 90%-10%) of the two enantiomers to isolate the desired product dibenzyl (R)-2-methylpiperidine-1,2-dicarboxylate, LC-MS: 368 (M+1); ¹H NMR (400 MHz, CD₃OD) δ ppm 7.19-7.44 (m, 10H), 5.04-5.15 (m, 2H), 5.00 (br. s., 2H), 3.88 (d, J=13.05 Hz, 1H), 3.17 (t, J=9.54 Hz, 1H), 1.84-1.97 (m, 1H), 1.55-1.78 (m, 5H), 1.51 (s, 3H); % ee: >98: Optical rotation: [α]$_D$: +2° (Methanol)

Intermediate 36

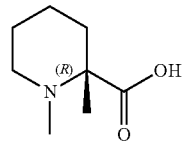

To a solution of Intermediate 35 (600 mg, 1.63 mmol) in Methanol (10 mL) was added paraformaldehyde (49.0 mg, 1.63 mmol) and palladium on carbon (174 mg, 1.63 mmol). The reaction mixture was stirred under a hydrogen atmosphere at room temperature overnight. LC/MS indicated completion of starting material. The reaction mixture was filtered, washed the catalyst with MeOH (2×30 mL). The filtrate was concentrated in vacuo to give crude product as a white solid, which was washed with ether (3×30 mL), dried in high vacuum overnight to yield 1,2-dimethylpiperidine-2-carboxylic acid (230 mg, 90%) a white solid. LC-MS: 158 (M+1); NMR (400 MHz, METHANOL-d4) δ ppm 3.03-3.18 (m, 1H), 2.76 (br. s., 3H), 2.01 (br. s., 1H), 1.83 (br. s., 2H), 1.72-1.81 (m, 1H), 1.62-1.71 (m, 2H), 1.48 (s, 3H).; Optical rotation: α$_D$ +24° (Methanol).

Intermediate 37

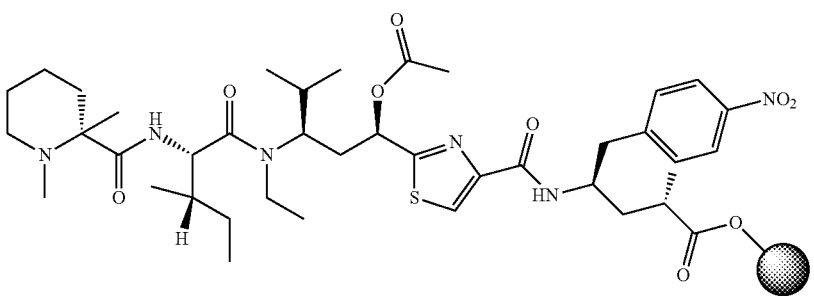 [SMILES: CC[C@H](C)[C@H](NC(=O)[C@@]1(C)CCCCN1C)C(=O)N(CC)[C@H](C[C@@H](OC(C)=O)c1nc(C(=O)N[C@@H](Cc2ccc([N+](=O)[O-])cc2)C[C@H](C)C(=O)OC)cs1)C(C)C]

To the intermediate resin 26 (0.5 g, 0.80 mmol) was added a solution of Intermediate 36 (0.189 g, 1.20 mmol), HATU (0.608 g, 1.60 mmol), 2,4,6-trimethylpyridine (0.318 mL, 2.40 mmol) and DIEA (0.419 mL, 2.40 mmol) in DMF (5 mL). The mixture was shaken at room temperature for 2 hours, the resulting resin was filtered, washed with DMF (3×6 mL), MeOH (3×6 mL), and DCM (3×6 mL), and was dried I. Small amount of the compound was cleaved from resin, analyzed by LC/MS, which indicated the reaction was complete. The resulting resin was used for the next step reaction. LC-MS: 801 (M+1).

Intermediate 38

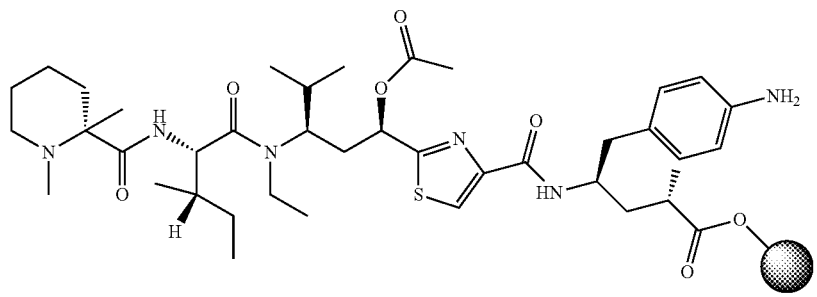 [SMILES: CC[C@H](C)[C@H](NC(=O)[C@@]1(C)CCCCN1C)C(=O)N(CC)[C@H](C[C@@H](OC(C)=O)c1nc(C(=O)N[C@@H](Cc2ccc(N)cc2)C[C@H](C)C(=O)OC)cs1)C(C)C]

To the resin intermediate 37 (0.5 g, 0.80 mmol) was added a solution of tin(II) chloride dihydrate (1.384 g, 6.13 mmol) and sodium acetate (0.151 g, 1.84 mmol) in DMF (5 mL). The mixture was shaken at room temperature for 4 hours, and the resulting resin was filtered, was washed with DMF (3×6 mL), MeOH (3×6 mL), and DCM (3×6 mL), and was dried in vacuum. Small amount of the compound was cleaved from resin, was analyzed by LC/MS, which indicated the reaction was complete. The resulting resin was used for the next step reaction. LC-MS: 771 (M+H).

Compound 3

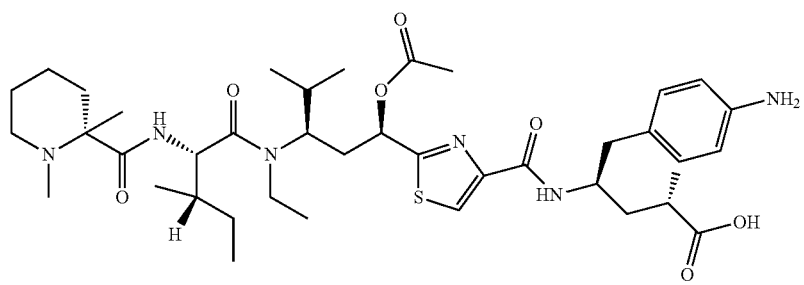 [SMILES: CC[C@H](C)[C@H](NC(=O)[C@@]1(C)CCCCN1C)C(=O)N(CC)[C@H](C[C@@H](OC(C)=O)c1nc(C(=O)N[C@@H](Cc2ccc(N)cc2)C[C@H](C)C(=O)O)cs1)C(C)C]

To the resin intermediate 38 (0.15 g, 0.24 mmol) was added DCM (5 mL), and TFA (0.370 mL, 4.80 mmol) at room temperature. The mixture was shaken at room temperature for 10 min, then was filtered, and was washed with DCM (2×50 mL). The filtrates were evaporated in vacuo. The residue was purified by reverse phase HPLC (ACN/H$_2$O 0.1% formic acid, ACN from 10% to 50% in 14 min). The pure fractions were lyophilized to give (2S,4R)-4-(2-((1R,3R)-1-acetoxy-3-((2S,3S)-2-((R)-1,2-dimethylpiperidine-2-carboxamido)-N-ethyl-3-methylpentanamido)-4-methylpentyl)thiazole-4-carboxamido)-5-(4-aminophenyl)-2-methylpentanoic acid (0.037 g, 17.86%) as a solid. LC/MS: 771 (M+1); $^1$H NMR (400 MHz, CD$_3$OD) δ ppm 7.97 (s, 1H), 6.87 (d, J=8.03 Hz, 2H), 6.53 (d J=8.03 Hz, 2H), 5.67 (d, J=12.80 Hz, 1H), 4.59 (d, J=8.28 Hz, 1H), 4.17 (br. s., 2H), 3.72 (d, J=7.28 Hz, 1H), 2.69 (d, J=6.27 Hz, 3H), 2.42 (br. s., 2H), 2.28 (br. s., 2H), 2.17 (s, 3H), 2.07 (s, 3H), 1.74-1.94 (m, 3H), 1.45-1.62 (m, 4H), 1.36 (br. s., 3H), 1.27 (t, J=7.03 Hz, 3H), 1.10 (s, 3H), 1.06 (d, J=7.03 Hz, 4H), 0.95 (d, J=6.53 Hz, 3H), 0.90 (d, J=6.78 Hz, 4H), 0.83 (t, J=7.40 Hz, 4H), 0.74 (d, J=6.27 Hz, 3H).

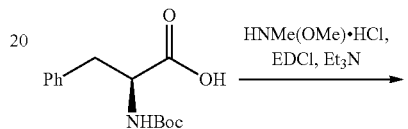

-continued

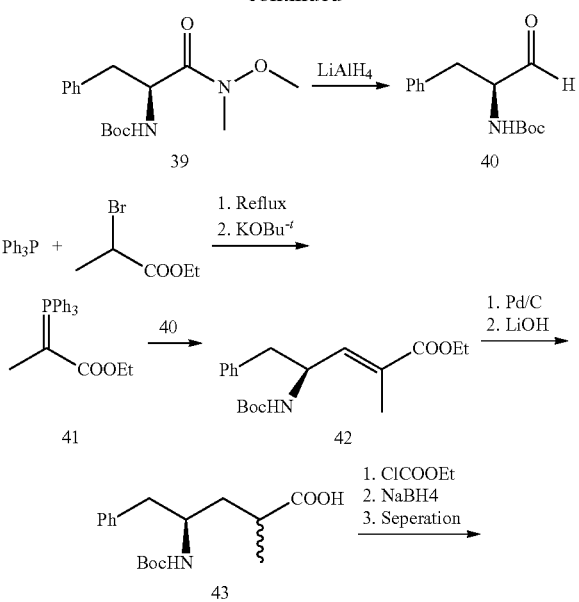

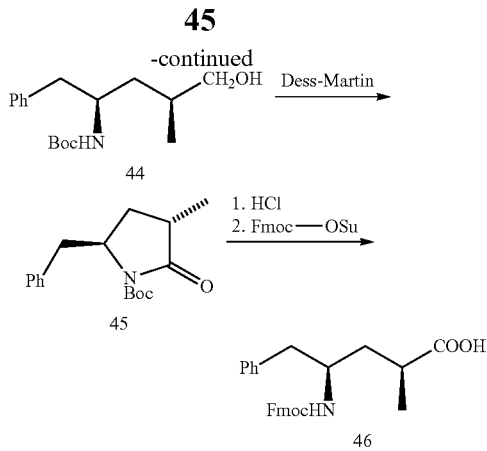

Intermediate 39

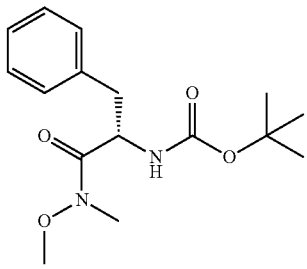 [SMILES: CON(C)C(=O)[C@H](Cc1ccccc1)NC(=O)OC(C)(C)C]

Triethyl amine (40 g, 0.4 mol) was added to a suspension of Boc-L-phenylalanine (90 g, 0.34 mol) and N,O-dimethylhydroxylamine hydrochloride (36.5 g, 0.37 mol) in DCM (500 mL) at 0° C. with stirring. The suspension was stirred for 10 min and EDCI (HCl salt, 72 g, 0.37 mol) was added. The suspension was stirred for further 3 hours at 0° C. The mixture was quenched with saturated aqueous NaHCO$_3$ (1 L). The layers were separated, and the aqueous phase was re-extracted with DCM (500 mL×3). The combined organic phases were washed with water (1 L×3), 5% KHSO$_4$ aqueous (1 L×3), saturated aqueous NaHCO$_3$ (1 L×3), and brine (1 L×1), was dried (Na$_2$SO$_4$), and was concentrated to dryness. The crude material was further purified by flash chromatography (silica gel, EtOAc/Hexane=1:1) and afforded (S)-tert-butyl 1-(methoxy(methyl)amino)-1-oxo-3-phenylpropan-2-ylcarbamate (85.1 g, 81% yield) as a white solid. $^1$H NMR (300 MHz, CDCl$_3$): δ 7.1-57.26 (m, 5H), 5.25 (bs, 1H), 4.95 (m, 1H), 3.63 (s, 3H), 3.14 (s, 3H), 2.83-3.07 (m, 2H), 1.37 (s, 9H).

Intermediate 40

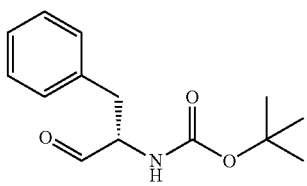 [SMILES: CC(C)(C)OC(=O)N[C@H](C=O)Cc1ccccc1]

A solution of intermediate 39 (97.1 g, 0.315 mol) in dry THF (500 mL) was added dropwise to a suspension of LiAlH$_4$ (12.0 g, 0.316 mol) in dry THF (200 mL) at −10° C. with stirring over 1 hour. The suspension was stirred for further 3 hours at 0° C. then was quenched with water (12 mL), 15% NaOH aqueous (12 mL) and water (12 mL×3) at −10° C. After stirring for 0.5 hour, the mixture was filtered, the filtrate was concentrated to dryness to give (S)-tert-butyl 1-oxo-3-phenylpropan-2-ylcarbamate (45.2 g, crude), which was used for next step without further purification. $^1$H NMR (300 MHz, CDCl$_3$): δ 9.65 (s, 1H), 7.17-7.33 (m, 5H), 4.80 (m, 1H), 2.80-3.15 (m, 2H), 1.45 (s, 9H).

Intermediate 41

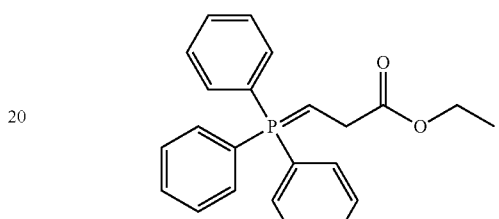

A solution of triphenylphosphine (173.7 g, 0.66 mol) and ethyl 2-bromo-propionate (100 g, 0.55 mol) in ethyl acetate (400 mL) was heated under reflux overnight. After cooling, the mixture was filtered. The cake was washed with ethyl acetate and was dried to give a phosphonium salt. Phosphonium salt was dissolved in DCM (400 mL). Molecular sieves (4 A, 50 g) were added followed by addition of triethyl amine (111 g, 1.1 mol) dropwise at room temperature with stirring. The mixture was stirred for further 1 hours, then was filtered. The filtrate was washed with water (300 mL×3), 5% KHSO$_4$ aqueous (300 mL×3), and brine (300 mL×1), was dried (Na$_2$SO$_4$), and was concentrated to dryness. The crude material was further purified by flash chromatography (silica gel, EtOAc/Hexane=1:10) and afforded ethyl (triphenylphosphoranylidene)propionate (105 g, 52% yield) as a solid. $^1$H NMR (300 MHz, CDCl$_3$): δ 7.3-48.10 (m, 15H), 4.02 (q, J=7.2 Hz, 2H), 1.68 (m, 3H), 1.01 (t, J=7.2 Hz, 3H).

Intermediate 42

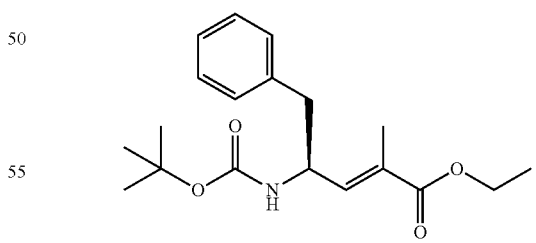

A solution of Intermediate 40 (52 g, 0.21 mol) and Intermediate 41 (76 g, 0.21 mol) in DCM (500 mL) was stirred at room temperature for 14 hours. The solvent was removed under reduced pressure. The residue was further purified by flash chromatography (silica gel, EtOAc/Hexane=1:10) and afforded (S)-Ethyl 4-(tert-butoxycarbonylamino)-2-methyl-5-phenylpent-2-enoate (45.3 g, 64% yield) as an oil. $^1$H NMR (300 MHz, CDCl$_3$): δ 7.1-77.32

(m, 5H), 6.53 (dd, J=1.2 and 9 Hz, 1H), 4.63 (m, 2H), 4.18 (q, J=7.2 Hz, 2H), 2.76-2.95 (m, 2H), 1.72 (s, 3H), 1.42 (s, 9H), 1.28 (t, J=7.2 Hz, 3H).

Intermediate 43

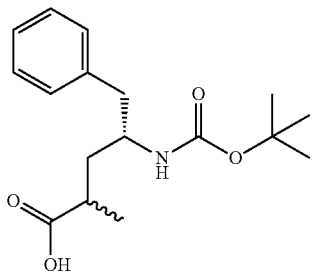 [SMILES: CC(C[C@H](Cc1ccccc1)NC(=O)OC(C)(C)C)C(=O)O]

Intermediate 42 (45 g, 0.135 mol) was dissolved in MeOH (600 mL) containing 10% Pd/C (10 g). The reaction mixture was stirred under a hydrogen atmosphere for 16 h at room temperature. The reaction mixture was filtered through diatomaceous earth and the filtrate was concentrated under reduced pressure. The residue was dissolved in acetone (200 mL) and aqueous NaOH (2M, 135 mL) was added at 0° C. The mixture was stirred at room temperature for 10 hours. The reaction mixture was poured into aqueous HCl (2M, 135 mL), and extracted with DCM (300 mL×3). The combined organic extracts were dried (MgSO₄), filtered, and concentrated under reduced pressure to give (R)-4-(tert-butoxycarbonylamino)-2-methyl-5-phenylpentanoic acid (41.0 g, ~100% yield), which was used for next step without further purification. LC-MS confirmed its structure.

Intermediate 44

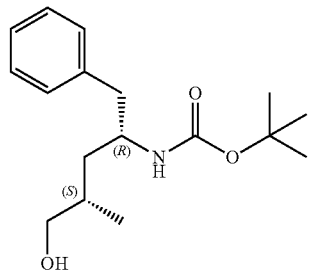

Intermediate 43 (28 g, 0.091 mol) was dissolved in anhydrous THF (200 mL) and cooled to −40° C. To this solution was added triethyl amine (10.1 g, 0.099 mol), followed by dropwise addition of ethyl chloroformate (11 g, 0.10 mol) over 15 min. The reaction mixture was stirred for an additional 1 hour at −40° C., and then was filtered to remove precipitated material. The filtrate was cooled to 0° C. and treated with an aqueous suspension containing sodium borohydride (7.5 g, 0.197 mol) in water (20 mL) over 30 min. The reaction mixture was stirred at 0° C. for 30 min, and at room temperature for an additional 30 min. The mixture was diluted with EtOAc (500 mL), and washed with brine (500 mL). The aqueous layer was extracted with EtOAc (200 mL×3). The combined organic extracts were washed with saturated aqueous NaHCO₃ (500 mL×2), and brine (500 mL), dried (MgSO₄), filtered, and was concentrated under reduced pressure to provide an oily residue. The residue was purified by flash chromatography (silica gel, EtOAc/Hexane=10:1) and afforded tert-butyl (2R,4S)-5-hydroxy-4-methyl-1-phenylpentan-2-ylcarbamate (17.5 g, 65% yield) as an oil. ¹H NMR (300 MHz, CDCl₃): δ 7.1-57.29 (m, 5H), 4.60 (m, 1H), 4.00 (m, 1H), 3.45 (d, J=5.7 Hz, 2H), 2.71-2.11 (m, 4H), 1.78 (m, 1H), 1.55 (m, 1H), 1.38 (s, 9H), 1.25 (m, 1H).

Intermediate 45

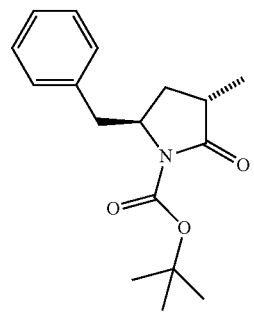 [SMILES: C[C@H]1C[C@H](Cc2ccccc2)N(C(=O)OC(C)(C)C)C1=O]

Dess-Martin periodinane (39 g, 89.4 mmol) was added to a solution of Intermediate 44 (17.5 g, 59.7 mmol) in DCM (300 mL) and the suspension was stirred for 15 hours at room temperature. The mixture was washed with aqueous NaOH (1N, 300 mL×3), and brine (300 mL×3), dried (MgSO₄), filtered, and concentrated under reduced pressure. The residue was purified by flash chromatography (silica gel, EtOAc/Hexane=1:6) and afforded tert-butyl (3S,5R)-5-benzyl-3-methyl-2-oxopyrrolidine-1-carboxylate (9.1 g, 53% yield) as an oil. ¹H NMR (300 MHz, CDCl₃): δ 7.1-67.35 (m, 5H), 4.30 (m, 1H), 3.15 (dd, J=3.3 and 13.2 Hz, 1H), 2.73 (dd, J=9.6 and 13.2 Hz), 2.42 (m, 1H), 2.00-2.10 (m, 2H), 1.58 (s, 9H), 1.15 (d, J=6.9 Hz, 3H).

Intermediate 46

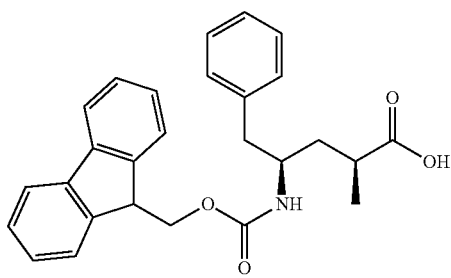 [SMILES: C[C@@H](C[C@H](Cc1ccccc1)NC(=O)OCC1c2ccccc2-c2ccccc21)C(=O)O]

Intermediate 45 (9.0 g, 31.1 mmol) and aqueous HCl (4N, 150 mL) were heated under reflux for 4 hours. After cooling, the solvent was removed under reduced pressure. The residue was dissolved in acetone (100 mL) and water (100 mL). The pH of the solution was adjusted to 8.5 with 2 M aqueous NaOH and a solution of Fmoc-OSu (12 g, 35 mmol) in acetone (20 mL) was added dropwise, pH of this solution was maintained at 8-9 with 2 M aqueous NaOH during this process. The suspension was stirred for 4 hours, then acidified with 2 M aqueous HCl to pH 3, was extracted with EtOAc (200 mL×3). The combined organic phases were washed with water (100 mL×3), 5% KHSO₄ aqueous (100 mL×3), and brine (100 mL×1), dried (Na₂SO₄), and concentrated to dryness. The crude material was purified by flash chromatography (silica gel, EtOAc/Hexane=1:1) and afforded (2S,4R)-4-((((9H-fluoren-9-yl)methoxy)carbonyl)amino)-2-methyl-5-phenylpentanoic acid (5.3 g, 40% yield). LC-MS: 430 [M+1]; 1H NMR (400 MHz, METHANOL-d₄) δ ppm 7.78-7.83 (m, 2H), 7.59-7.65 (m, 2H), 7.37-7.43 (m, 2H), 7.28-7.35 (m, 2H), 7.14-7.26 (m, 5H), 6.94-7.01 (m, 1H), 4.28-4.36 (m, 1H), 4.21-4.27 (m, 1H), 4.10-4.16 (m, 1H), 3.84-3.93 (m, 1H), 2.68-2.82 (m, 2H), 2.48-2.60 (m, 1H), 1.86-1.95 (m, 1H), 1.42-1.51 (m, 1H), 1.17 (d, J=7.03 Hz, 3H), 1.09-1.14 (m, 1H).

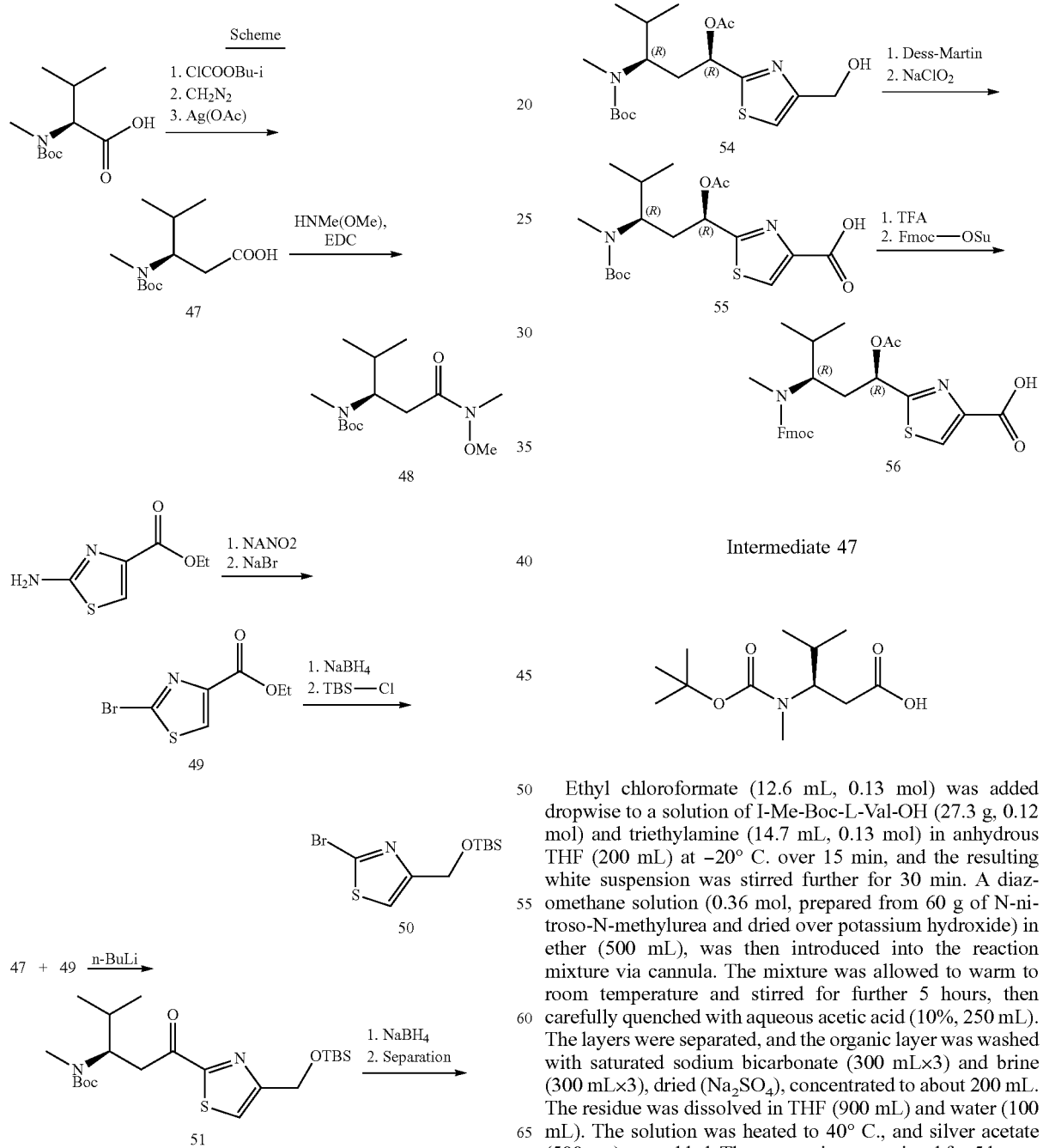

Intermediate 47

Ethyl chloroformate (12.6 mL, 0.13 mol) was added dropwise to a solution of I-Me-Boc-L-Val-OH (27.3 g, 0.12 mol) and triethylamine (14.7 mL, 0.13 mol) in anhydrous THF (200 mL) at −20° C. over 15 min, and the resulting white suspension was stirred further for 30 min. A diazomethane solution (0.36 mol, prepared from 60 g of N-nitroso-N-methylurea and dried over potassium hydroxide) in ether (500 mL), was then introduced into the reaction mixture via cannula. The mixture was allowed to warm to room temperature and stirred for further 5 hours, then carefully quenched with aqueous acetic acid (10%, 250 mL). The layers were separated, and the organic layer was washed with saturated sodium bicarbonate (300 mL×3) and brine (300 mL×3), dried (Na₂SO₄), concentrated to about 200 mL. The residue was dissolved in THF (900 mL) and water (100 mL). The solution was heated to 40° C., and silver acetate (500 mg) was added. The suspension was stirred for 5 hours, then concentrated to about 300 mL. The residue was extracted with EtOAc (500 mL×3). The organic layer was washed with saturated sodium bicarbonate (300 mL×3) and brine (300 mL), dried (Na₂SO₄), concentrated to give (R)-3-(tert-butoxycarbonyl(methyl)amino)-4-methylpentanoic acid (23.8 g, 81% yield) which was used in the next step without further purification. ¹H NMR (300 MHz, CDCl₃): δ 10.08 (bs, 1H), 4.00 (m, 1H), 2.75 (m, 3H), 2.55 (m, 2H), 1.43 (s, 9 h), 0.85-0.84 (m, 6H).

Intermediate 48

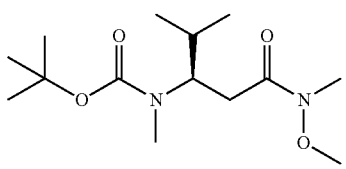 [SMILES: CON(C)C(=O)C[C@H](C(C)C)N(C)C(=O)OC(C)(C)C]

Triethylamine (34.3 mL, 0.244 mol) was added to a suspension of Intermediate 47 (60 g, 0.244 mol) and N,O-dimethylhydroamine hydrochloride (23.9 g, 0.244 mol) in CH₂Cl₂ (300 mL) with stirring at 0° C. The suspension was stirred for 0.5 hour at this temperature, then EDCI (46.9 g, 0.244 mol) was added portions wise at 0° C. The reaction mixture was stirred for further 2 hours at 0° C., then quenched with water (300 mL). The organic phase was separated, and washes with 5% KHSO₄ aqueous (300 mL×3), saturated aqueous NaHCO₃ (300 mL×3), and brine (300 mL×1), dried (Na₂SO₄), and concentrated to dryness. The residue was further purified by silica gel chromatography (EtOAc/Hexane=1:3) and afforded tert-butyl (R)-(1-(methoxy(methyl)amino)-4-methyl-1-oxopentan-3-yl) (methyl)carbamate (52 g, 74% yield) as an oil.

Intermediate 49

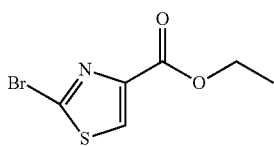

tert-Butyl nitrite (prepared from 0.61 mol of NaNO₂ and 110 mL of tert-butyl alcohol) were added dropwise to a suspension of CuBr₂ (260 g, 1.16 mol) and ethyl 2-aminothiazole-4-carboxylate (100 g, 0.58 mol) in ACN (500 mL) at 0° C. over a period of 1 hour. The mixture was stirred for 12 hours at room temperature, then quenched with EtOAc (800 mL) and water (800 mL). The mixture was filtered, and the filtrate was separated into aqueous and organic phase. The aqueous phase was extracted with EtOAc (800 mL×2). The combined organic extracts were washed with 5% KHSO₄ aqueous (300 mL×3), saturated aqueous NaHCO₃ (300 mL×3), and brine (300 mL×1), dried (Na₂SO₄), and concentrated to dryness to give ethyl 2-bromothiazole-4-carboxylate (79.4 g, 58% yield) which was used in the next step without further purification. ¹H NMR (300 MHz, DMSO-d6): δ 7.45 (s, 1H), 4.20 (q, J=7.2 Hz, 2H), 1.25 (t, J=7.2 Hz, 3H).

Intermediate 50

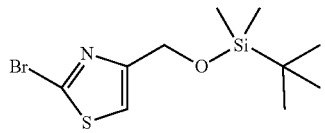

NaBH₄ (16.5 g, 0.43 mol) was added portions wise to a solution of Intermediate 49 (68 g, 0.288 mol) in ethanol (500 mL) at 50° C. over a period of 0.5 hour with stirring. The suspension was heated under reflux for 5 hours, and another batch of NaBH₄ (8.25 g, 0.22 mol) was added portion wise. The mixture was heated under reflux for further 12 hours. After it cooled to room temperature, the solvent was removed under reduced pressure, and the residue was dissolved in DCM (500 mL), and was washed with saturated aqueous NaHCO₃ (300 mL×3), and brine (300 mL×1), dried (Na₂SO₄), and concentrated to dryness to give the alcohol. The alcohol was dissolved in DMF (300 mL), and imidazol (28.3 g, 0.416 mol) was added. A solution of TBS-Cl (62.4 g, 0.416 mol) in THF (100 mL) was added dropwise to this solution at room temperature. The mixture was stirred for 12 hours, then was quenched with water (800 mL), and extracted with EtOAc (800 mL×2). The combined organic extracts were washed with 5% KHSO₄ aqueous (300 mL×3), saturated aqueous NaHCO₃ (300 mL×3), and brine (300 mL×1), dried (Na₂SO₄), and concentrated to dryness. The residue was purified by flash chromatography (silica gel, EtOAc/Hexane=1:30) and afforded 2-Bromo-4-((tert-butyldimethylsilyloxy)methyl)thiazole (42.0 g, 47% yield for two steps) as an oil. ¹H NMR (300 MHz, CDCl₃): δ 7.15 (t, J=1.5 Hz, 1H), 4.84 (d, J=1.5 Hz, 2H), 0.94 9 s, 9H), 0.12 (s, 6H).

Intermediate 51

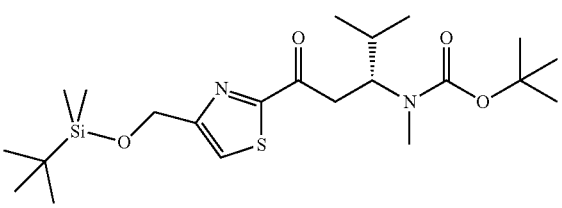 [SMILES: CC(C)[C@@H](CC(=O)c1nc(CO[Si](C)(C)C(C)(C)C)cs1)N(C)C(=O)OC(C)(C)C]

A solution of n-BuLi (77 ml, 2.5N in hexane, 0.19 mol) was added dropwise to a solution of Intermediate 50 (53.9 g, 0.175 mol) in dry THF (500 mL) at −78° C. under N₂ with stirring over 1 hour. The suspension was stirred for 30 min at this temperature. Then a solution of intermediate 48 (50.4 g, 0.175 mol) in dry THF (200 mL) was added dropwise over 30 min at −78° C. The reaction mixture was stirred for 1 hour at this temperature, then allowed to warm to room temperature and stirred for 12 hours. The mixture was quenched with 20% aqueous ammonium chloride (1 L), and the organic solvent was removed under reduced pressure. The resulting mixture was extracted with EtOAc (500 mL×3). The combined organic phases were washed with 5% KHSO₄ aqueous (500 mL×3), saturated aqueous NaHCO₃ (500 mL×3), and brine (500 mL×1), dried (Na₂SO₄), and concentrated to dryness. The crude material was further purified by flash chromatography (silica gel, EtOAc/

Hexane=1:10) and afforded (R)-tert-butyl 1-(4-((tert-butyldimethylsilyloxy)methyl)thiazol-2-yl)-4-methyl-1-oxopentan-3-yl(methyl)carbamate (38.1 g, 48% yield) as an oil. $^1$H NMR (300 MHz, CDCl$_3$): δ 7.55 (m, 1H), 4.91 (s, 2H), 4.27 (m, 1H), 3.2-03.60 (m, 2H), 1.90 (m, 1H), 1.03 (d, J=6.6 Hz, 3H), 0.97 (s, 9H), 0.88 (d, J=6.6 Hz, 3H), 0.15 (s, 6H).

Intermediate 52

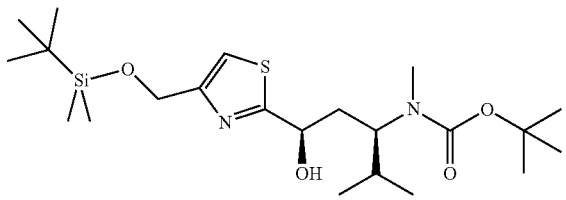 [SMILES: CC(C)[C@@H](C[C@@H](O)c1nc(CO[Si](C)(C)C(C)(C)C)cs1)N(C)C(=O)OC(C)(C)C]

NaBH$_4$ (4.7 g, 125 mmol) was added portions wise to a solution of Intermediate 51 (38.0 g, 83.3 mmol) in methanol (200 mL) at room temperature over a period of 0.5 hour with stirring. The suspension was stirred for 2 hours, and another batch of NaBH$_4$ (1.5 g, 40 mmol) was added and the mixture was stirred for further 2 hours. The solvent was removed under reduced pressure, and the residue was dissolved in EtOAc (200 mL), was washed with saturated aqueous NaHCO$_3$ (200 mL×3), and brine (200 mL×1), dried (Na$_2$SO$_4$), and concentrated to dryness. The crude material was further purified by silica gel chromatography (EtOAc/Hexane=1:6) and afforded tert-butyl (1R,3R)-1-(4-((tert-butyldimethylsilyloxy)methyl)thiazol-2-yl)-1-hydroxy-4-methylpentan-3-yl(methyl)carbamate (16.2 g, 42% yield) and tert-butyl ((1S,3R)-1-(4-(((tert-butyldimethylsilyl)oxy) methyl)thiazol-2-yl)-1-hydroxy-4-methylpentan-3-yl)(methyl)carbamate (isomer, 17.3 g, 45% yield).
tert-butyl (1R,3R)-1-(4-((tert-butyldimethylsilyloxy) methyl)thiazol-2-yl)-1-hydroxy-4-methylpentan-3-yl (methyl)carbamate (1R,3R-Isomer): $^1$H NMR (300 MHz, CDCl$_3$): δ 7.11 (s, 1H), 4.98 (bs, 1H), 4.80 (s, 2H), 4.68 (dt, J=11.7 Hz, 1H), 3.95 (dt, J=3.3 and 12 Hz, 1H), 2.75 (s, 3H), 1.70~1.95 (m, 2H), 1.49 (s, 9H), 0.95 (s, 9H), 0.85-0.95 (m, 6H), 0.15 (s, 6H).
tert-butyl ((1S,3R)-1-(4-(((tert-butyldimethylsilyl)oxy) methyl)thiazol-2-yl)-1-hydroxy-4-methylpentan-3-yl) (methyl)carbamate (1S,3R-Isomer): $^1$H NMR (300 MHz, CDCl$_3$): δ 7.07 (s, 1H), 5.01 (m, 1H), 4.81 (s, 2H), 4.81 (bs, 1H), 3.86 (dt, J=3.3 and 10.5 Hz, 1H), 2.35 (s, 3H), 2.25 (m, 1H), 1.74 (m, 1H), 1.43 (s, 9H), 1.00 (d, J=6.6 Hz, 3H), 0.96 (s, 9H), 0.84 (d, J=6.6 Hz, 3H), 0.15 (s, 6H).

Intermediate 53

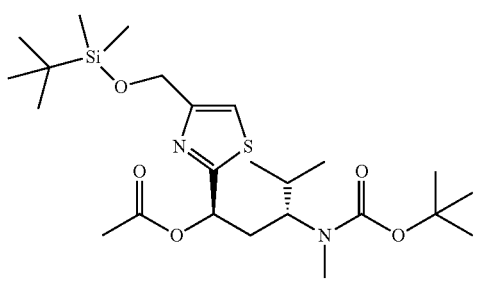 [SMILES: CC(=O)O[C@H](C[C@H](C(C)C)N(C)C(=O)OC(C)(C)C)c1nc(CO[Si](C)(C)C(C)(C)C)cs1]

Acetyl chloride (22.5 mL, 0.316 mol) was added dropwise to a solution of Intermediate 52 (19.7 g, 43 mmol) in pyridine (140 mL) at 0° C. with stirring over 1 hour. The reaction mixture was allowed to warm up to room temperature and stirred for 12 hours. The mixture was quenched with water (200 mL) and the organic solvent was removed under reduced pressure. The residue was dissolved in DCM (500 mL) and washed with 5% KHSO$_4$ aqueous (200 mL×3), saturated aqueous NaHCO$_3$ (200 mL×3), and brine (200 mL×1), dried (Na$_2$SO$_4$), and concentrated to dryness. The crude material was purified by flash chromatography (silica gel, EtOAc/Hexane=1:10) and afforded (1R,3R)-3-(tert-butoxycarbonyl(methyl)amino)-1-(4-((tert-butyldimethylsilyloxy)methyl)thiazol-2-yl)-4-methylpentyl acetate (18.5 g, 86% yield) as an oil. LC-MS confirmed its structure.

Intermediate 54

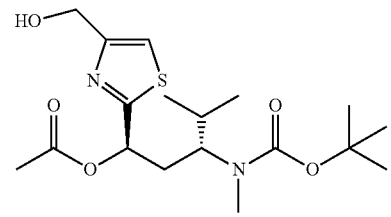 [SMILES: CC(=O)O[C@H](C[C@H](C(C)C)N(C)C(=O)OC(C)(C)C)c1nc(CO)cs1]

A solution of tetrabutylammonium fluoride (45.7 g, 175 mmol) in THF (100 mL) was added dropwise to a solution of Intermediate 53 (17.5 g, 35 mmol) in THF (100 mL) at 0° C. with stirring. The reaction mixture was allowed to warm up to room temperature and stirred for 12 hours. The mixture was quenched with water (100 mL) and the organic solvent was removed under reduced pressure. The residue was dissolved in CH$_2$Cl$_2$ (500 mL) and washed with 5% KHSO$_4$ aqueous (200 mL×3), saturated aqueous NaHCO$_3$ (200 mL×3), and brine (200 mL×1), dried (Na$_2$SO$_4$), and concentrated to dryness. The crude material was purified by flash chromatography (silica gel, EtOAc/Hexane=1:4) and afforded (1R,3R)-3-(tert-butoxycarbonyl(methyl)amino)-1-(4-(hydroxymethyl)thiazol-2-yl)-4-methylpentyl acetate (9.3 g, 69% yield) as an oil. $^1$H NMR (300 MHz, CDCl$_3$): δ 7.15 (d, J=3 Hz, 1H), 5.81-5.86 (m, 1H), 4.74 (d, J=3 Hz, 2H), 4.11 (m, 1H), 2.70 and 2.63 (s, 3H), 2.31 (m, 1H), 2.15 (s, 3H), 2.05 (m, 1H), 1.70 (m, 1H), 1.47 (s, 9H), 0.98 (d, J=6.6 Hz, 3H), 0.86 (d, J=6.6 Hz, 3H).

Intermediate 55

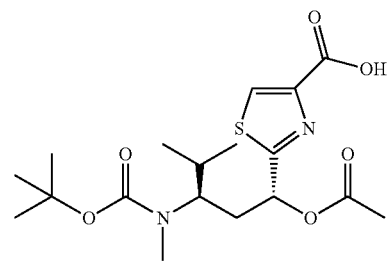 [SMILES: CC(=O)O[C@H](C[C@H](C(C)C)N(C)C(=O)OC(C)(C)C)c1nc(C(=O)O)cs1]

Dess-Martin periodinane (14.9 g, 34.2 mmol) was added to a solution of Intermediate 54 (8.8 g, 22.8 mmol) in dichloromethane (250 mL). The reaction mixture was stirred at room temperature for 12 hours, then washed with aqueous sodium hydroxide (1N, 200 mL×3), aqueous sodium thiosulfate (1N, 200 mL×3), saturated aqueous NaHCO$_3$ (200 mL×3), and brine (200 mL×1), dried (Na$_2$SO$_4$), and concentrated to dryness to give aldehyde.

This crude aldehyde was dissolved in tert-butyl alcohol (250 mL) and a solution of sodium chlorite (80%, 11.6 g, 102 mmol) and sodium dihydrogenphosphate monohydrate (33.6 g, 244 mmol) in water (150 mL) was added dropwise to over 1 hour at room temperature. The reaction mixture was stirred further for 16 h, then diluted with hydrochloric acid (0.1N, 100 mL) and extracted with EtOAc (200 mL×3). The combined organic layers were washed with 5% KHSO$_4$ aqueous (200 mL×3), and brine (200 mL×1), dried (Na$_2$SO$_4$), and concentrated to dryness to give 2-((1R,3R)-1-acetoxy-3-(tert-butoxycarbonyl(methyl)amino)-4-methylpentyl)thiazole-4-carboxylic acid (7.5 g, 82% yield) which was used in the next step without further purification. $^1$H NMR (300 MHz, CDCl$_3$): δ 8.26 (s, 1H), 5.87-6.01 (m, 1H), 4.15 (m, 1H), 2.72 and 2.65 (s, 3H), 2.35 (m, 1H), 2.20 (s, 3H), 2.18 (m, 1H), 1.75 (m, 1H), 1.49 (s, 9H), 1.00 (d, J=6.6 Hz, 3H), 0.88 (d, J=6.6 Hz, 3H).

Intermediate 56

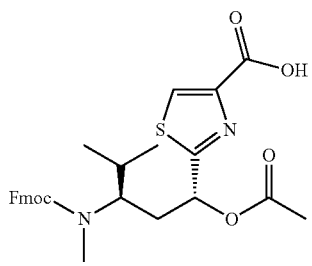

TFA (30 mL) was added to a solution of Intermediate 55 (7.4 g, 18.5 mmol) in dichloromethane (80 mL). The mixture was stirred for 12 hours, and the solvent was removed under reduced pressure. The residue was dissolved in acetone (100 mL) and water (100 mL). The solution pH was adjusted to 8.5 with 2 M aqueous NaOH and a solution of Fmoc-OSu (6.2 g, 18.5 mmol) in acetone (50 mL) was added dropwise, pH of this solution was maintained at 8-9 with 2 M aqueous NaOH during this process. The suspension was stirred for 4 hours was acidified with 2 M aqueous HCl to pH 3, extracted with EtOAc (200 mL×3). The combined organic phases were washed with water (100 mL×3), 5% KHSO$_4$ aqueous (100 mL×3), and brine (100 mL×1), dried (Na$_2$SO$_4$), and concentrated to dryness. The crude material was purified by flash chromatography (silica gel, MeOH/CH$_2$Cl$_2$=1:40) and afforded 2-((1R,3R)-3-((((9H-fluoren-9-yl)methoxy)carbonyl)(methyl)amino)-1-acetoxy-4-methylpentyl)thiazole-4-carboxylic acid (5.1 g, 53% yield). LC-MS: 523 [M+1]; $^1$H NMR (400 MHz, CDCl$_3$) δ ppm 0.56 (br. s., 1H) 0.67-0.82 (m, 2H) 0.83-0.96 (m, 2H) 1.64 (dt, J=10.36, 6.57 Hz, 1H) 1.88 (s, 1H) 2.07 (s, 2H) 2.09-2.17 (m, 1H) 2.19-2.33 (m, 1H) 2.52-2.67 (m, 3H) 3.86-4.01 (m, 1H) 4.08 (s, 1H) 4.12-4.21 (m, 1H) 4.29-4.40 (m, 1H) 4.68 (dd, J=10.61, 5.56 Hz, 1H) 5.85 (dd, J=10.86, 3.28 Hz, 1H) 7.19-7.27 (m, 2H) 7.27-7.35 (m, 2H) 7.42-7.58 (m, 2H) 7.61-7.71 (m, 2H) 8.11-8.19 (m, 1H)

Intermediate 57

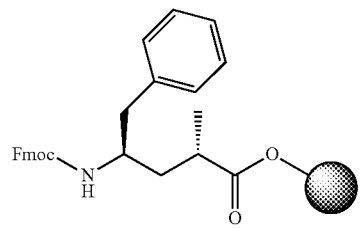

DIEA (0.419 mL, 2.40 mmol) was added to a solution of Intermediate 46 (0.344 g, 0.80 mmol) in DCM (1.5 mL), and the mixture was stirred at room temperature for 5 min, then 2-Chlorotrityl chloride resin (0.5 g, 0.80 mmol) was added to the mixture. The mixture was shaken at room temperature for 4 hours, the resulting resin was washed with DMF (3×6 mL), MeOH (3×6 mL), and DCM (3×6 mL), then treated with DIEA (0.419 mL, 2.40 mmol) MeOH/DCM (1:1, 5 mL) at room temperature for 30 min. Resulting resin was filtered, washed with DMF (3×6 mL), MeOH (3×6 mL), and DCM (3×6 mL), dried in high vacuum overnight. Small amount of compound was cleaved from resin, and analyzed by LCMS. The dried resin was used for the next step. LC-MS: 430 (M+1).

Intermediate 58

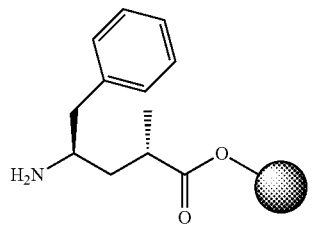 [SMILES: COC(=O)[C@@H](C)C[C@@H](N)Cc1ccccc1]

To the resin Intermediate 57 (0.5 g, 0.80 mmol) was added 20% piperidine in DMF (5 mL). The mixture was shaken at room temperature for 6 min, the resulting resin was filtered, washed with DMF (3×6 mL), MeOH (3×6 mL), DCM (3×6 mL), dried in vacuo. Small amount of the compound was cleaved from resin, analyzed by LC/MS, which indicated the reaction was completed. The resulting resin was used to next step reaction. LC-MS: 208 (M+1).

Intermediate 59

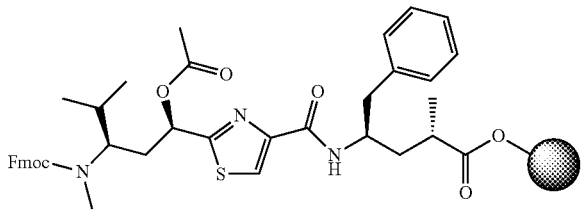

To the resin Intermediate 58 (0.4 g, 0.64 mmol) was added a solution of Intermediate 56 (0.351 g, 0.67 mmol) HATU (0.487 g, 1.28 mmol), 2,4,6-trimethylpyridine (0.256 mL, 1.92 mmol), and DIEA (0.335 mL, 1.92 mmol) in DMF (4 mL). The mixture was shaken at room temperature for 2 hours. The resulting resin was filtered, washed with DMF (3×6 mL), MeOH (3×6 mL), DCM (3×6 mL), dried in vacuo. Small amount of compound was cleaved from resin, and analyzed by LCMS. The reaction was completed. The resulting resin was used to next step reaction. LC-MS: 712 (M+1).

Intermediate 60

To the resin Intermediate 59 (0.4 g, 0.64 mmol) was added 20% piperidine in DMF (4 mL). The mixture was shaken at room temperature for 6 min, the resulting resin was filtered, washed with DMF (3×6 mL), MeOH (3×6 mL), DCM (3×6 mL), dried in vacuo. Small amount of the compound was cleaved from resin, analyzed by LCMS, which indicated the reaction was completed. The resulting resin was used for next step reaction. LC/MS: 491 (M+H).

Intermediate 61

To the resin Intermediate 61 (0.4 g, 0.64 mmol) was added 20% piperidine in DMF (4 mL). The mixture was shaken at room temperature for 6 min, the resulting resin was filtered, washed with DMF (3×6 mL), MeOH (3×6 mL), DCM (3×6 mL), dried in vacuo. Small amount of the compound was cleaved from resin, analyzed by LCMS, which indicated the reaction was completed. The resulting resin was used to next step reaction. LC-MS: 603 (M+1).

To the resin Intermediate 60 (0.4 g, 0.64 mmol) was added a solution of Intermediate 24 (0.341 g, 0.96 mmol), DMAP (3.91 mg, 0.03 mmol), and DIEA (0.335 mL, 1.92 mmol) in DCM (4 mL) at room temperature. The mixture was shaken at room temperature for 1 hour, the resulting resin was filtered, washed with DMF (3×6 mL), MeOH (3×6 mL), DCM (3×6 mL), dried in high vacuum. Small amount of compound was cleaved from resin, and analyzed by LCMS. The resulting resin was used for the next step. LC-MS: 825 (M+1).

Intermediate 62

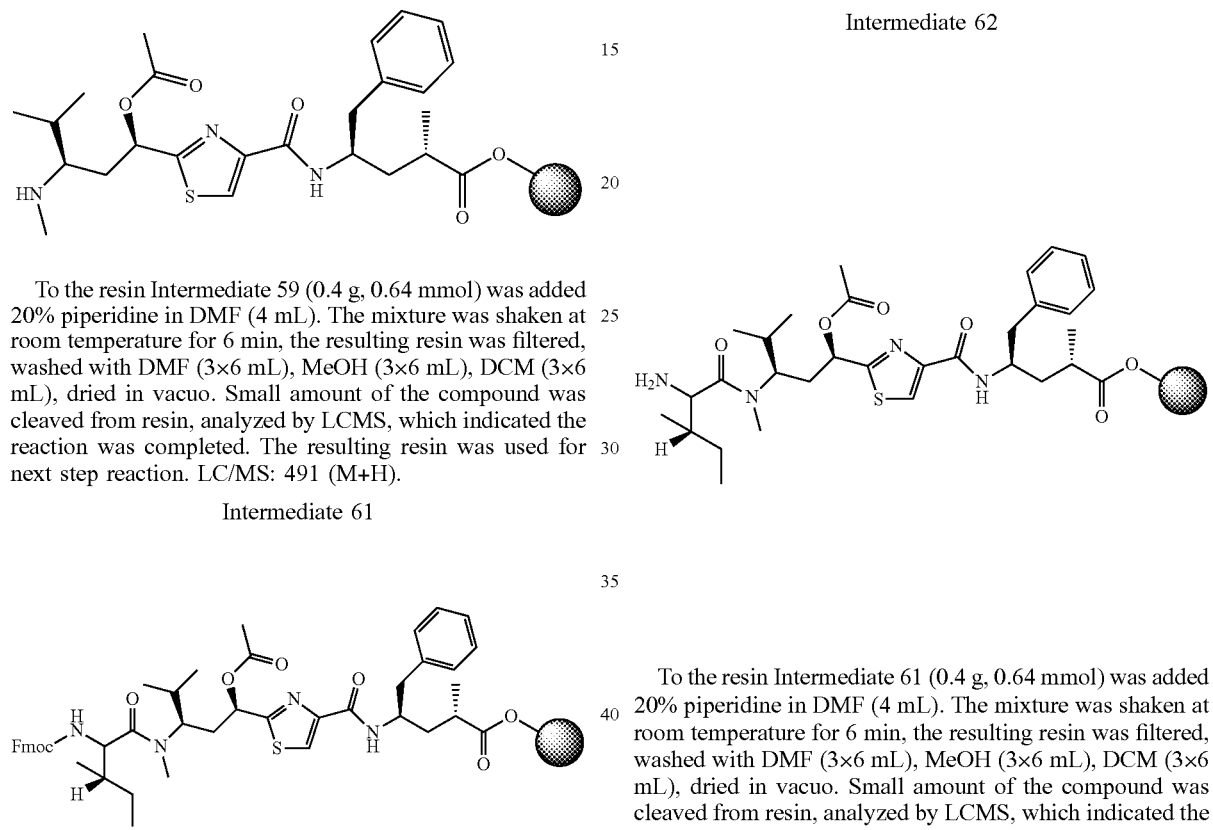

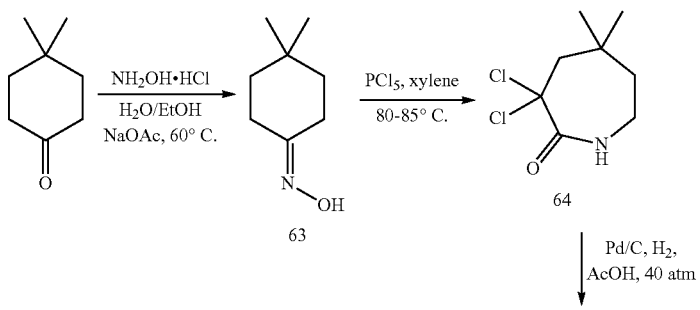

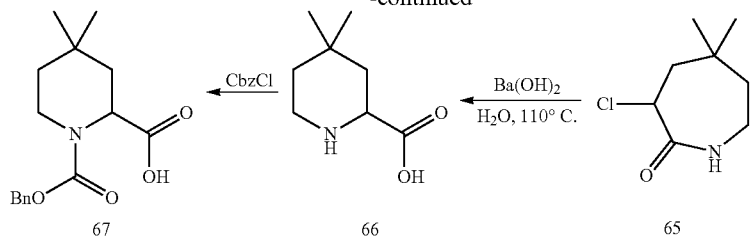

Intermediate 63

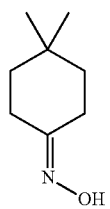

A solution of 4,4-dimethylcyclohexanone (30 g, 0.238 mol), hydroxylamine hydrochloride (32.8 g, 0.476 mol) and sodium acetate (39.0 g, 0.476 mol) in H$_2$O/EtOH (720 mL, 5/1) was heated under reflux. The reaction was monitored by TLC and cooled to room temperature upon completion. It was diluted with dichloromethane (500 mL). The organic layer was separated, washed with brine (100 mL) and dried over Na$_2$SO$_4$. Solvent was removed under reduced pressure, and 4,4-Dimethylcyclohexanone oxime was obtained as colorless solid, which was used in the next step without further purification.

Intermediate 64

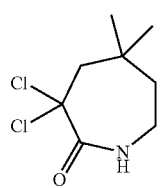

To a stirred slurry of phosphorus pentachloride (120 g, 0.576 mol) in xylene (1000 mL) was added, over 20 minutes, a solution of Intermediate 63 (27.2 g, 0.192 mol) in xylene (400 mL). The reaction mixture was maintained at 30-36° C. using a water bath during the addition. It was then heated to 80° C. and stirred 1.5 hour. The homogeneous reaction mixture was cooled to room temperature and poured into saturated aqueous sodium carbonate (2000 mL). The mixture was put on stand overnight and the precipitate was collected. 3,3-Dichloro-5,5-dimethylazepan-2-one (28.4 g) was obtained as brown solid and it was used for the next step without further purification. $^1$H NMR (300 MHz, CDCl$_3$): δ 6.51 (bs, 1H), 3.39-3.44 (m, 1H), 3.16-3.21 (m, 1H), 1.41-1.51 (m, 2H), 1.17 (s, 2H), 0.99 (s, 6H).

Intermediate 65

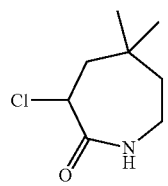

Intermediate 64 (25.8, 0.123 mole) was dissolved in glacial acetic acid (1300 mL) and stirred under 40 atm of hydrogen over Pd/C (13 g, 10%) for 2 h at room temperature. The catalyst was filtered off and the filtrate was concentrated under vacuum. DCM (200 mL) and aqueous saturated NaHCO$_3$ (200 mL) were added to the residue and the mixture was stirred 10 min. The organic layer was separated, dried over Na$_2$SO$_4$ and concentrated under vacuum to afford the 3-chloro-5,5-dimethylazepan-2-one (19.1 g), which was used in the next step without further purification. $^1$H NMR (300 MHz, CDCl$_3$): δ 6.19 (brs, 1H), 4.75 (d, J=11 Hz, 1H), 3.30-3.36 (m, 1H), 3.11-3.17 (m, 1H), 1.91-2.09 (m, 2H), 1.39-1.59 (m, 2H), 1.14 (s, 3H), 1.04 (s, 3H).

Intermediate 66

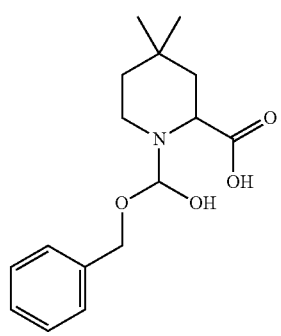 [SMILES: CC1(C)CCN(C(O)OCc2ccccc2)C(C(=O)O)C1]

To a flask charged with Intermediate 65 (16.1 g, 0.092 mol) and Ba(OH)$_2$ (35.1 g, 0.11 mol) was added water (400 mL). This mixture was stirred 2 h at 110° C. It was then cooled to room temperature, and a solution of CBZ chloride (20.6 g, 0.121 mol) in THF (400 mL) was added. The mixture was stirred at room temperature overnight, then adjusted to pH 3 using 1N HCl. The crude product was extracted with ethyl acetate (2×200 mL). The combined extract washed with brine (100 mL), dried over Na$_2$SO$_4$, and concentrated under reduced pressure. The residue was purified by silica gel chromatography to give 1-((benzyloxy)carbonyl)-4,4-dimethylpiperidine-2-carboxylic acid as a viscous oil (7 g). ¹H NMR (300 MHz, CDCl₃): δ 7.33-7.38 (m, 5H), 5.16-5.19 (m, 2H), 4.78-4.88 (m, 1H), 3.95-3.99 (m, 1H), 3.23-3.27 (m, 1H), 2.07 (s, 2H), 1.64-1.71 (m, 1H), 1.37-1.40 (m, 2H), 0.97 (s, 3H), 0.93 (s, 3H).

Intermediate 67

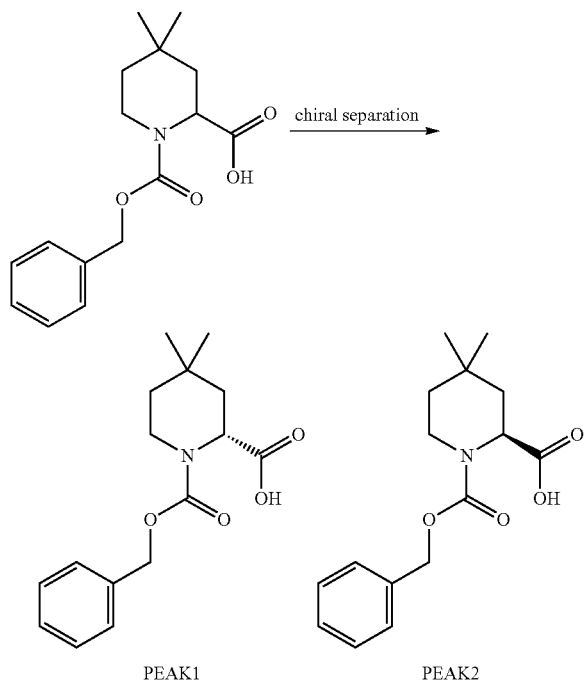

Two enantiomers were separated by chiralpak IC using mobile phase A 90% carbon dioxide/mobile phase B 10% Ethanol (detection at 210 nm). (R)-1-((benzyloxy)carbonyl)-4,4-dimethylpiperidine-2-carboxylic acid: LC-MS: 292 [M+1]; ¹H NMR (400 MHz, CHLOROFORM-d) δ ppm 0.93 (s, 3H) 0.98 (s, 3H) 1.40 (d, J=11.80 Hz, 2H) 1.68 (dd, J=14.05, 7.28 Hz, 1H) 1.99-2.18 (m, 1H) 3.27 (m, J=12.30 Hz, 1H) 3.97 (m, J=12.80 Hz, 1H) 4.69-4.95 (m, 1H) 5.11-5.25 (m, 2H) 7.28-7.44 (m, 5H) 9.63 (br. s, 1H)

Intermediate 68

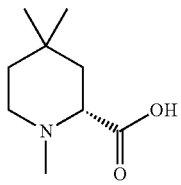

To a solution Intermediate 67 (1.14 g, 3.91 mmol) in MeOH (20 mL) and water (20.00 mL) was added Paraformaldehyde (0.705 g, 7.83 mmol) and Pd/C (10%) (0.4 g, 3.76 mmol). The reaction mixture was stirred under a hydrogen atmosphere at room temperature overnight. From TLC, the reaction was not completed. AnotherParaformaldehyde (0.705 g, 7.83 mmol) was added and the reaction mixture was stirred under a hydrogen atmosphere at room temperature overnight. TLC indicated the reaction was completed. The reaction mixture was filtered, washed the catalyst with MeOH (2×20 mL). The filtrate was concentrated in vacuo to give crude product as a white solid, which was washed with ether (3×20 mL), dried in high vacuum overnight to yield (R)-1,4,4-trimethylpiperidine-2-carboxylic acid (0.671 g, 100%) as a white solid. LC-MS: 172 [M+1]; ¹H NMR (400 MHz, D₂O) δ ppm 0.96 (s, 3H) 1.01 (s, 3H) 1.49-1.63 (m, 3H) 1.83 (dt, J=14.56, 2.64 Hz, 1H) 2.79 (s, 3H) 3.08-3.18 (m, 1H) 3.27-3.34 (m, 1H) 3.54 (dd, J=12.80, 3.26 Hz, 1H).

Intermediate 69

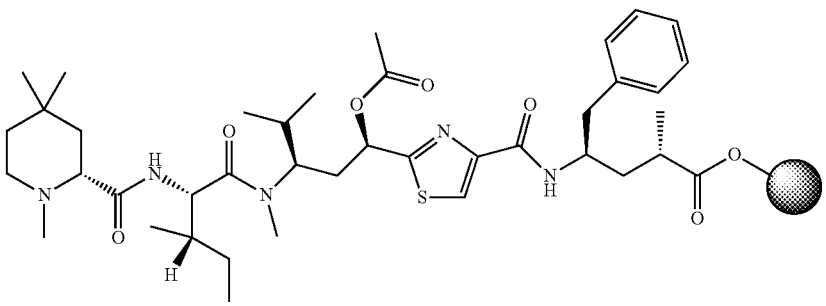 [SMILES: CC[C@H](C)[C@H](NC(=O)[C@H]1CC(C)(C)CCN1C)C(=O)N(C)[C@H](C[C@@H](OC(C)=O)c1nc(C(=O)N[C@@H](Cc2ccccc2)C[C@H](C)C(=O)OC)cs1)C(C)C]

To resin intermediate 62 (0.1 g, 0.16 mmol) was added a solution Intermediate 68 (0.055 g, 0.32 mmol), HATU (0.122 g, 0.32 mmol), 2,4,6-trimethylpyridine (0.064 mL, 0.48 mmol), and DIEA (0.056 mL, 0.32 mmol) in DMF (1 mL). The mixture was shaken at room temperature for 2 hours, the resulting resin was filtered, washed with DMF (3×2 mL), MeOH (3×2 mL), and DCM (3×2 mL), dried in vacuo. Small amount of the compound was cleaved from resin, analyzed by LCMS, which indicated the reaction was completed. The resulting resin was used for the next step. LC-MS: 756 (M+1).

Compound 4

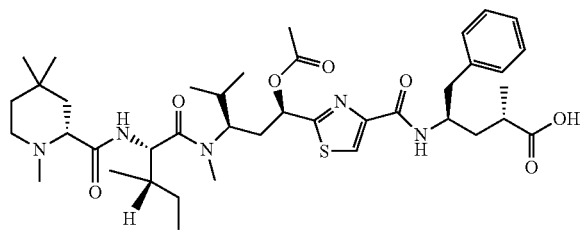 [SMILES: CC[C@H](C)[C@H](NC(=O)[C@H]1CC(C)(C)CCN1C)C(=O)N(C)[C@H](C[C@@H](OC(C)=O)c1nc(C(=O)N[C@@H](Cc2ccccc2)C[C@H](C)C(=O)O)cs1)C(C)C]

To the resin intermediate 69 (0.1 g, 0.13 mmol) was added DCM (1 mL) and TFA (1 mL). The mixture was shaken at room temperature for 20 min, then filtered, the resin was washed with DCM/TFA (1:1, 3×2 mL), the filtrates were evaporated in vacuo. The residue was purified by reverse phase HPLC, (ACN/H$_2$O 0.1% TFA ACN from 5% to 75% in 14 min). The pure fractions were lyophilized to give (2S,4R)-4-(2-((1R,3R)-1-acetoxy-3-((2S,3S)—N,3-dimethyl-2-((R)-1,4,4-trimethylpiperidine-2-carboxamido)pentanamido)-4-methylpentyl)thiazole-4-carboxamido)-2-methyl-5-phenylpentanoic acid (30 mg. yield 30%) as a white solid. LC-MS: 756.5 [M+1]; $^1$H NMR (400 MHz, METHANOL-d$_4$) δ ppm 0.75 (dd, J=6.53, 2.01 Hz, 3H), 0.85 (td, J=7.34, 3.64 Hz, 4H), 0.90-0.99 (m, 11H), 1.01-1.16 (m, 9H), 1.45-1.66 (m, 6H), 1.67-1.85 (m, 4H), 1.86-1.97 (m, 1H), 2.03-2.06 (m, 3H), 2.16-2.34 (m, 2H), 2.39-2.51 (m, 1H), 2.66 (d, J=1.25 Hz, 3H), 2.75-2.85 (m, 2H), 3.02 (d, J=1.25 Hz, 3H), 3.16 (br. s., 1H), 3.79-3.93 (m, 1H), 4.29 (br. s., 2H), 4.57-4.66 (m, 1H), 5.55-5.70 (m, 1H), 7.01-7.18 (m, 5H), 7.98 (d, J=1.25 Hz, 1H).

Intermediate 70

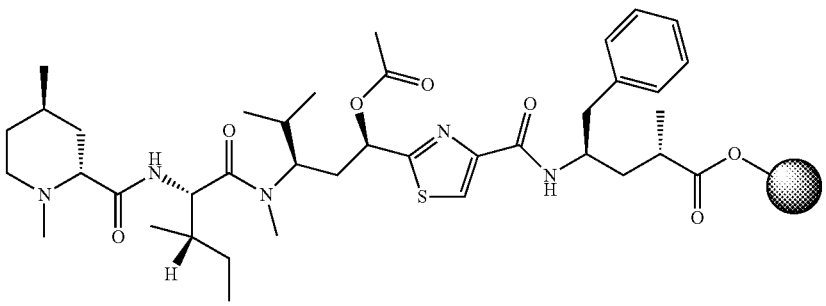 [SMILES: CC[C@H](C)[C@H](NC(=O)[C@H]1C[C@H](C)CCN1C)C(=O)N(C)[C@H](C[C@@H](OC(C)=O)c1nc(C(=O)N[C@@H](Cc2ccccc2)C[C@H](C)C(=O)OC)cs1)C(C)C]

To the resin intermediate 62 (0.1 g, 0.16 mmol) was added a solution of Intermediate 1 (0.050 g, 0.32 mmol), HATU (0.122 g, 0.32 mmol), 2,4,6-trimethylpyridine (0.064 mL, 0.48 mmol), and DIEA (0.056 mL, 0.32 mmol) in DMF (1 mL). The mixture was shaken at room temperature for 2 hours, the resulting resin was filtered, washed with DMF (3×2 mL), MeOH (3×2 mL), and DCM (3×2 mL), dried in vacuo. Small amount of the compound was cleaved from the resin, analyzed by LCMS, which indicated the reaction was completed. The resulting resin was used for the next step. LC-MS: 742 (M+1).

Compound 5

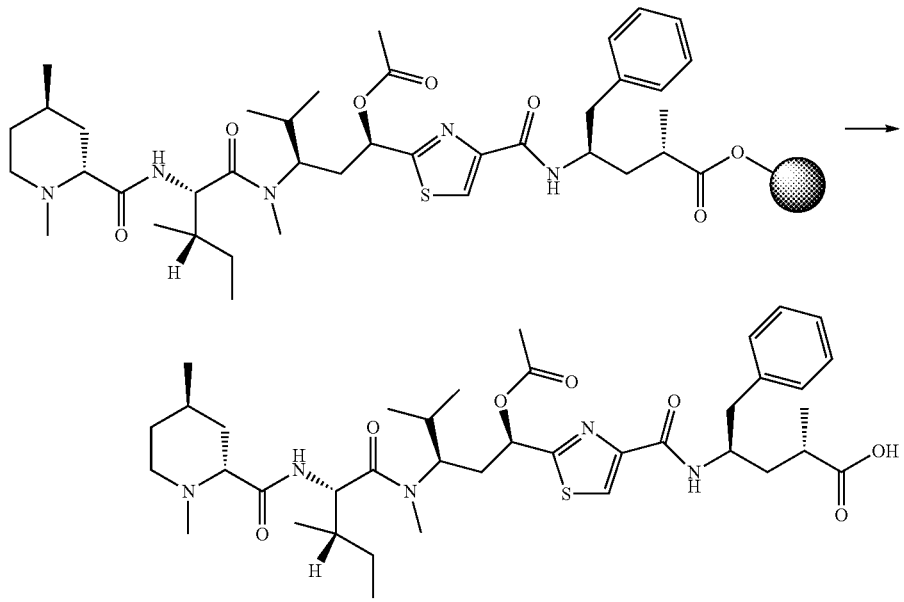

To the resin intermediate 70 (0.1 g, 0.16 mmol) was added DCM (1 mL) and TFA (1 mL). The mixture was shaken at room temperature for 20 min, then filtered, the resin was washed with DCM/TFA (1:1, 3×2 mL), the filtrates were evaporated in vacuo. The residue was purified by reverse phase HPLC (ACN/H$_2$O 0.1% TFA, ACN from 5% to 50% in 14 min). The pure fractions were lyophilized to give (2S,4R)-4-(2-((1R,3R)-1-acetoxy-3-((2S,3S)-2-((2R,4R)-1,4-dimethylpiperidine-2-carboxamido)-N,3-dimethylpentanamido)-4-methylpentyl)thiazole-4-carboxamido)-2-methyl-5-phenylpentanoic acid (0.040 g, 29.2%) as a white solid. LC-MS: 742 (M+1); $^1$H NMR (400 MHz, CD$_3$OD) δ ppm 0.71-0.78 (m, 3H), 0.80-0.87 (m, 3H), 0.93 (dd, J=9.91, 6.65 Hz, 6H), 1.07 (d, J=7.03 Hz, 6H), 1.42-1.65 (m, 3H), 1.74-1.85 (m, 3H), 1.86-1.98 (m, 3H), 2.05 (s, 4H), 2.16-2.35 (m, 2H), 2.38-2.51 (m, 1H), 2.59-2.72 (m, 3H), 2.77-2.83 (m, 2H), 3.02 (s, 3H), 3.84-3.94 (m, 1H), 4.20-4.35 (m, 2H), 4.56-4.65 (m, 1H), 5.57-5.67 (m, 1H), 7.03-7.09 (m, 1H), 7.13 (s, 4H), 7.91-8.02 (m, 2H).

Intermediate 71

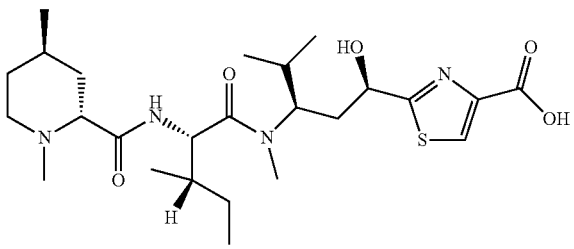 [SMILES: CC[C@H](C)[C@H](NC(=O)[C@H]1C[C@H](C)CCN1C)C(=O)N(C)[C@H](C[C@@H](O)c1nc(C(=O)O)cs1)C(C)C]

To a solution of ethyl 2-((1R,3R)-3-((2S,3S)-2-(tert-butoxycarbonylamino)-N,3-dimethylpentanamido)-1-hydroxy-4-methylpentyl)thiazole-4-carboxylate (prepared as described in Patterson A. et al *J. Org. Chem.* 2008, 73, 4362) (1.2 g, 2.40 mmol) in DCM (24 mL) was added an equal volume of TFA (24.00 mL) with stirring for 1 h. The solution was then concentrated, diluted with EtOAc, and washed once with saturated NaHCO$_3$ (aq). The aqueous fraction was back-extracted twice with EtOAc, and the combined organic fractions were dried with Na$_2$SO$_4$, filtered, and concentrated to afford the Boc-deprotected free amine, which was taken on to the next step without further purification. To this amine in CH$_2$Cl$_2$ (24 mL) were added HOBT (0.368 g, 2.40 mmol) and Intermediate 1 (0.3969 g, 2.52 mmol). The mixture was then cooled in a salted ice-water bath with stirring, and PS-Carbodiimide (1.23 mmol/g) (2.598 g, 2.88 mmol) was added. The bath was warmed to RT, and stirring was continued for 14 h. The mixture was then filtered, the resin was washed with DCM, and the filtrate was concentrated. The crude mixture was then diluted with EtOAc and washed once with saturated aqueous NaHCO$_3$. The aqueous fraction was back-extracted twice with EtOAc, and the combined organic fractions were dried with Na$_2$SO$_4$, filtered, and concentrated to afford the 4-MethylMep-coupled intermediate, which was taken on without further purification. To the crude intermediate diluted in dioxane (24 mL) was added a solution of LiOH (0.230 g, 9.60 mmol) in degassed water (24 mL). After stirring for 5 h, the solution was concentrated. The residue was purified by silica gel column, eluted with DCM/DCM:MeOH:NH$_4$OH (90:10:1 to 70:30:1) (DCM:MeOH:NH$_4$OH as gradient from 0 to 100%) by using normal phase flash chromatography. The pure fractions were concentrated and finally dried under high vacuum to afford 2-((1R,3R)-3-((2S,3S)-2-((2R,4R)-1,4-dimethylpiperidine-2-carboxamido)-N,3-dimethylpentanamido)-1-hydroxy-4-methylpentyl)thiazole-4-carboxylic acid (1.003 g, 82%) as an amorphous solid. LC-MS: 509 [M+1].

Intermediate 72

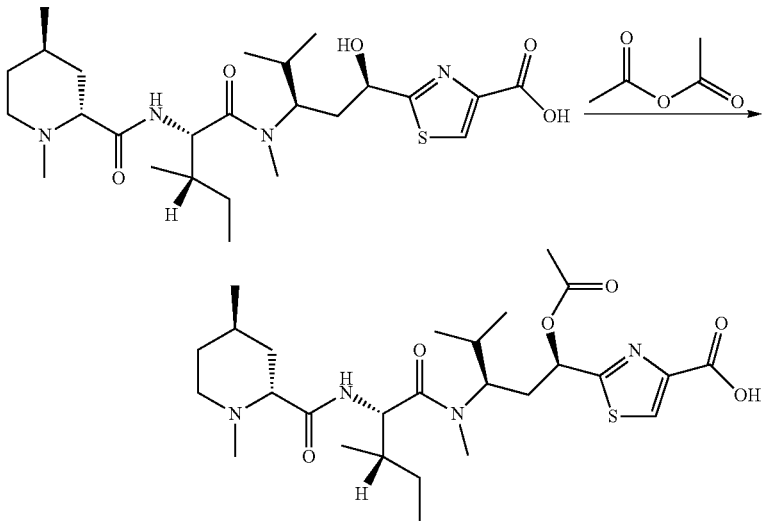

To a solution of Intermediate 71 (1.0026 g, 1.96 mmol) in pyridine (19.47 mL) was cooled in an ice-water bath, and acetic anhydride (0.927 ml, 9.82 mmol) was added with stirring. The bath was warmed to room temperature, and stirring was continued for 24 h. The solution was then cooled in an ice-water bath, and a 1:1 (v/v) solution of degassed water/dioxane (40 mL) was added. The bath was warmed to room temperature, and stirring was continued for 22 h. The residue was concentrated by evaporation and the residue was purified by reverse phase chromatography using ACN/H$_2$O (0.1% TFA), ACN from 5% to 50% in 14 minutes, the pure fractions were lyophilized to give 2-((1R,3R)-1-acetoxy-3-((2S,3S)-2-((2R,4R)-1,4-dimethylpiperidine-2-carboxamido)-N,3-dimethylpentanamido)-4-methylpentyl)thiazole-4-carboxylic acid (0.945 g, 72.2%) as colorless solid. LC-MS: 551 [M+1]; $^1$H NMR (400 MHz, METHANOL-d$_4$) δ ppm 0.85 (d, J=6.53 Hz, 3H), 0.88-0.98 (m, 4H), 0.98-1.08 (m, 6H), 1.10-1.28 (m, 4H), 1.59 (ddd, J=13.49, 7.47, 2.89 Hz, 1H), 1.70 (d, J=14.05 Hz, 1H), 1.81-2.12 (m, 5H), 2.12-2.25 (m, 3H), 2.32 (d, J=7.78 Hz, 2H), 2.72-2.93 (m, 4H), 3.07-3.18 (m, 4H), 4.02 (d, J=10.54 Hz, 1H), 4.10-4.39 (m, 1H), 4.65-4.76 (m, 1H), 5.64-5.80 (m, 1H), 8.30-8.39 (m, 1H), 8.66 (d, J=7.28 Hz, 1H).

Intermediate 73

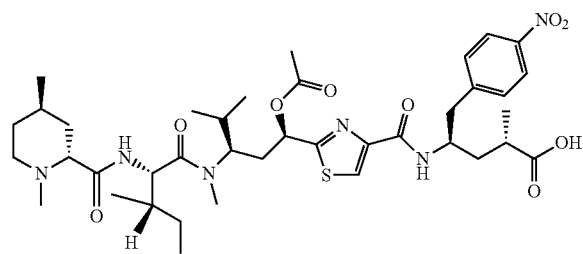 [SMILES: CC[C@H](C)[C@H](NC(=O)[C@H]1C[C@H](C)CCN1C)C(=O)N(C)[C@H](C[C@@H](OC(C)=O)c1nc(C(=O)N[C@@H](Cc2ccc([N+](=O)[O-])cc2)C[C@H](C)C(=O)O)cs1)C(C)C]

Intermediate 72 (100 mg, 0.18 mmol) was added to a solution of 2,3,4,5,6-pentafluorophenol (49.32 mg, 0.27 mmol) and DIC (41.34 μl, 0.27 mmol) in DCM (5 mL) at 0° C. The solution was allowed to reach room temperature, was stirred for 4 hours, then the solvent was removed under vacuum. EtOAc (4 mL) was added to the mixture and the resulting suspension was suction filtered, to afford the desired activated acid in the filtrate. The EtOAc was removed under vacuum, then dry DMF (1.3 mL) was added, followed by the Intermediate 18 (52.2 mg, 0.18 mmol) and DIEA (0.213 mL). The mixture was stirred overnight and then DMF was removed under high vacuum. The residue was purified by reverse phase chromatography (ACN/H$_2$O with 10 mM ammonium acetate, ACN from 10% to 80% in 20 minutes), and the pure fractions were lyophilization to afford the (2S,4R)-4-(2-((1R,3R)-1-acetoxy-3-((2S,3S)-2-((2R,4R)-1,4-dimethylpiperidine-2-carboxamido)-N,3-dimethylpentanamido)-4-methylpentyl)thiazole-4-carboxamido)-2-methyl-5-(4-nitrophenyl)pentanoic acid (85 mg, 59.3%) as colourless solid. LC-MS: 787 [M+1]

Compound 6

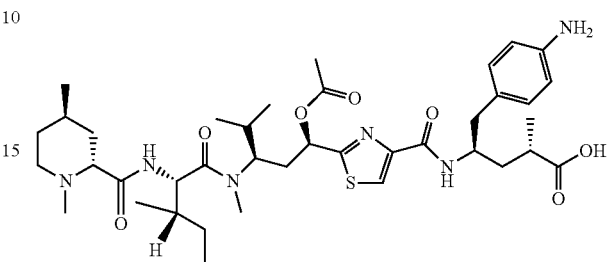

A 25 mL round bottom flask was charged with stirring bar and Intermediate 73 (84.5 mg, 0.11 mmol) and MeOH (5 mL), Pd-C 10% (50 mg, 0.47 mmol) was added under nitrogen. The mixture was hydrogenated by using hydrogen balloon for 1 hour at room temperature. The crude LC/MS showed complete conversion of starting material to product. The reaction mixture was filtered through diatomaceous earth pad, and was washed with MeOH on the filter. The filtrate was concentrated under reduced pressure and finally dried under high vacuum to afford the (2S,4R)-4-(2-((1R,3R)-1-acetoxy-3-((2S,3S)-2-((2R,4R)-1,4-dimethylpiperidine-2-carboxamido)-N,3-dimethylpentanamido)-4-methylpentyl)thiazole-4-carboxamido)-5-(4-aminophenyl)-2-methylpentanoic acid (79 mg, 97%) as a solid. LC-MS: 757 [M+1]; $^1$H NMR (400 MHz, METHANOL-d4) δ ppm 8.10 (s, 1H) 6.99 (d, J=8.28 Hz, 2H) 6.65 (d, J=8.28 Hz, 2H) 5.66-5.78 (m, 1H) 4.71-4.80 (m, 1H) 4.24-4.43 (m, 2H) 3.13 (s, 3H) 2.77-2.83 (m, 2H) 2.61-2.71 (m, 1H) 2.49-2.56 (m, 1H) 2.44 (s, 3H) 2.27-2.40 (m, 2H) 2.17 (s, 3H) 1.86-2.04 (m, 4H) 1.74-1.83 (m, 1H) 1.53-1.69 (m, 3H) 1.31 (br. s., 3H) 1.17 (d, J=7.03 Hz, 4H) 0.98-1.07 (m, 8H) 0.93 (d, J=7.53 Hz, 6H) 0.83-0.87 (m, 3H).

General Synthesis Scheme for Compounds 7-10

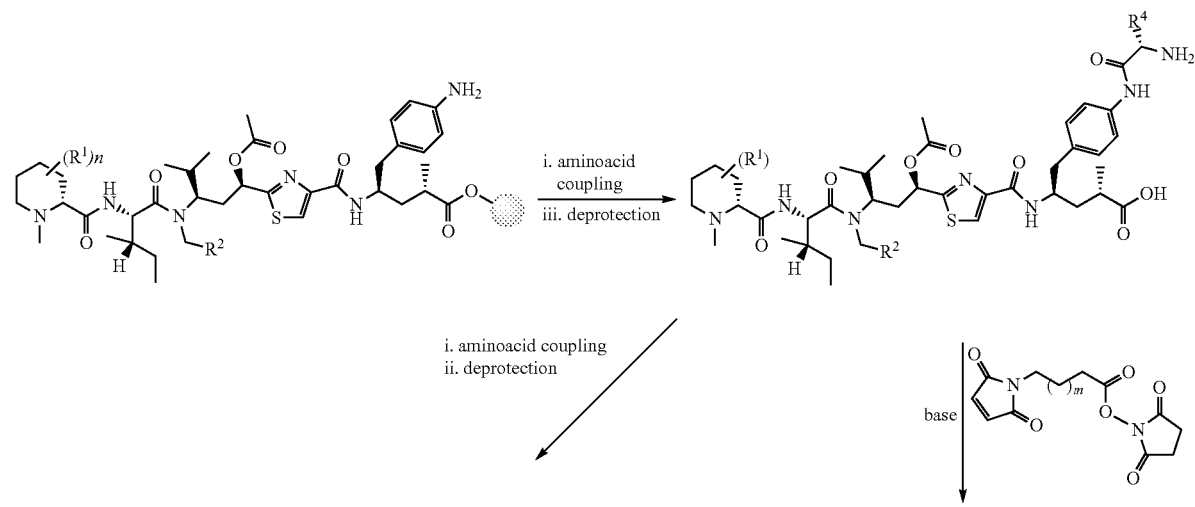

-continued
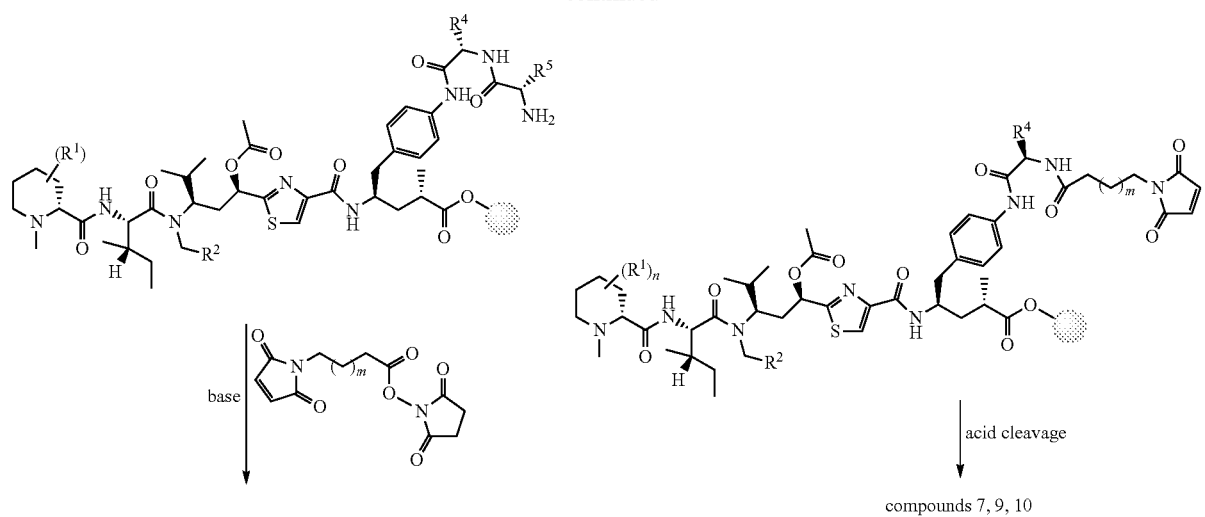
compounds 7, 9, 10
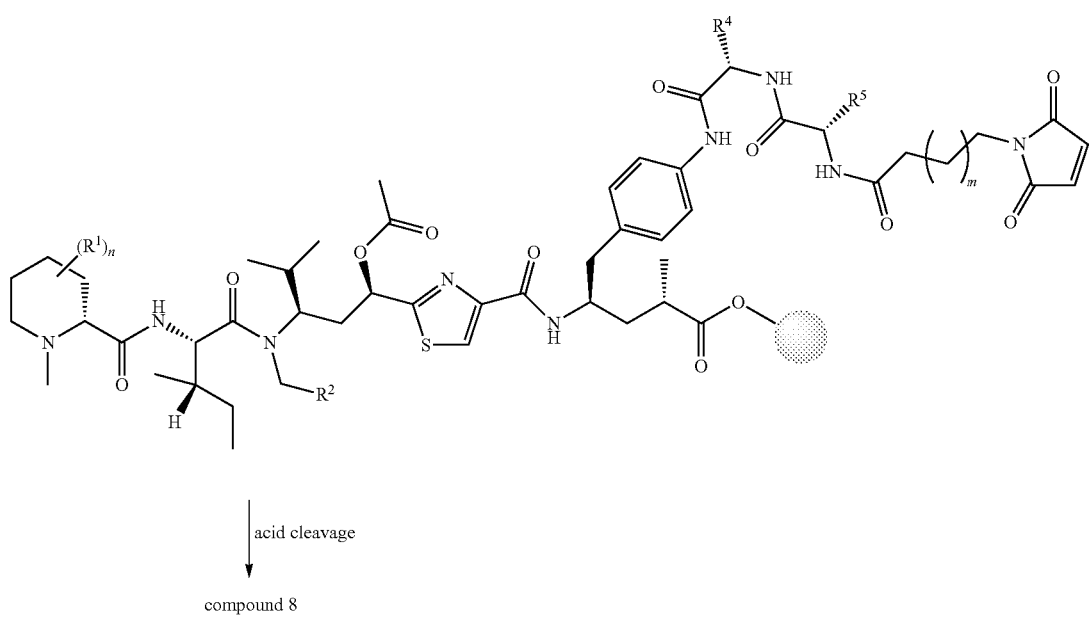
compound 8

Intermediate 74

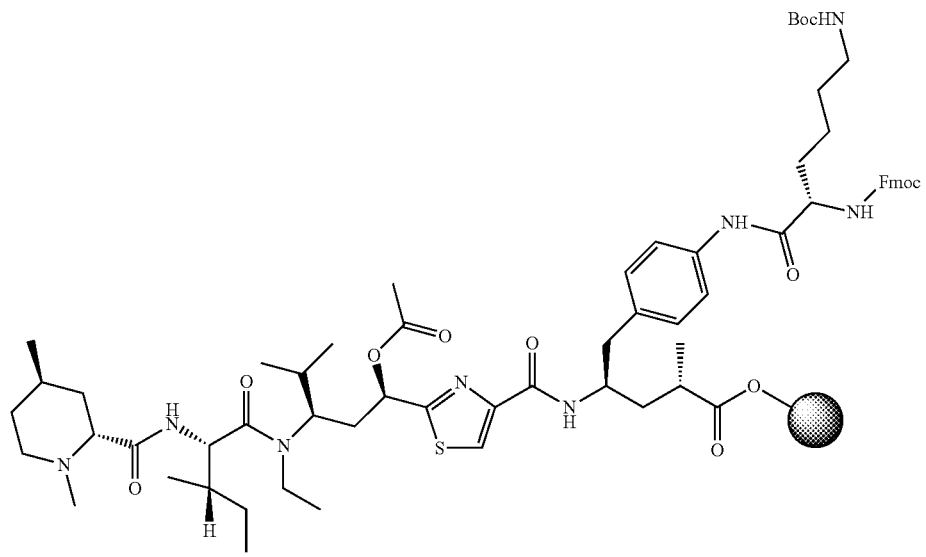

To the resin intermediate 28 (0.2 g, 0.32 mmol) was added a solution of (S)-2-(((9H-fluoren-9-yl)methoxy)carbonylamino)-6-(tert-butoxycarbonylamino)hexanoic acid (0.300 g, 0.64 mmol), HATU (0.243 g, 0.64 mmol), 2,4,6-trimethylpyridine (0.128 mL, 0.96 mmol), and DIEA (0.168 mL, 0.96 mmol) in DMF (4 mL). The mixture was shaken at room temperature for 2 hours, the resulting resin was filtered, washed with DMF (3×2 mL), MeOH (3×2 mL), and DCM (3×2 mL), and dried in vacuo. Small amount of the compound was cleaved from resin, analyzed by LCMS, which indicated the reaction was completed. The resulting resin intermediate 74 was used to next step reaction. LC-MS: 1221 (M+1).

Intermediate 75

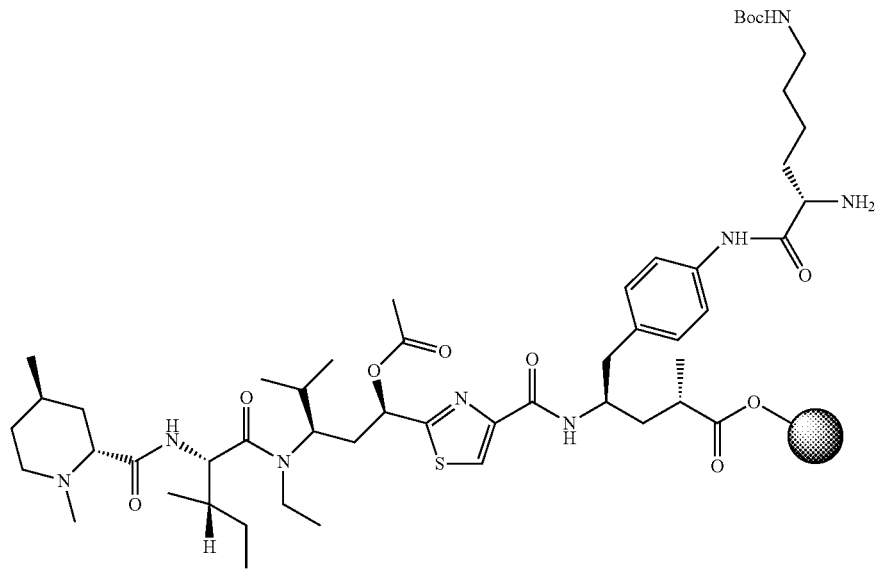 [SMILES: CC[C@H](C)[C@H](NC(=O)[C@H]1C[C@H](C)CCN1C)C(=O)N(CC)[C@H](C[C@@H](OC(C)=O)c1nc(C(=O)N[C@@H](Cc2ccc(NC(=O)[C@@H](N)CCCCNC(=O)OC(C)(C)C)cc2)C[C@H](C)C(=O)OC)cs1)C(C)C]

To the resin intermediate 74 (0.2 g, 0.32 mmol) was added 20% piperidine in DMF (2 mL). The mixture was shaken at room temperature for 6 min, the resulting resin was filtered, washed with DMF (3×3 mL), MeOH (3×3 mL), DCM (3×3 mL), dried in vacuo. Small amount of the compound was cleaved from resin, analyzed by LCMS, which indicated the reaction was completed. The resulting resin intermediate 75 was used to next step reaction. LC/MS: 999 (M+H).

Intermediate 76

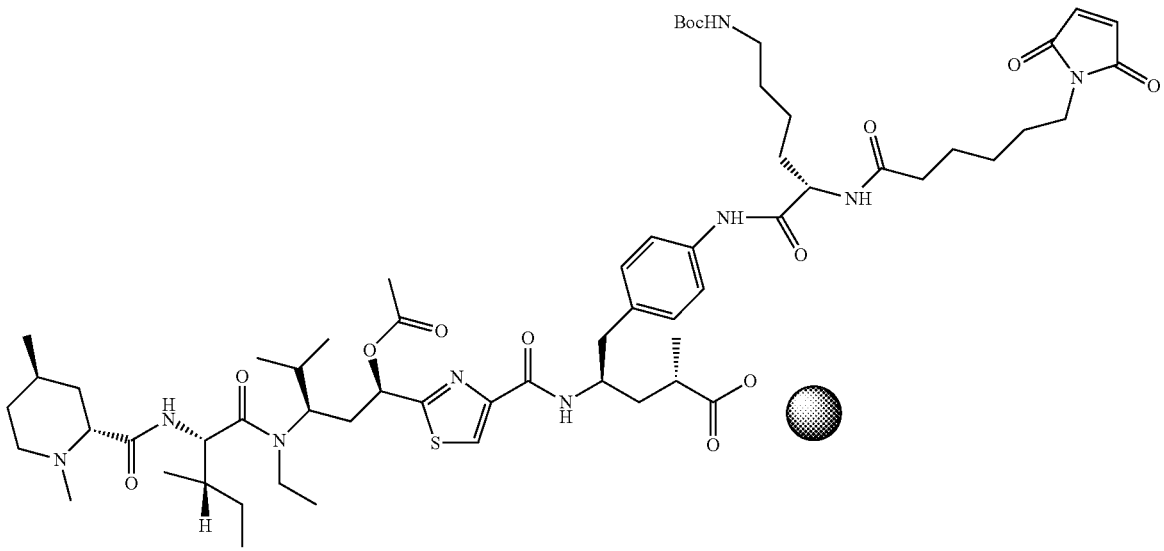 [SMILES: CC[C@H](C)[C@H](NC(=O)[C@H]1C[C@H](C)CCN1C)C(=O)N(CC)[C@H](C[C@@H](OC(C)=O)c1nc(C(=O)N[C@@H](Cc2ccc(NC(=O)[C@H](CCCCNC(=O)OC(C)(C)C)NC(=O)CCCCCN3C(=O)C=CC3=O)cc2)C[C@H](C)C(=O)O)cs1)C(C)C]

To the resin intermediate 75 (0.2 g, 0.32 mmol) was added a solution of 2,5-dioxopyrrolidin-1-yl 6-(2,5-dioxo-2,5-dihydro-1H-pyrrol-1-yl)hexanoate (0.148 g, 0.48 mmol) in DMF (2 mL), followed by N-methylmorpholine (0.106 mL, 0.96 mmol) at room temperature. The mixture was shaken at room temperature for 2 hours, the resulting resin was filtered, washed with DMF (3×3 mL), DCM (3×3 mL), dried in vacuo. Small amount of the compound was cleaved from resin, analyzed by LCMS, which indicated the reaction was completed. The resulting resin intermediate 76 was used for the next step. LC-MS: 1192 (M+1).

Compound 7

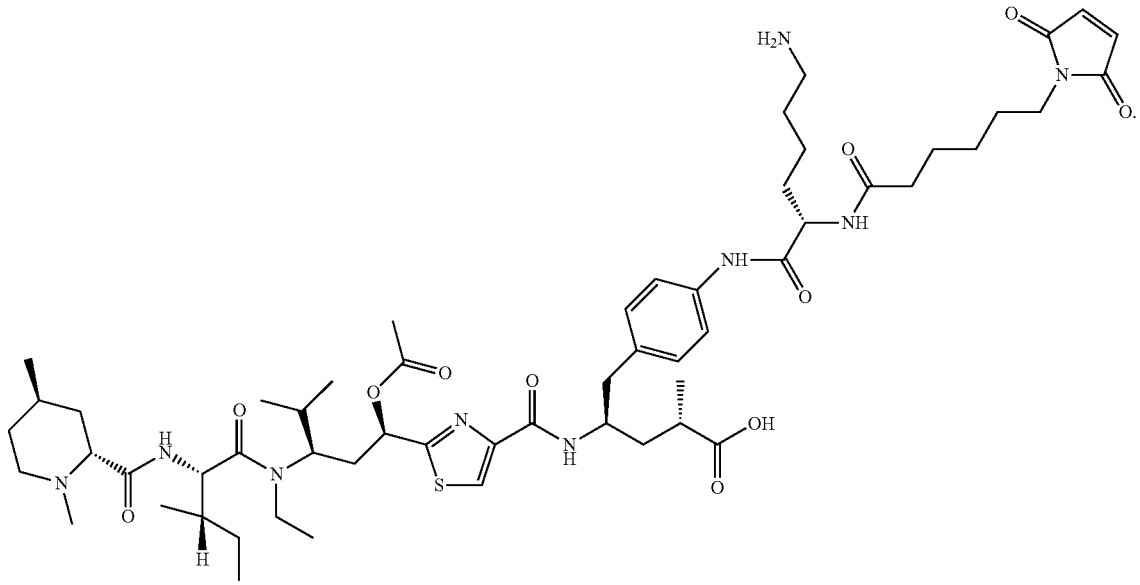 [SMILES: CC[C@H](C)[C@H](NC(=O)[C@H]1C[C@H](C)CCN1C)C(=O)N(CC)[C@H](C[C@@H](OC(C)=O)c1nc(C(=O)N[C@@H](Cc2ccc(NC(=O)[C@H](CCCCN)NC(=O)CCCCCN3C(=O)C=CC3=O)cc2)C[C@H](C)C(=O)O)cs1)C(C)C]

To the resin intermediate 76 (0.2 g, 0.32 mmol) was added DCM (1 mL), and TFA (1 mL) at room temperature. The mixture was shaken at room temperature for 20 min, and was filtered. The resin was washed with DCM/TFA (1:1, 3×2 mL), the combined filtrates were evaporated in vacuo. The residue was purified by reverse phase HPLC (ACN/water 0.1% TFA, ACN from 5% to 75% in 14 min). The pure fractions were lyophilized to give (2S,4R)-4-(2-((1R,3R)-1-acetoxy-3-((2S,3S)-2-((2R,4R)-1,4-dimethylpiperidine-2-carboxamido)-N-ethyl-3-methylpentanamido)-4-methyl-pentyl)thiazole-4-carboxamido)-5-(4-((S)-6-amino-2-(6-(2,5-dioxo-2,5-dihydro-1H-pyrrol-1-yl)hexanamido)hexanamido)phenyl)-2-methylpentanoic acid (0.095 g, 22.48%) as a white solid. LC-MS: 1092 [M+1]; $^1$H NMR (400 MHz, METHANOL-d4) δ ppm 7.99 (s, 1H), 7.34 (d, J=8.53 Hz, 2H), 7.10 (d, J=8.53 Hz, 2H), 6.66 (s, 2H), 5.64 (d, J=10.79 Hz, 1H), 4.50-4.61 (m, 1H), 4.21-4.35 (m, 2H), 3.92 (d, J=9.29 Hz, 1H), 3.69 (br. s., 1H), 3.37 (t, J=7.15 Hz, 2H), 3.15-3.35 (m, 4H), 3.04 (dt, J=3.58, 1.85 Hz, 1H), 2.84 (t, J=7.65 Hz, 2H), 2.76 (d, J=7.03 Hz, 2H), 2.62 (br. s., 2H), 2.38-2.52 (m, 2H), 2.25 (t, J=11.54 Hz, 1H), 2.16 (t, J=7.40 Hz, 2H), 2.04-2.11 (m, 4H), 1.70-2.00 (m, 7H) 1.42-1.69 (m, 11H), 1.34-1.40 (m, 1H), 1.27 (t, J=6.78 Hz, 3H), 1.16-1.24 (m, 2H), 1.01-1.14 (m, 7H), 0.90 (d, J=6.78 Hz, 3H), 0.94 (d, J=6.53 Hz, 3H), 0.84 (t, J=7.40 Hz, 3H), 0.79 (d, J=6.53 Hz, 3H).

Intermediate 77

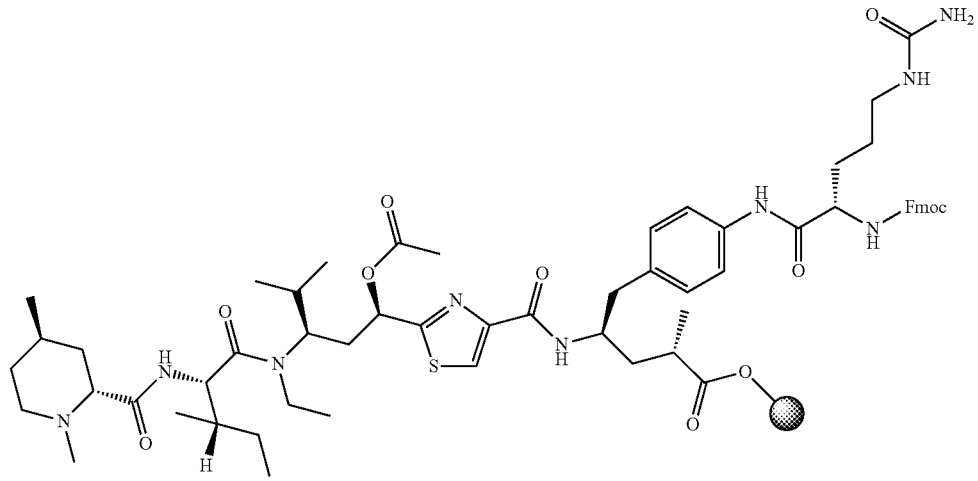

To the resin intermediate 28 was added a solution of (S)-2-((((9H-fluoren-9-yl)methoxy)carbonyl)amino)-5-ureidopentanoic acid (3.88 g, 9.76 mmol), HATU (3.71 g, 9.76 mmol), 2,4,6-trimethylpyridine (2.59 mL, 19.52 mmol) and DIEA (3.41 mL, 19.52 mmol) in DMF (38 mL). The mixture was shaken at room temperature for 2 hours, the resulting resin was filtered, washed with DMF (3×100 mL), MeOH (3×100 mL), and DCM (3×100 mL), and dried in vacuo. Small amount of the compound was cleaved from resin, analyzed by LCMS, which indicated the reaction was complete. The resulting resin intermediate 77 was used for next step reaction. LC-MS: 1150 (M+1).

Intermediate 78

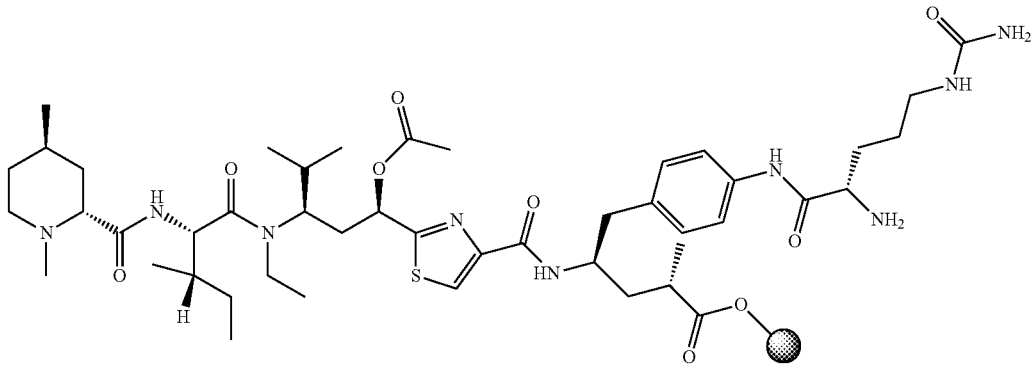 [SMILES: CC[C@H](C)[C@H](NC(=O)[C@H]1C[C@H](C)CCN1C)C(=O)N(CC)[C@H](C[C@@H](OC(C)=O)c1nc(C(=O)N[C@@H](Cc2ccc(NC(=O)[C@@H](N)CCCNC(N)=O)cc2)C[C@H](C)C(=O)OC)cs1)C(C)C]

To the resin intermediate 77 was added a solution of 20% piperidine in DMF (35 mL). The mixture was shaken at room temperature for six minutes. The resulting resin was filtered, washed with DMF (3×100 mL), MeOH (3×100 mL), and DCM (3×100 mL), and dried in vacuo. Small amount of the compound was cleaved from resin, analyzed by LCMS and showed weak signal. The resulting resin intermediate 78 was used for next step reaction. LC-MS: 928 (M+1).

Intermediate 79

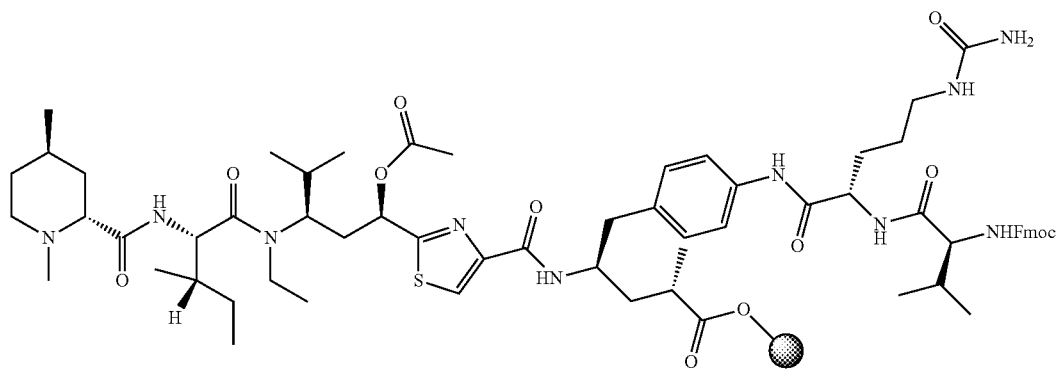

To the resin intermediate 78 was added a solution of (S)-2-((((9H-fluoren-9-yl)methoxy)carbonyl)amino)-3-methylbutanoic acid (1.529 g, 4.50 mmol), HATU (1.713 g, 4.50 mmol), 2,4,6-trimethylpyridine (1.294 mL, 9.76 mmol) and DIPEA (1.705 mL, 9.76 mmol) in DMF (20 mL). The mixture was shaken at room temperature for 2 hours, the resulting resin was filtered, washed with DMF (3×75 mL), MeOH (3×75 mL), and DCM (3×75 mL), and dried in vacuo. Small amount of the compound was cleaved from resin, analyzed by LC/MS, which indicated the reaction was completed. The resulting resin intermediate 79 was used in next step reaction. LC-MS: 1250 (M+1).

Intermediate 80

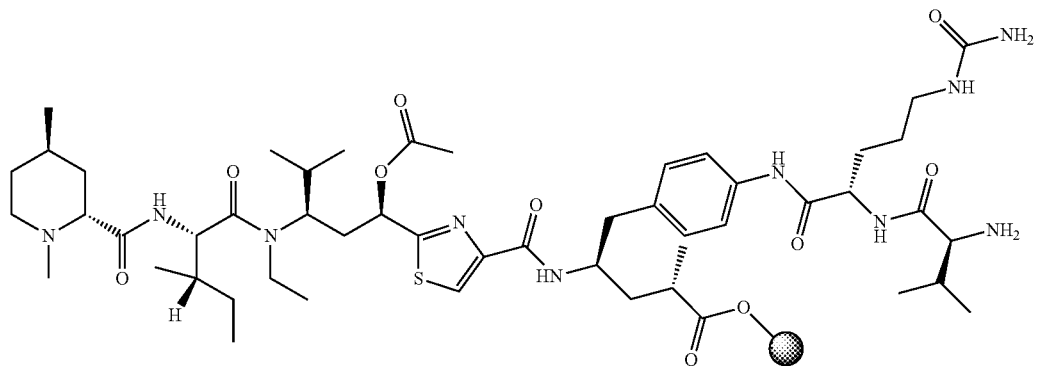 [SMILES: CC[C@H](C)[C@H](NC(=O)[C@H]1C[C@H](C)CCN1C)C(=O)N(CC)[C@H](C[C@@H](OC(C)=O)c1nc(C(=O)N[C@@H](Cc2ccc(NC(=O)[C@H](CCCNC(N)=O)NC(=O)[C@@H](N)C(C)C)cc2)C[C@H](C)C(=O)OC)cs1)C(C)C]

To the resin intermediate 79 was added a solution of 20% piperidine in DMF (20 mL). The mixture was shaken at room temperature for six min, and the resulting resin was filtered, washed with DMF (3×75 mL), MeOH (3×75 mL), and DCM (3×75 mL), and dried in vacuo. Small amount of the compound was cleaved from resin, analyzed by LCMS, which indicated the reaction was completed. The resulting resin intermediate 80 was used for next step reaction. LC/MS: 1028 (M+1).

Intermediate 81

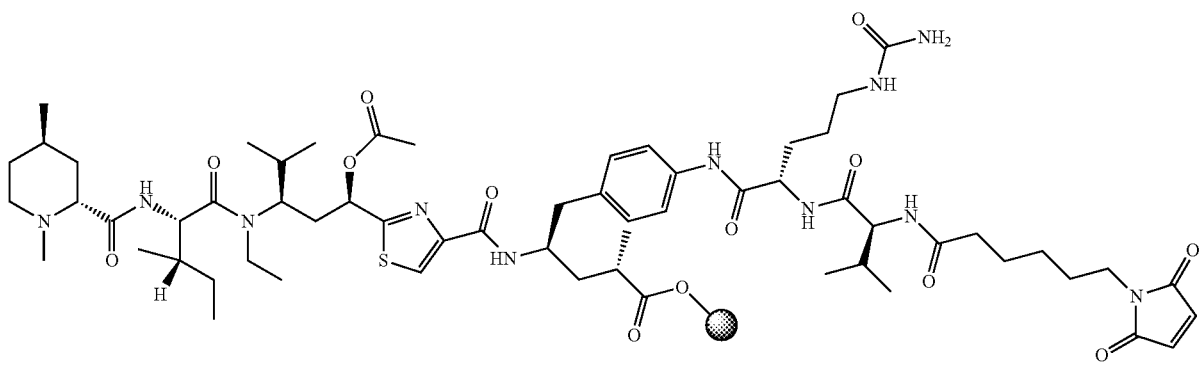 [SMILES: CC[C@H](C)[C@H](NC(=O)[C@H]1C[C@H](C)CCN1C)C(=O)N(CC)[C@H](C[C@@H](OC(C)=O)c1nc(C(=O)N[C@@H](Cc2ccc(NC(=O)[C@H](CCCNC(N)=O)NC(=O)[C@@H](NC(=O)CCCCCN3C(=O)C=CC3=O)C(C)C)cc2)C[C@H](C)C(=O)OC)cs1)C(C)C]

To the resin intermediate 80 was added the solution of 2,5-dioxopyrrolidin-1-yl 6-(2,5-dioxo-2,5-dihydro-1H-pyrrol-1-yl)hexanoate (1.157 g, 3.75 mmol) in DMF (18 mL), followed by 4-methylmorpholine (1.032 mL, 9.38 mmol) at room temperature. The mixture was shaken at room temperature for 2 hours and the resulting resin was filtered, washed with DMF (3×75 mL), MeOH (3×75 mL), and DCM (3×75 mL), and dried in vacuo. A small amount of resin was cleaved by adding TFA and analyzed by LC/MS and indicated formation of desired product. The resin intermediate 81 was used for the next step. LC-MS: 1220 (M+1).

Compound 8

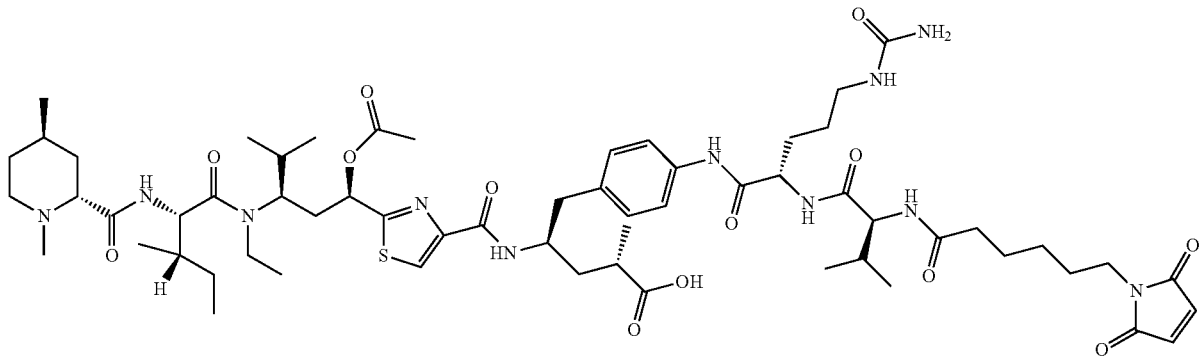 [SMILES: CC[C@H](C)[C@H](NC(=O)[C@H]1C[C@H](C)CCN1C)C(=O)N(CC)[C@H](C[C@@H](OC(C)=O)c1nc(C(=O)N[C@@H](Cc2ccc(NC(=O)[C@H](CCCNC(N)=O)NC(=O)[C@@H](NC(=O)CCCCCN3C(=O)C=CC3=O)C(C)C)cc2)C[C@H](C)C(=O)O)cs1)C(C)C]

To the resin from 81 was added a solution of TFA (2.89 mL, 37.54 mmol) in DCM (40 mL). The mixture was shaken at room temperature for 5 minutes, the resulting resin was filtered, was washed with additional 50 mL DCM. The combined extracts were concentrated. The crude material was purified by reverse phase HPLC (C18 Column, 0.1% TFA/water/0.1 TFA acetonitrile, 0-40%, 30 minutes method). The pure fractions were lyophilized to give (2S,4R)-4-(2-((1R,3R)-1-acetoxy-3-((2S,3S)-2-((2R,4R)-1,4-dimethylpiperidine-2-carboxamido)-N-ethyl-3-methylpentanamido)-4-methylpentyl)thiazole-4-carboxamido)-5-(4-((S)-2-((S)-2-(6-(2,5-dioxo-2,5-dihydro-1H-pyrrol-1-yl)hexanamido)-3-methylbutanamido)-5-ureidopentanamido)phenyl)-2-methylpentanoic acid (0.620 g, 12.38%) as white solid. LC-MS: 1220 (M+1); $^1$H NMR (400 MHz, CD$_3$OD) δ ppm 8.03 (s, 1H), 7.30-7.44 (m, 2H), 7.07 (d, J=8.53 Hz, 2H), 6.69 (s, 2H), 5.53-5.68 (m, 1H), 4.52-4.63 (m, 1H), 4.19-4.40 (m, 3H), 4.01-4.12 (m, 2H), 3.89-3.99 (m, 1H), 3.56-3.74 (m, 1H), 3.33-3.43 (m, 2H), 3.23-3.32 (m, 1H), 2.96-3.13 (m, 4H), 2.83-2.95 (m, 1H), 2.66-2.83 (m, 3H), 2.57 (br. s., 3H), 2.40-2.52 (m, 2H), 2.14-2.24 (m, 3H), 2.02-2.11 (m, 4H), 1.87-2.00 (m, 5H), 1.72-1.87 (m, 4H), 1.42-1.68 (m, 10H), 1.16-1.28 (m, 5H), 1.09 (d, J=7.03 Hz, 6H) 0.76-0.96 (m, 16H).

Intermediate 82

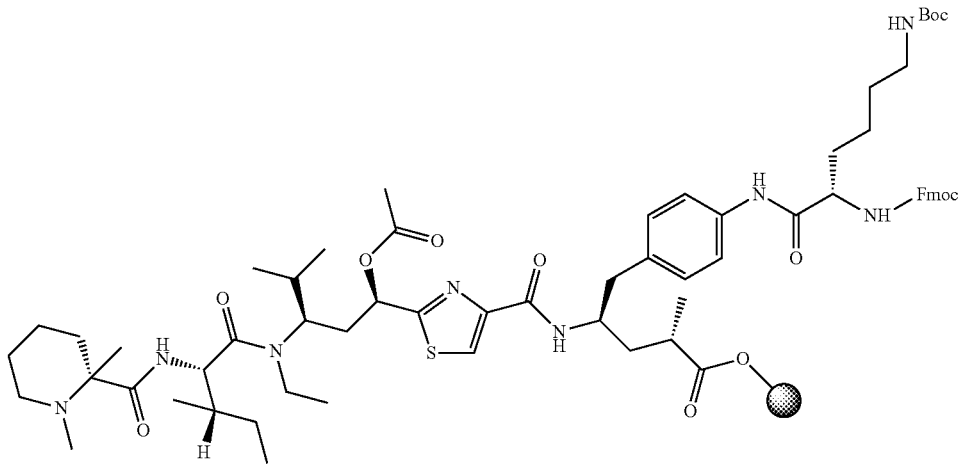

To the resin intermediate 38 (0.35 g, 0.56 mmol) was added a solution of (S)-2-((((9H-fluoren-9-yl)methoxy)carbonyl)amino)-6-((tert-butoxycarbonyl)amino)hexanoic acid (0.525 g, 1.12 mmol), HATU (0.426 g, 1.12 mmol), 2,4,6-trimethylpyridine (0.223 mL, 1.68 mmol) and DIPEA (0.293 mL, 1.68 mmol) in DMF (5 mL) The mixture was shaken at room temperature for 2 hours, the resulting resin was filtered, washed with DMF (3×5 mL), MeOH (3×5 mL), and DCM (3×5 mL), and dried in vacuo. Small amount of the compound was cleaved from resin, analyzed by LCMS, which indicated the reaction was completed. The resulting resin intermediate 82 was used for the next step reaction. LC/MS: 1221 (M+1).

Intermediate 83

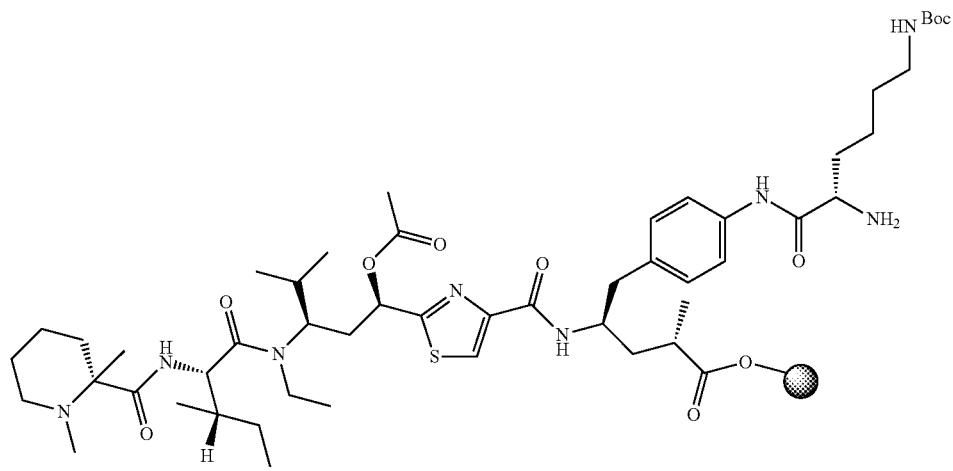 [SMILES: CC[C@H](C)[C@H](NC(=O)[C@@]1(C)CCCCN1C)C(=O)N(CC)[C@H](C[C@@H](OC(C)=O)c1nc(C(=O)N[C@@H](Cc2ccc(NC(=O)[C@@H](N)CCCCN)cc2)C[C@H](C)C(=O)OC)cs1)C(C)C]

To the resin intermediate 82 was added 20% piperidine in DMF (4 mL). The mixture was shaken at room temperature for 6 min and the resulting resin was filtered, washed with DMF (3×5 mL), MeOH (3×5 mL), DCM (3×5 mL), and was dried in vacuo. Small amount of the compound was cleaved from resin, analyzed by LC/MS, which indicated the reaction was completed. The resulting resin intermediate 83 was used to next step reaction. LC/MS: 999 (M+1).

Intermediate 84

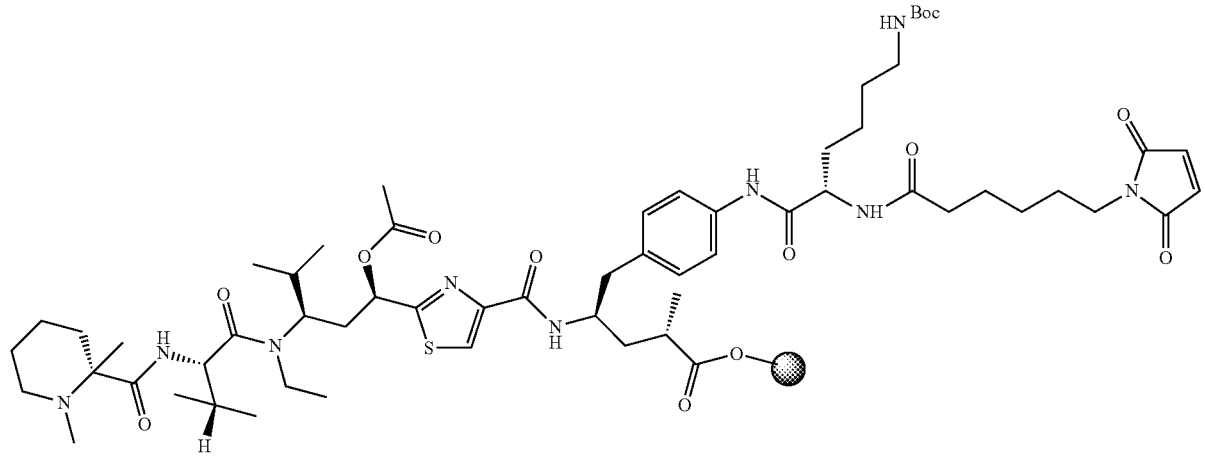

To the resin intermediate 83 was added the solution of 2,5-dioxopyrrolidin-1-yl 6-(2,5-dioxo-2,5-dihydro-1H-pyrrol-1-yl)hexanoate (0.259 g, 0.84 mmol) in DCM (4 mL), followed by 4-methylmorpholine (0.185 mL, 1.68 mmol) at room temperature. The mixture was shaken at room temperature for 6 hours, the resulting resin was filtered, washed with DMF (3×5 mL), MeOH (3×5 mL), DCM (3×5 mL), dried in vacuo. Small amount of the compound was cleaved from resin, analyzed by LC/MS, which indicated the reaction was completed. The resulting resin intermediate 84 was used in next step reaction. LC-MS: 1192 (M+1).

Intermediate 85

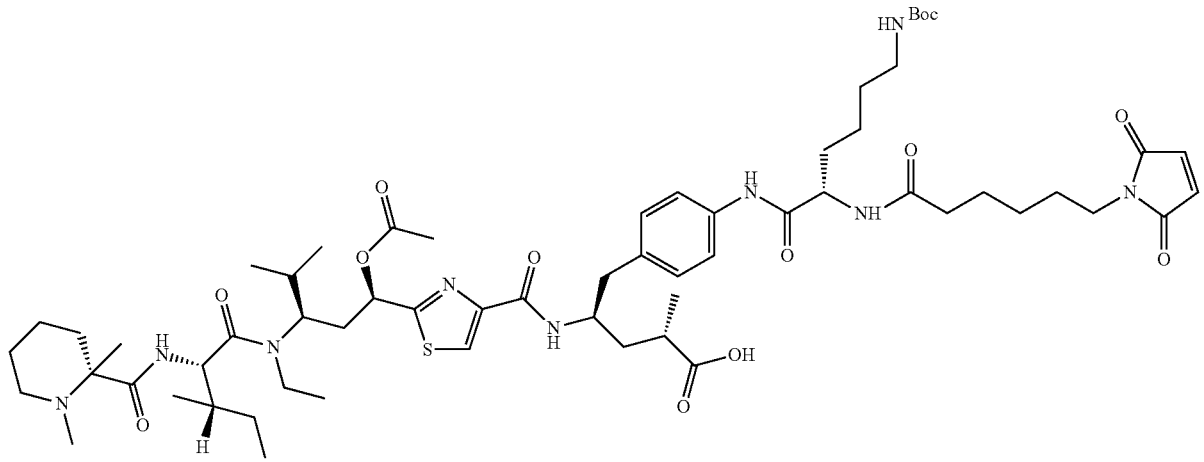 [SMILES: CC[C@H](C)[C@H](NC(=O)[C@@]1(C)CCCCN1C)C(=O)N(CC)[C@H](C[C@@H](OC(C)=O)c1nc(C(=O)N[C@@H](Cc2ccc(NC(=O)[C@H](CCCCN)NC(=O)CCCCCN3C(=O)C=CC3=O)cc2)C[C@H](C)C(=O)O)cs1)C(C)C]

To the resin intermediate 84 (0.35 g, 0.56 mmol) was added TFA (0.216 mL, 2.80 mmol) in DCM (5 mL). The mixture was shaken at room temperature for 10 minutes. The solvent was removed under reduced pressure. The residue was dissolved in DMSO and purified by reverse phase HPLC (0.1 TFA/water/acetonitrile, 20-80%, 14 minutes). Fractions containing pure product were lyophilized to give (2S,4R)-4-(2-((1R,3R)-1-acetoxy-3-((2S,3S)-2-(1,2-dimethylpiperidine-2-carboxamido)-N-ethyl-3-methylpentanamido)-4-methylpentyl)thiazole-4-carboxamido)-5-(4-((S)-6-((tert-butoxycarbonyl)amino)-2-(6-(2,5-dioxo-2,5-dihydro-1H-pyrrol-1-yl)hexanamido)hexanamido)phenyl)-2-methylpentanoic acid (0.123 g, 18.42%) as a white solid. LC/MS: 1192 (M+1).

Compound 9

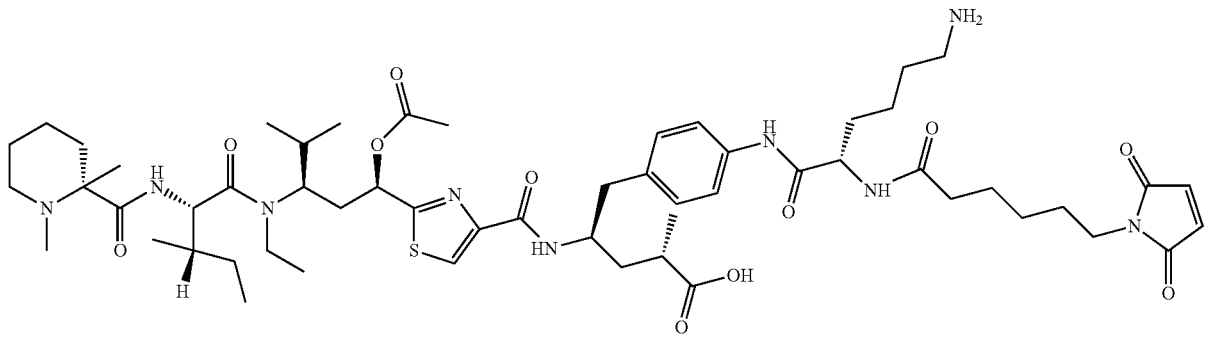 [SMILES: CC[C@H](C)[C@H](NC(=O)[C@@]1(C)CCCCN1C)C(=O)N(CC)[C@H](C[C@@H](OC(C)=O)c1nc(C(=O)N[C@@H](Cc2ccc(NC(=O)[C@H](CCCCN)NC(=O)CCCCCN3C(=O)C=CC3=O)cc2)C[C@H](C)C(=O)O)cs1)C(C)C]

To intermediate 85 (95 mg, 0.08 mmol) was added the solution of TFA (0.123 mL, 1.59 mmol) in DCM (1 mL). The mixture was shaken at room temperature for 1 hour. The solvent was removed under reduced pressure. The residue was dissolved in DMSO and purified by reverse phase HPLC (0.1 TFA/water/acetonitrile, 10-70%, 10 minutes). Fractions containing pure product were lyophilized to give (2S,4R)-4-(2-((1R,3R)-1-acetoxy-3-((2S,3S)-2-((R)-1,2-dimethylpiperidine-2-carboxamido)-N-ethyl-3-methylpentanamido)-4-methylpentyl)thiazole-4-carboxamido)-5-(4-((S)-6-amino-2-(6-(2,5-dioxo-2,5-dihydro-1H-pyrrol-1-yl)hexanamido)hexanamido)phenyl)-2-methylpentanoic acid (53.0 mg, 50.4%) as a white solid. LC-MS: 1092 (M+1).; $^1$H NMR (400 MHz, CD$_3$OD) δ ppm 7.97 (s, 1H), 7.36 (d, J=8.28 Hz, 2H), 7.11 (d, J=8.28 Hz, 2H), 6.65 (s, 2H), 5.63 (d, J=11.29 Hz, 1H), 4.34 (dd, J=8.28, 5.77 Hz, 1H), 4.26 (br. s., 1H), 3.75-3.60 (m, 1H), 3.32-3.46 (m, 4H), 3.30-3.25 (m, 1H), 2.71-2.90 (m, 5H), 2.49-2.62 (m, 3H), 2.27 (t, J=12.05 Hz, 1H), 2.17 (t, J=7.40 Hz, 3H) 2.00-2.12 (m, 5H), 1.84-1.96 (m, 3H), 1.72-1.84 (m, 4H), 1.58-1.69 (m, 5H), 1.47-1.56 (m, 4H), 1.36-1.44 (m, 5H), 1.14-1.30 (m, 6H), 1.01-1.10 (m, 4H), 0.93 (dd, J=13.93, 6.65 Hz, 7H), 0.74-0.86 (m, 7H).

Intermediate 86

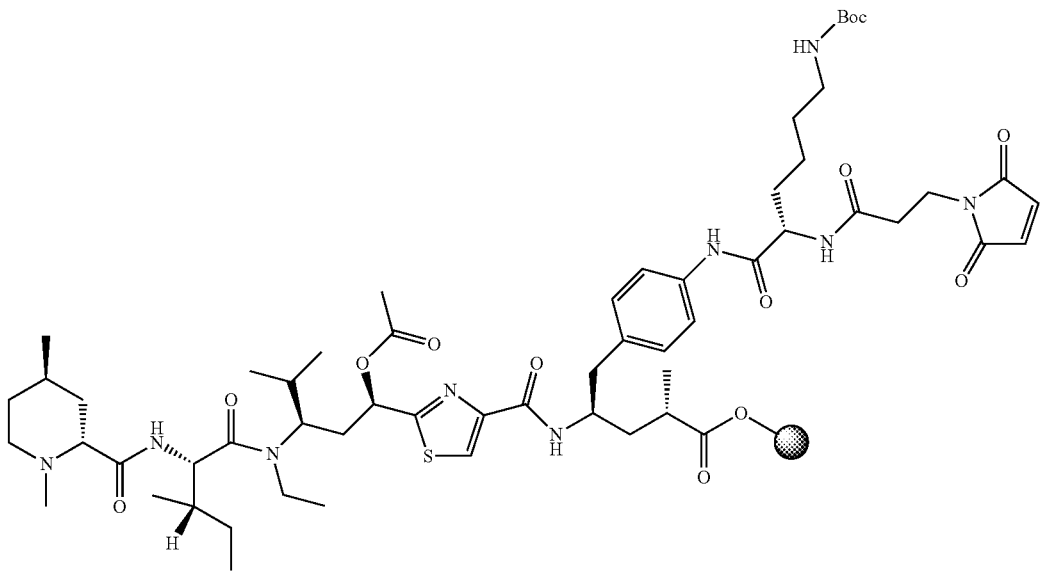 [SMILES: CC[C@H](C)[C@H](NC(=O)[C@H]1C[C@H](C)CCN1C)C(=O)N(CC)[C@H](C[C@@H](OC(C)=O)c1nc(C(=O)N[C@@H](Cc2ccc(NC(=O)[C@H](CCCCNC(=O)OC(C)(C)C)NC(=O)CCN3C(=O)C=CC3=O)cc2)C[C@H](C)C(=O)OC)cs1)C(C)C]

To the resin intermediate 75 (0.20 g, 0.16 mmol) was added a solution of 2,5-dioxopyrrolidin-1-yl-3-(2,5-dioxo-2,5-dihydro-1H-pyrrol-1-yl)propanoate (85 mg, 0.32 mmol) in DCM, followed by DIEA (0.056 mL, 0.32 mmol) at room temperature. The mixture was shaken at room temperature for 4 hours, the resulting resin was washed with DMF (3×3 mL), DCM (3×3 mL), and MeOH (3×3 mL) and was dried under vacuum. Small amount of compound was cleaved from the resin with TFA/DCM (1:2). After the solvent was evaporated, the crude product was analyzed by LC/MS. LC/MS indicated that the coupling reaction was completed. LC/MS: 1050.37 (M+1).

Compound 10

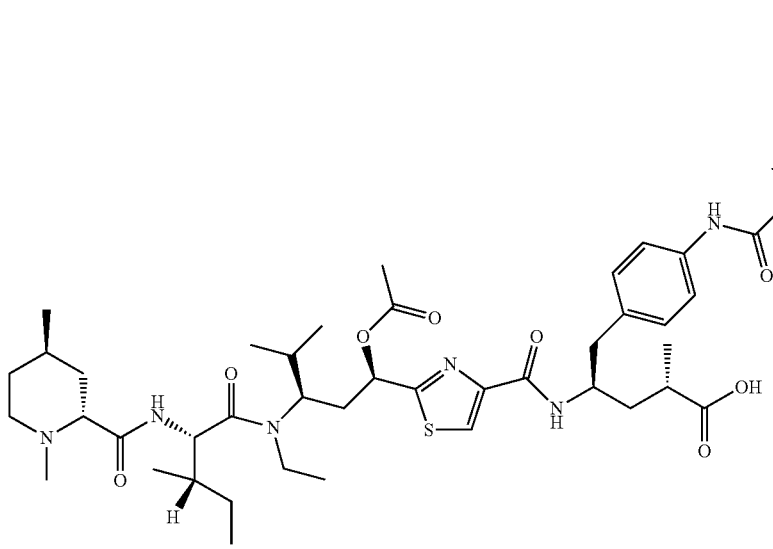

To the resin intermediate 86 (0.20 g, 0.16 mmol) was added TFA/DCM (1:2, 3 mL) at room temperature. The mixture was shaken at room temperature for 10 min, and filtrated. The resin was washed with DCM (3×3 mL), all the filtrates were combined and were evaporated under reduced pressure to give a crude product. The crude product was purified by reverse phase HPLC ($H_2O$ and $CH_3CN$ with 0.1% TFA, $CH_3CN$ from 5% t0 40% in length of 12 CV). The collected fractions were combined and lyophilized to give (2S,4R)-4-(2-((1R,3R)-1-acetoxy-3-((2S,3S)-2-((2R,4R)-1,4-dimethylpiperidine-2-carboxamido)-N-ethyl-3-methylpentanamido)-4-methylpentyl)thiazole-4-carboxamido)-5-(4-((S)-6-amino-2-(3-(2,5-dioxo-2,5-dihydro-1H-pyrrol-1-yl)propanamido)hexanamido)phenyl)-2-methylpentanoic acid as a white powder (70 mg, 35%). LC/MS: 1050.37 (M+1); $^1$H NMR (400 MHz, Methanol-$d_4$) δ 7.99 (s, 1H), 7.35 (d, J=8.5 Hz, 2H), 7.10 (d, J=8.5 Hz, 2H), 6.65 (s, 2H), 5.64 (d, J=10.9 Hz, 1H), 4.56 (d, J=8.9 Hz, 1H), 4.28 (td, J=11.3, 10.0, 6.1 Hz, 2H), 3.92 (d, J=11.5 Hz, 1H), 3.69 (q, J=6.8 Hz, 3H), 3.31-3.23 (m, 1H), 3.18 (s, 1H), 2.83 (t, J=7.7 Hz, 3H), 2.76 (d, J=7.1 Hz, 3H), 2.63 (s, 3H), 2.50-2.40 (m, 4H), 2.25 (t, J=12.8 Hz, 1H), 2.06 (s, 4H), 2.00-1.69 (m, 8H), 1.69-1.52 (m, 6H), 1.53-1.31 (m, 4H), 1.28 (d, J=6.4 Hz, 3H), 1.08 (d, J=7.1 Hz, 7H), 0.92 (dd, J=13.7, 6.7 Hz, 7H), 0.83 (t, J=7.4 Hz, 4H), 0.78 (d, J=6.6 Hz, 3H).

General Description of Conjugation

ADCs containing antibodies may be prepared by standard methods such as, but not limited to aldehyde/Schiff linkage, sulfhydryl linkage, acid-labile linkage, cis-aconityl linkage, hydrazone linkage, by methods analogous to those described by Hamblett, *Clin. Cancer Res.* 2004, 10, 7063-7070; Doronina et al., *Nat. Biotechnol.* 2003, 21(7), 778-784 and Francisco et al., *Blood*, 2003, 102, 1458-1465, and appropriate modification of the following non-limiting example.

Antibody is treated by under reducing conditions using 40 molar equivalent TCEP in PBS pH 7.2 and 1 mM EDTA for 3 hours at 37° C. to remove thiol-reactive species such as cysteine, glutathione, metals and reduce the interchain disulfide bonds in the antibody. This step is followed by two rounds of dialysis in PBS pH 7.2, 1 mM EDTA at 4° C. using 10,000 MWCO dialysis cassettes (Thermo Scientific). The disulfide bonds are reformed by oxidation with dehydroascorbic acid over the antibody for 4 hours at 25° C. in PBS pH 7.2, 1 mM EDTA. Thereafter, 20 molar equivalents of compound of Formula II is conjugated via the reactive thiol group of the antibody by incubating for 1 hour at 25° C. in PBS pH 7.2, 1 mM EDTA, 10% v/v DMSO (Dimethyl sulfoxide) (Thermo Scientific). The conjugates are purified by filtration. The conjugation reaction is quenched by adding 4 molar equivalents of N-acetyl cysteine (Sigma-Aldrich). The antibody-drug conjugates is dialyzed at 4° C. overnight using 20K MWCO cassette in 5 mM NaP04, pH 6, and subsequently purified using 5 mL ceramix hydroxyapatite (CHT) type II cartridge (Biorad). The conjugates are eluted from the cartridge using 10 mM NaP04 pH 6 and a 0 to 2 M NaCl linear gradient and can be concentrated and formulated by buffer exchange using dialysis in 20 mM Histidine-HCl, pH 6.0.

In Vitro Proliferation Assay

A panel of human cancer cell lines (DU 145, NCI-N87, and MDA-MB-361) obtained from the American Type Tissue Collection (ATCC) (P.O. Box 1549, Manassa, Va. 20108 (USA)) were used to determine the relative cytotoxicity of tubulysin compounds of the invention. The cells were plated in culture media at a density of 2,000 to 5,000 per well of tissue-culture-treated 96-well plates in a volume of 80 µl and allowed to adhere overnight. A 5× concentration of each compound tested was prepared by diluting the test articles in culture medium. Twenty microliters of each test article was added to cells in duplicate or triplicate such that the final dose curve ranged from 4 µg/ml down to 61 pg/ml in a stepwise 1:4 serial dilution series. The treated cells were cultured at 37° C./5% $CO_2$ for 72 to 144 hours. The CellTiter-Glo Luminescent Viability Assay from Promega was used to determine relative cytotoxicity. Briefly, 100 µl of CellTiter-Glo reagent was added to each well, allowed to incubate for 10 minutes at room temperature with mild shaking and then the absorbance of each sample at 560 nM was read using a Perkin Elmer EnVision luminometer. The percent cell viability was calculated by the following formula: (average luminescence of treated samples/average luminescence of control (untreated) samples)×100. $IC_{50}$ values were determined using logistic non-linear regression analysis with GraphPad Prism software. Not all compounds were assayed against all cell lines. Table I provides data for the assay.

TABLE I

| Compound | DU145 IC50 (nM) | HCT116 IC50 (nM) | MB231 IC50 (nM) |
| --- | --- | --- | --- |
| Compound 1 | 0.2 | .6 | 2.5 |
| Compound 2 | 0.5 | ND | ND |
| Compound 3 | 0.2 | ND | ND |
| Compound 4 | 1.3 | 1.8 | 3.9 |
| Compound 5 | 0.9 | 0.5 | 3.4 |
| Compound 6 | 4 | 1.9 | 6.6 |

All references cited herein, including patents, patent applications, papers, text books, and the like, and the references cited therein, to the extent that they are not already, are hereby incorporated herein by reference in their entirety for all purposes.

What is claimed is:

1. A compound having the structure of Formula I:

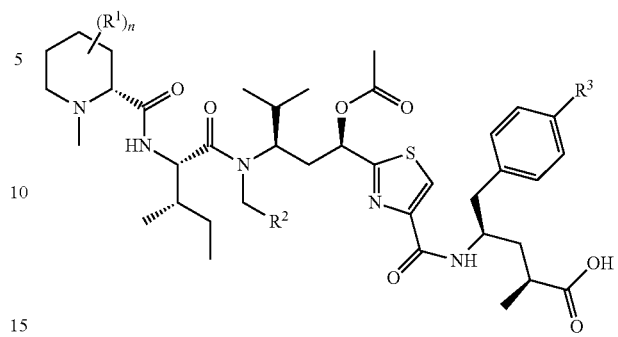

or a pharmaceutically acceptable salt thereof, wherein:
$R^1$ is $CH_3$ or $CH_2CH_3$,
$R^2$ is H or $CH_3$,
$R^3$ is H or $NH_2$ and
n is 1 or 2.

2. A compound of claim 1 wherein n is 1 and $R^1$ is methyl.
3. A compound of claim 1 wherein $R^2$ is methyl.
4. A compound of claim 1 wherein $R^3$ is $NH_2$.
5. A compound of claim 1 wherein n is 1, $R^1$ is methyl, $R^2$ is methyl and $R^3$ is $NH_2$.
6. A compound of claim 1 having the Formula (Ii)

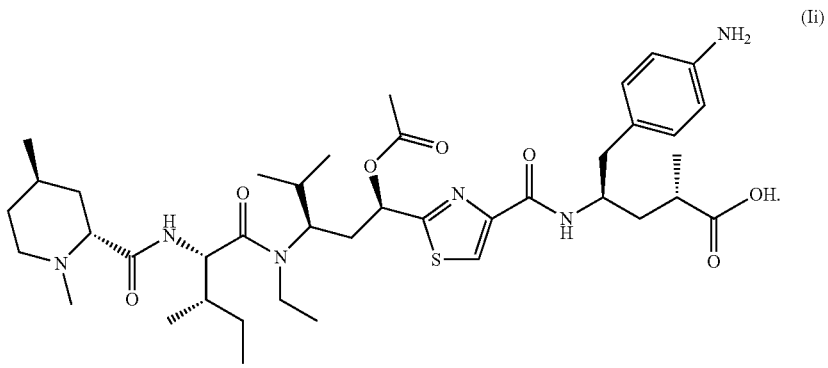 [SMILES: CC[C@H](C)[C@H](NC(=O)[C@H]1C[C@H](C)CCN1C)C(=O)N(CC)[C@H](C[C@@H](OC(C)=O)c1nc(C(=O)N[C@@H](Cc2ccc(N)cc2)C[C@H](C)C(=O)O)cs1)C(C)C]

7. A compound of claim 1 having the Formula (Iii)

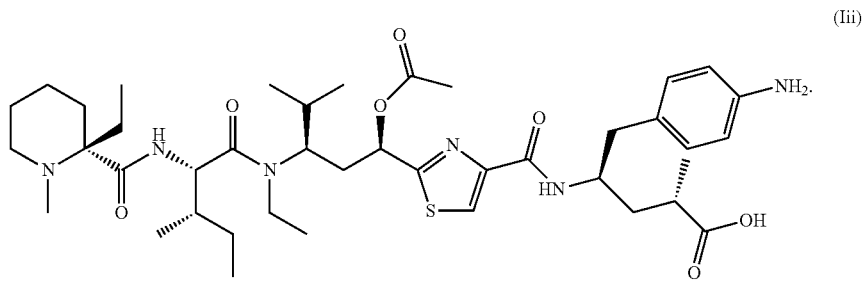 [SMILES: CC[C@H](C)[C@H](NC(=O)[C@@]1(CC)CCCCN1C)C(=O)N(CC)[C@H](C[C@@H](OC(C)=O)c1nc(C(=O)N[C@@H](Cc2ccc(N)cc2)C[C@H](C)C(=O)O)cs1)C(C)C]

8. A compound of claim 1 having the Formula (Iiii)
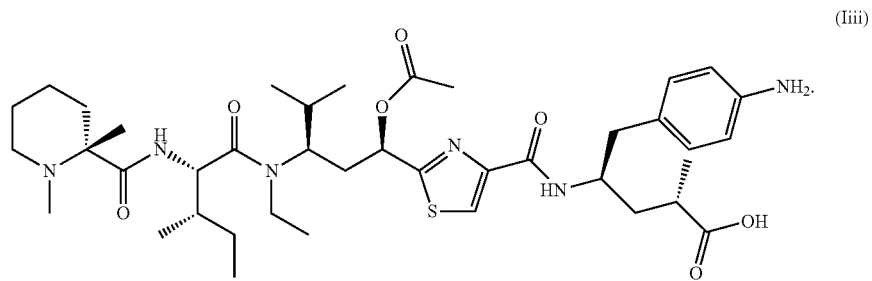 [SMILES: CC[C@H](C)[C@H](NC(=O)[C@@]1(C)CCCCN1C)C(=O)N(CC)[C@H](C[C@@H](OC(C)=O)c1nc(C(=O)N[C@@H](Cc2ccc(N)cc2)C[C@H](C)C(=O)O)cs1)C(C)C]
(Iiii)
9. A compound of claim 1 having the Formula (Iiv)
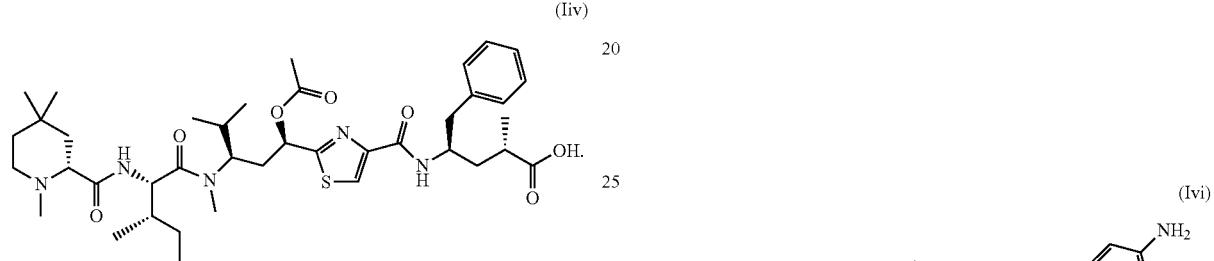
(Iiv)
10. A compound of claim 1 having the Formula (Iv)
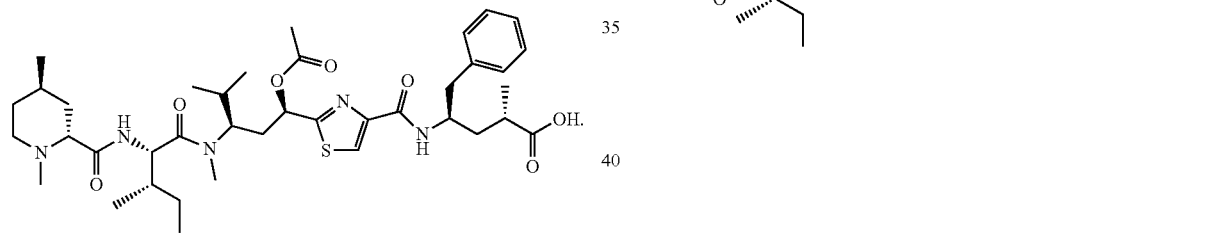
(Iv)
11. A compound of claim 1 having the Formula (Ivi)
12. A compound having the structure of Formula II
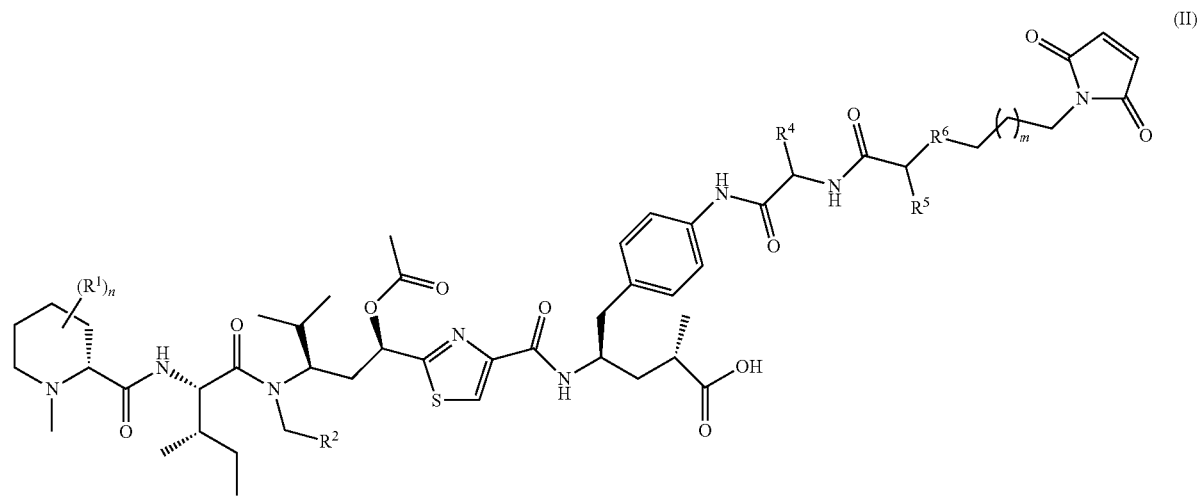
(II)
or a pharmaceutically acceptable salt thereof, wherein:
R¹ is $CH_3$ or $CH_2CH_3$,
R² is H or $CH_3$,
R⁴ is $CH_3$, $(CH_2)_4NH_2$, or $(CH_2)_3NHC(=O)NH_2$,
R⁵ is H or $CH(CH_3)(CH_3)$,
R⁶ is $NHC(=O)$ or $CH_2$,
n is 1 or 2; and
m is 0, 1, 2 or 3.

13. A compound of claim 12 wherein n is 1 and R¹ is methyl.

14. A compound of claim 12 wherein R² is methyl.

15. A compound of claim 12 wherein n is 1, R¹ is methyl, and R² is methyl.

16. A compound of claim 12 wherein R⁴ is $(CH_2)_4NH_2$.

17. A compound of claim 12 wherein R⁵ is H.

18. A compound of claim 12 wherein R⁶ is $CH_2$.

19. A compound of claim 12 wherein m is 1.

20. A compound of claim 12 wherein n is 1, m is 1, R¹ is methyl, R² is methyl, R⁴ is $(CH_2)_4NH_2$, R⁵ is H, and R⁶ is $CH_2$.

21. A compound of claim 12 having the Formula (IIi)

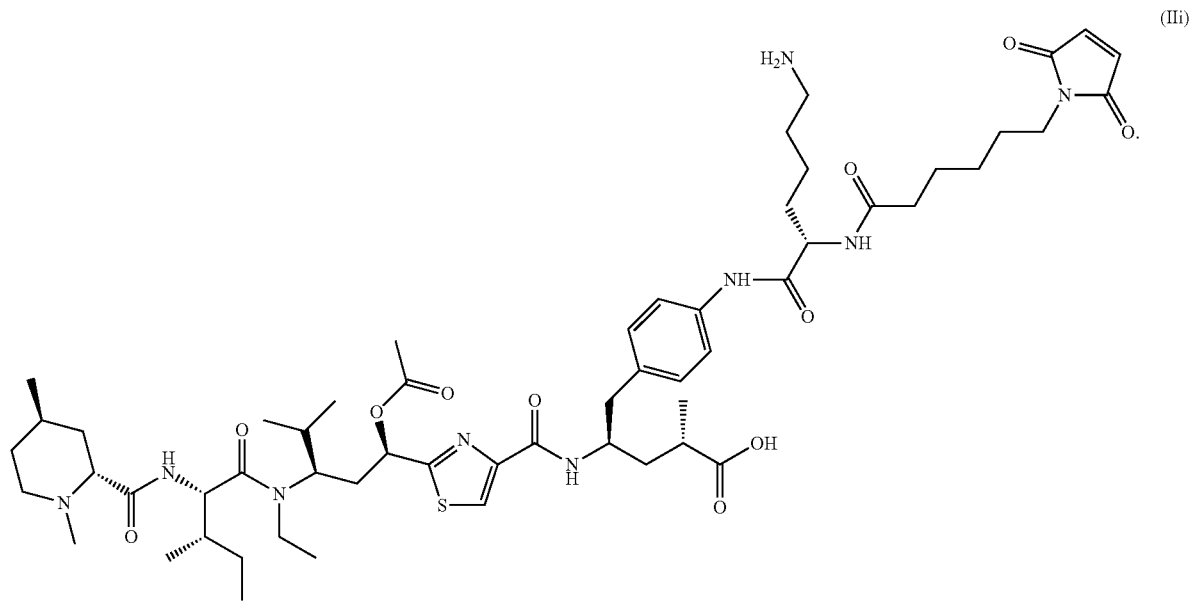 [SMILES: CC[C@H](C)[C@H](NC(=O)[C@H]1C[C@H](C)CCN1C)C(=O)N(CC)[C@H](C[C@@H](OC(C)=O)c1nc(C(=O)N[C@@H](Cc2ccc(NC(=O)[C@H](CCCCN)NC(=O)CCCCCN3C(=O)C=CC3=O)cc2)C[C@H](C)C(=O)O)cs1)C(C)C]

22. A compound of claim 12 having the Formula (IIii)

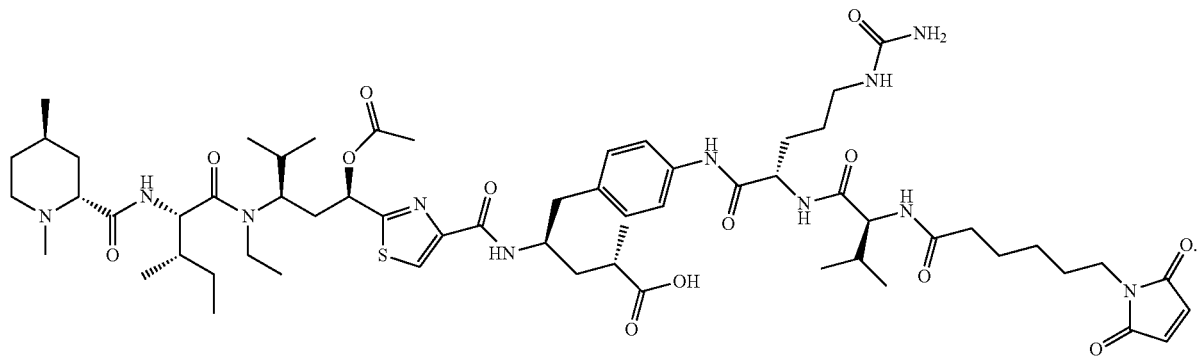

23. A compound of claim 12 having the Formula (IIiii)

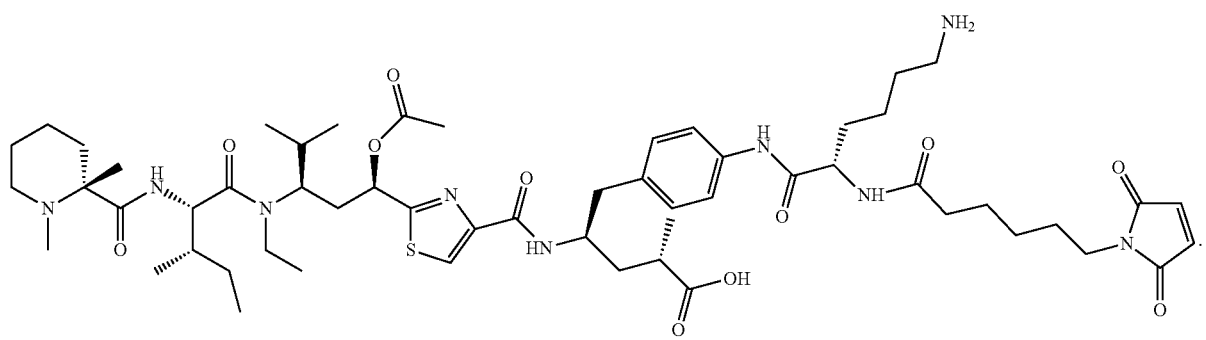

24. A antibody-drug conjugate which is a conjugate of a compound having the structure of Formula II

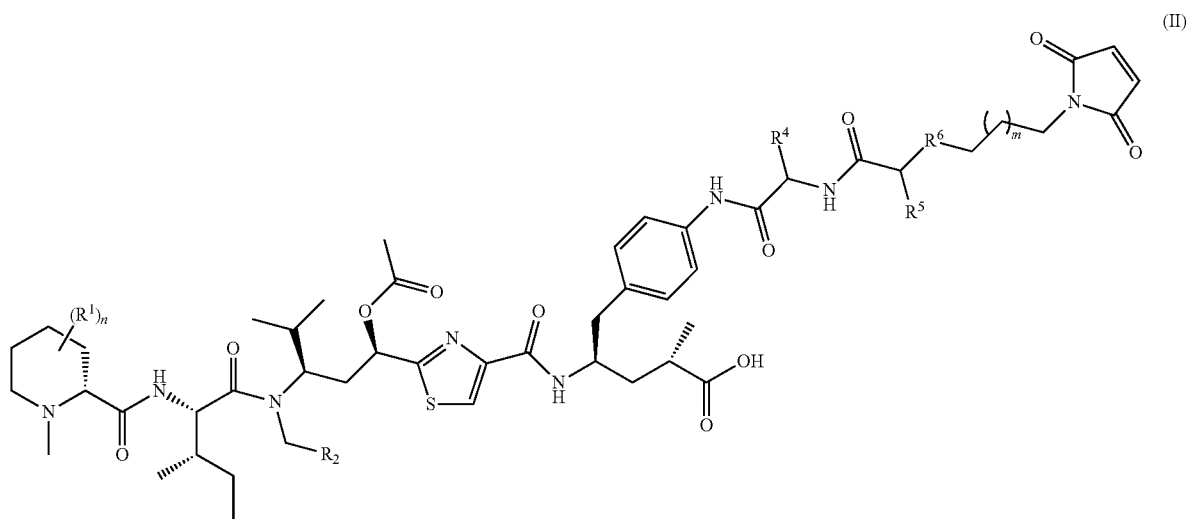

wherein:
$R^1$ is $CH_3$ or $CH_2CH_3$,
$R^2$ is H or $CH_3$,
$R^4$ is $CH_3$, $(CH_2)_4NH_2$, or $(CH_2)_3NHC(=O)NH_2$,
$R^5$ is H or $CH(CH_3)(CH_3)$,
$R^6$ is $NHC(=O)$ or $CH_2$,
n is 1 or 2; and
m is 0, 1, 2 or 3; and an antibody.

25. An antibody-drug conjugate of claim 24 wherein the antibody is a monoclonal antibody.

26. An antibody-drug conjugate of claim 24 wherein the antibody is specific to a cancer antigen.

27. An antibody-drug conjugate of claim 24 wherein the antibody is alemtuzumab, bevacizumab, brentuximab, cetuximab, gemtuzumab, ipilimumab, ofatumumab, panitumumab, rituximab, tositumomab, or trastuzumab.

28. An antibody-drug conjugate of claim 24 which is a conjugate of a compound of the Formula (IIi)

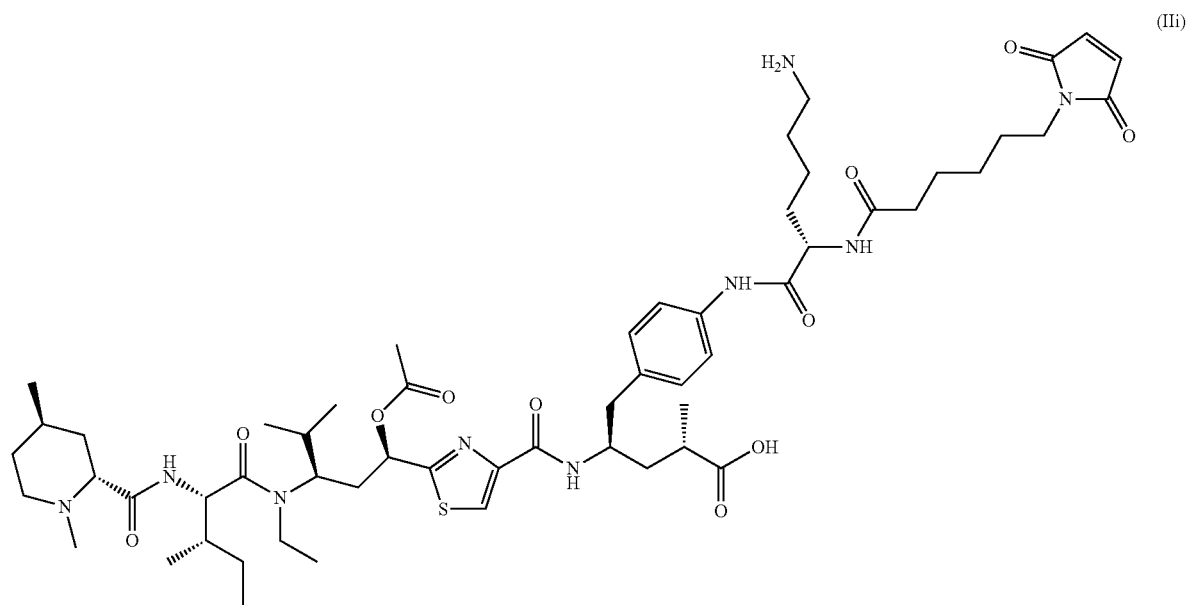 [SMILES: CC[C@H](C)[C@H](NC(=O)[C@H]1C[C@H](C)CCN1C)C(=O)N(CC)[C@H](C[C@@H](OC(C)=O)c1nc(C(=O)N[C@@H](Cc2ccc(NC(=O)[C@H](CCCCN)NC(=O)CCCCCN3C(=O)C=CC3=O)cc2)C[C@H](C)C(=O)O)cs1)C(C)C]

and an antibody.

29. An antibody-drug conjugate of claim 24 which is a conjugate of a compound of the Formula (IIii)

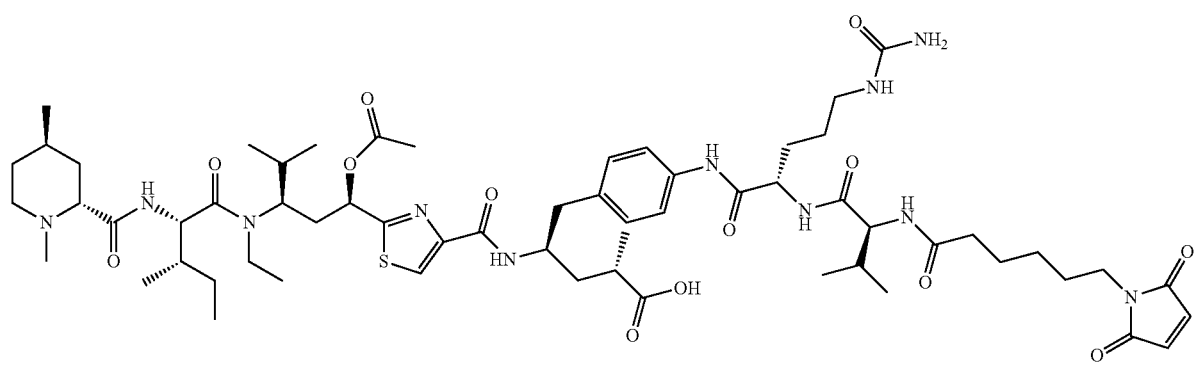

and an antibody.

30. An antibody-drug conjugate of claim 24 which is a conjugate of a compound of the Formula (IIiii)

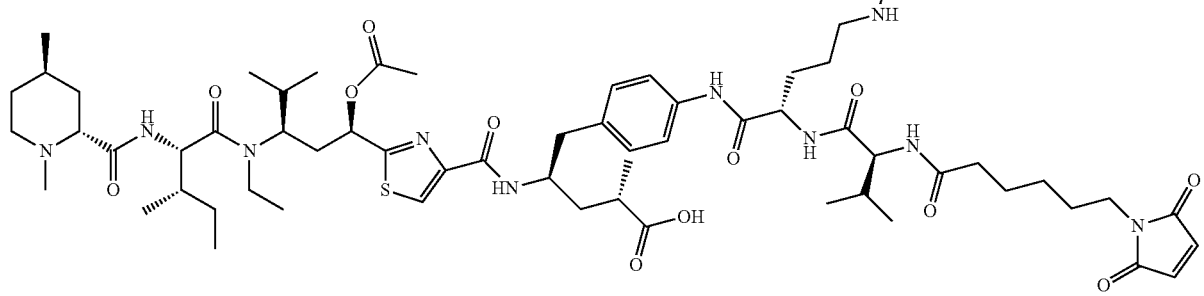

(IIiii)

and an antibody.

31. A pharmaceutical composition containing a compound of claim 1.

32. A pharmaceutical composition containing an antibody-drug conjugate of claim 24.

33. A method of treating cancer by administering to a subject suffering from cancer, an effective amount of a compound of claim 1.

34. The method of claim 33 where the subject is suffering from squamous cell cancer, small-cell lung cancer, non-small cell lung cancer, gastrointestinal cancer, Hodgkin's lymphoma, non-Hodgkin's lymphoma, pancreatic cancer, glioblastoma, glioma, cervical cancer, ovarian cancer, liver cancer, bladder cancer, breast cancer, colon cancer, colorectal cancer, endometrial carcinoma, myeloma, salivary gland carcinoma, kidney cancer, basal cell carcinoma, melanoma, prostate cancer, vulval cancer, thyroid cancer, testicular cancer, esophageal cancer, head and neck cancers, mucinous ovarian cancer, cholangiocarcinoma or renal papillary carcinoma.

35. A method of treating cancer by administering to a subject suffering from cancer, an effective amount of a antibody-drug conjugate of claim 24.

36. The method of claim 35 where the subject is suffering from squamous cell cancer, small-cell lung cancer, non-small cell lung cancer, gastrointestinal cancer, Hodgkin's lymphoma, non-Hodgkin's lymphoma, pancreatic cancer, glioblastoma, glioma, cervical cancer, ovarian cancer, liver cancer, bladder cancer, breast cancer, colon cancer, colorectal cancer, endometrial carcinoma, myeloma, salivary gland carcinoma, kidney cancer, basal cell carcinoma, melanoma, prostate cancer, vulval cancer, thyroid cancer, testicular cancer, esophageal cancer, head and neck cancers, mucinous ovarian cancer, cholangiocarcinoma or renal papillary carcinoma.

37. A pharmaceutical composition containing a compound of claim 12.

38. A method of treating cancer by administering to a subject suffering from cancer, an effective amount of a compound of claim 12.

39. The method of claim 38 where the subject is suffering from squamous cell cancer, small-cell lung cancer, non-small cell lung cancer, gastrointestinal cancer, Hodgkin's lymphoma, non-Hodgkin's lymphoma, pancreatic cancer, glioblastoma, glioma, cervical cancer, ovarian cancer, liver cancer, bladder cancer, breast cancer, colon cancer, colorectal cancer, endometrial carcinoma, myeloma, salivary gland carcinoma, kidney cancer, basal cell carcinoma, melanoma, prostate cancer, vulval cancer, thyroid cancer, testicular cancer, esophageal cancer, head and neck cancers, mucinous ovarian cancer, cholangiocarcinoma or renal papillary carcinoma.

40. A compound having the Formula (IIiv)
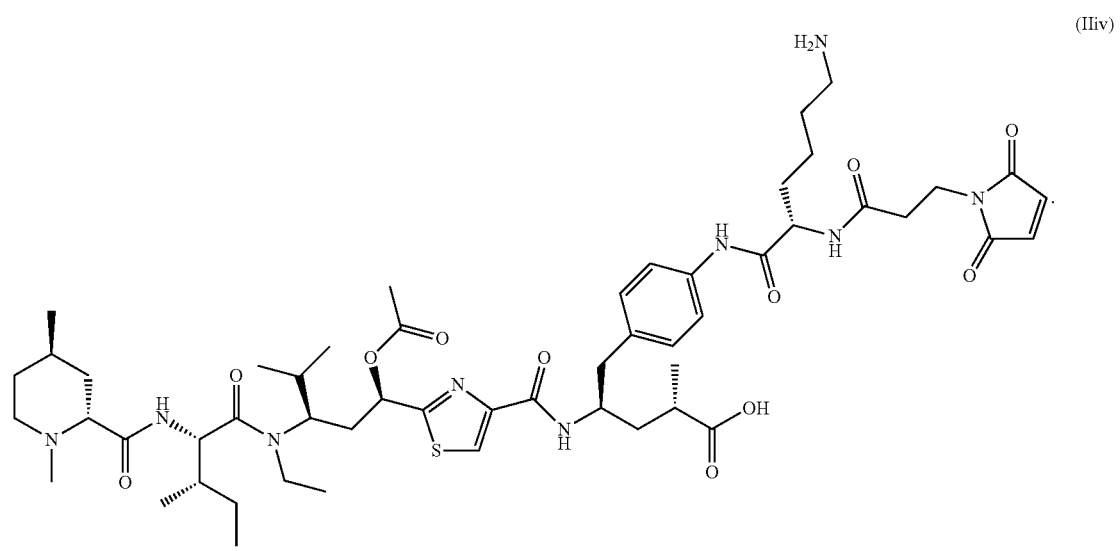 [SMILES: CC[C@H](C)[C@H](NC(=O)[C@H]1C[C@H](C)CCN1C)C(=O)N(CC)[C@H](C[C@@H](OC(C)=O)c1nc(C(=O)N[C@@H](Cc2ccc(NC(=O)[C@H](CCCCN)NC(=O)CCN3C(=O)C=CC3=O)cc2)C[C@H](C)C(=O)O)cs1)C(C)C]
41. An antibody-drug conjugate which is a conjugate of a compound of the Formula (IIiv)
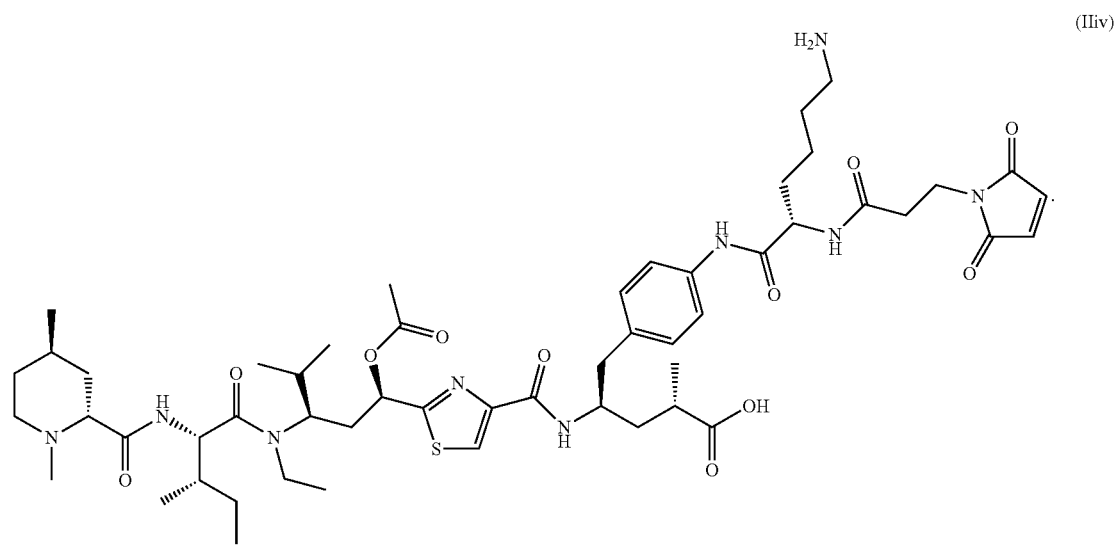 [SMILES: CC[C@H](C)[C@H](NC(=O)[C@H]1C[C@H](C)CCN1C)C(=O)N(CC)[C@H](C[C@@H](OC(C)=O)c1nc(C(=O)N[C@@H](Cc2ccc(NC(=O)[C@H](CCCCN)NC(=O)CCN3C(=O)C=CC3=O)cc2)C[C@H](C)C(=O)O)cs1)C(C)C]
* * * * *